US011883479B2

(12) United States Patent
Sung et al.

(10) Patent No.: US 11,883,479 B2
(45) Date of Patent: Jan. 30, 2024

(54) METHOD FOR TREATING CERVICAL CANCER

(71) Applicants: GENEXINE, INC., Seongnam-si (KR); MSD International GmbH, Lucerne (CH)

(72) Inventors: Young Chul Sung, Seoul (KR); Jung Won Woo, Seoul (KR); Jong Sup Park, Seoul (KR); Jin Won Youn, Yongin-si (KR)

(73) Assignees: GENEXINE, INC., Seongnam-si (KR); MSD International GmbH, Lucerne (CH)

( * ) Notice: Subject to any disclaimer, the term of this patent is extended or adjusted under 35 U.S.C. 154(b) by 318 days.

(21) Appl. No.: 17/240,224

(22) Filed: Apr. 26, 2021

(65) Prior Publication Data

US 2021/0330779 A1 Oct. 28, 2021

Related U.S. Application Data

(60) Provisional application No. 63/015,076, filed on Apr. 24, 2020.

(51) Int. Cl.
| | | |
|---|---|---|
| *A61P 35/00* | (2006.01) | |
| *A61K 39/00* | (2006.01) | |
| *A61K 39/12* | (2006.01) | |
| *A61K 39/39* | (2006.01) | |
| *C07K 14/00* | (2006.01) | |
| *C07K 16/28* | (2006.01) | |
| *C12N 7/00* | (2006.01) | |

(52) U.S. Cl.
CPC .......... *A61K 39/12* (2013.01); *C07K 16/2818* (2013.01); *C07K 16/2827* (2013.01); *C12N 7/00* (2013.01); *A61K 2039/507* (2013.01); *A61K 2039/53* (2013.01); *C12N 2710/20034* (2013.01)

(58) Field of Classification Search
CPC .......... A61P 35/00; A61P 37/04; A61P 35/04; A61K 39/12; A61K 2039/585
See application file for complete search history.

(56) References Cited

U.S. PATENT DOCUMENTS

| | | | |
|---|---|---|---|
| 4,704,362 A | 11/1987 | Itakura et al. | |
| 5,304,489 A | 4/1994 | Rosen | |
| 5,741,957 A | 4/1998 | Deboer et al. | |
| 5,849,992 A | 12/1998 | Meade et al. | |
| 6,004,557 A | 12/1999 | Edwards et al. | |
| 6,342,224 B1 | 1/2002 | Bruck et al. | |
| 7,732,166 B2 | 6/2010 | Cheng et al. | |
| 8,137,674 B2 | 3/2012 | Sung et al. | |
| 9,000,139 B2 | 4/2015 | Sung et al. | |
| 9,399,665 B2 | 7/2016 | Sung et al. | |
| 11,135,262 B2 | 10/2021 | Jin et al. | |

| | | | |
|---|---|---|---|
| 2007/0275003 A1 | 11/2007 | Cassetti et al. | |
| 2010/0158930 A1 | 6/2010 | Zhu et al. | |
| 2013/0195905 A1 | 8/2013 | Sung et al. | |
| 2017/0304385 A1 | 10/2017 | Jin et al. | |

FOREIGN PATENT DOCUMENTS

| | | |
|---|---|---|
| CN | 1679930 A | 10/2005 |
| EP | 1243655 A1 | 9/2002 |
| EP | 1757615 A1 | 2/2007 |
| JP | 10-510989 A | 10/1998 |
| JP | 2001-513986 A | 9/2001 |
| JP | 2006-501825 A | 1/2006 |
| JP | 2009-534027 A | 9/2009 |
| JP | 2013-537422 A | 10/2013 |
| KR | 1998-0009278 A | 4/1998 |
| KR | 2003-0047667 A | 6/2003 |
| KR | 10-2005-0053732 A | 6/2005 |
| KR | 10-2009-0007333 A | 1/2009 |
| KR | 10-2017-0045254 A | 4/2017 |
| WO | 96/19496 A1 | 6/1996 |
| WO | 01/19408 A1 | 3/2001 |
| WO | 2004/030636 A2 | 4/2004 |
| WO | 2007/119896 A1 | 10/2007 |
| WO | 2009/106362 A1 | 9/2009 |
| WO | 2011/128247 A1 | 10/2011 |
| WO | 2012/020871 A1 | 2/2012 |
| WO | 2013/092875 A1 | 6/2013 |
| WO | 2016/024255 A1 | 2/2016 |
| WO | 2018/144775 A1 | 8/2018 |
| WO | 2018/175676 A | 9/2018 |

OTHER PUBLICATIONS

Bais, A.G., et al., "A Shift to a Peripheral Th2-type Cytokine Pattern During the Carcinogenesis of Cervical Cancer Becomes Manifest in CIN III Lesions," Journal of Clinical Pathology 58(10):1096-1100, BMJ Pub. Group, England (2005).

Baldassarre, H., et al., "Production of Transgenic Goats by Pronuclear Microinjection of In Vitro Produced Zygotes Derived From Oocytes Recovered By Laparoscopy," Theriogenology 59(3-4):831-839, Elsevier Science Inc., United States (2003).

Barnes, E., et al., "Novel Adenovirus-based Induce Broad and Sustained T Cell Responses to HCV in Man," Science Translational Medicine 4(115):115ra1, American Association for the Advancement of Science, United States, 22 pages (2012).

Betts, M.R., et al., "Sensitive and Viable Identification of Antigenspecific CD8+ T Cells by a Flow Cytometric Assay for Degranulation," Journal of Immunological Methods 281(1-2):65-78, Elsevier B.V., Netherlands (2003).

Borysiewicz, L.K., et al., "A Recombinant Vaccinia Virus Encoding Human Papillomavirus Types 16 and 18, E6 and E7 Proteins as Immunotherapy for Cervical Cancer," The Lancet 347(9014):1523-1527, Lancet Publishing Group, England (1996).

(Continued)

*Primary Examiner* — Barry A Chestnut
(74) *Attorney, Agent, or Firm* — Sughrue Mion, PLLC

(57) ABSTRACT

A treatment of cervical tumor caused by human papillomavirus (HPV) infection is disclosed. Methods for improving cervical tumor treatment and methods for treating cervical tumor caused by HPV infection include administering a combination of a HPV-specific fusion protein and an immunomodulatory agent.

21 Claims, 18 Drawing Sheets

Specification includes a Sequence Listing.

(56) References Cited

OTHER PUBLICATIONS

Bourgault-Villada, I., et al., "Identification in Humans of HPV-16 E6 and E7 Protein Epitopes Recognized by Cytolytic T Lymphocytes in Association with HLA-B18 and Determination of the HLA-B18-specific Binding Motif," European Journal of Immunology 30(8):2281-2289, Wiley-VCH, Germany (2000).

Brinster, R.L., et al., "Expression of a Microinjected Immunoglobulin Gene in the Spleen of Transgenic Mice," Nature 306(5941):332-336, Macmillan Journals Ltd., England (1983).

Brinster, R.L., et al., "Factors Affecting the Efficiency of Introducing Foreign DNA into Mice by Microinjecting Eggs," Proceedings of the National Academy of Sciences USA 82(13):4438-4442, National Academy of Sciences, United States (1985).

Chen, H-W., et al., "Identification of HLA-A11-restricted CTL Epitopes Derived from HPV Type 18 Using DNA Immunization," Cancer Biology & Therapy 8(21):2025-2032, Taylor & Francis, United States (Nov. 1, 2009).

Clerici, M., et al., "Cytokine Production Patterns in Cervical Intraepithelial Neoplasia: Association With Human Papillomavirus Infection," Journal of the National Cancer Institute 89(3):245-250, Oxford University Press, United States (1997).

Cobrinik, D., et al., "The Retinoblastoma Protein and the Regulation of Cell Cycling," Trends in Biochemical Sciences 17:312-315, Elsevier Scientific Publishers, England (1992).

De Jong, A., et al., "Enhancement of Human Papillomavirus (HPV) Type 16 E6 and E7-specific T-cell Immunity in Healthy Volunteers Through Vaccination With TA-CIN, and HPV16 L2E7E6 Fusion Protein Vaccine," Vaccine 20(29-30):3456-3464, Elsevier Science, Netherlands (2002).

De Vos Van Steenwijk, P.J., et al., "A Placebo-controlled Randomized HPV16 Synthetic Long-peptide Vaccination Study in Women with High-grade Cervical Squamous Intraepithelial Lesions," Cancer Immunology, Immunotherapy 61(9):1485-1492, Springer Verlag, Germany (2012).

De Vos Van Steenwijk, P.J., et al., "Surgery Followed by Persistence of High-grade Squamous Intraepithelial Lesions is Associated with Induction of a Dysfunctional HPV16-specific T-cell Response," Clinical Cancer Research 12(22):7188-7195, American Association of Cancer Research, United States (2008).

Deligeoroglou, E., et al., "HPV Infection: Immunological Aspects and Their Utility in Future Therapy," Infectious Diseases in Obstetrics and Gynecology 2013:540850, Hindawi Publishing, Egypt, 9 pages (Aug. 20, 2013).

Dochez, C., et al., "HPV Vaccines to Prevent Cervical Cancer and Genital Warts: an Update," Vaccine 32(14):1595-1601, Elsevier Science, Netherlands (Mar. 2014).

Einstein, M.H., et al., "Clinician's Guide to Human Papillomavirus Immunology: Knowns and Unknowns," The Lancet. Infectious Diseases 9(6):347-356. The Lancet Publishing Group, United States (2009).

English Language Abstract of Chinese Patent Publication No. CN1679930A, Chinese Patent Office, Espacenet Database (2005).

Evans, T.G., et al., "The Use of Flt3 Ligand as an Adjuvant for Hepatitis B Vaccination of Healthy Adults," Vaccine 21(3-4):322-329, Elsevier Science Ltd., England (2002).

Facchinetti, V., et al., "CD4+ T Cell Immunity Against the Human Papillomavirus-18 E6 Transforming Protein in Healthy Donors: Identification of Promiscuous Naturally Processed Epitopes," European Journal of Immunology 35(3):806-815, Wiley-VCH, Germany (2005).

Forman, D., et al., "Global Burden of Human Papillomavirus and Related Diseases," Vaccine 30(Suppl 5):F12-F23, Elsevier Ltd., England (Nov. 20, 2012).

Gallagher, K.M.E. and Man, S., "Identification of HLA-DR1- and HLA-DR15-retricted Human Papillomavirus Type 16 (HPV16) and HPV18 E6 Epitopes Recognized by CD4+ T Cells from Healthy Young Women," The Journal of General Virology 88(Pt 5):1470-1478, Society For General Microbiology, England (2007).

Garcia, F., et al., "ZYC101a for Treatment of High-Grade Cervical Intraepithelial Neoplasia: A Randomized Controlled Trial," Obstetrics and Gynecology 103(2):317-326, Lippincott Williams & Wilkins, United States (2004).

Gerdes, J., et al., "Cell Cycle Analysis of a Cell Proliferation-associated Human Nuclear Antigen Defined by the Monoclonal Antibody Ki-67," Journal of Immunology 133(4):1710-1715, American Association of Immunologists, United States (1984).

Hahn, H.S., et al., "Distribution of Maternal and Infant Human Papillomavirus: Risk Factors Associated With Vertical Transmission," European Journal of Obsterics & Gynecology and Reproductive Biology 169(2):202-206, Elsevier Scientific Publishers, Ireland (2013).

International Search Report and Written Opinion for International Application No. PCT/IB2015/056214, Korean Intellectual Property Office, Republic of Korea, dated Oct. 16, 2015. 12 pages.

Kaech, S.M., et al., "Effector and Memory T-cell Differentiation: Implications for Vaccine Development," Nature Reviews, Immunology 2(4):251-262, Nature Pub. Group, England (2002).

Kather, A., et al., "Identification of a Naturally Processed HLA-A*0201 HPV18 E7 T Cell Epitope by Tumor Cell Mediated In Vitro Vaccination," International Journal of Cancer 104(3):345-353, Wiley-Liss, United States (2003).

Le, T.P., et al., "Safety, Tolerability and Humoral Immune Responses After Intramuscular Administration of a Malaria DNA Vaccine to Healthy Adult Volunteers," 18(18):1893-1901. Elsevier Science Ltd., England (2000).

Liu, X., et al., "Structure of the Human Papillomavirus E7 Oncoprotein and Its Mechanism for Inactivation of the Retinoblastoma Tumor Suppressor," The Journal of Biological Chemistry 281(1):578-586, American Society for Biochemistry and Molecular Biology, Inc., United States (2006).

Malassagne, B., et al., "Hypodermin A, a new Inhibitor of Human Complement for the Prevention of Xenogeneic Hyperacute Rejection," Xenotransplantation 10(3):267-277, Blackwell Munksgaard, United Kingdom (2003).

Maraskovsky, E., et al., "In Vivo Generation of Human Dendritic Cell Subsets by Flt3 Ligand," Blood 96(3):878-884, The American Society of Hematology, United States (2000).

McKnight, G.S., et al., "Expression of the Chicken Transferrin Gene in Transgenic Mice," Cell 34(2):335-341, MIT, United States (1983).

Mire-Sluis, A.R., et al., "Recommendations for the Design and Optimization of Immunoassays Used in the Detection of Host Antibodies Against Biotechnology Products," Journal of Immunological Methods 289(1-2):1-16, Elsevier B.V., Netherlands (2004).

Morishima, S., et al., "Identification of an HLA-A24-restricted Cytotoxic Lymphocyte Epitope from Human Papillomavirus type-16 E6: The Combined Effects of Bortezomib and Interferon-gamma on the Presentation of a Cryptic Epitope," International Journal of Cancer 120(3):594-604, Wiley-Liss, United States (2007).

Moscicki, A-B., et al., "Updating the Natural History of Human Papillomavirus and Anogenital Cancers," Vaccine 30(5):F24-F33, Elsevier Science, Netherlands (2012).

Nakagawa, M., et al., "Different Methods of Identifying New Antigenic Epitopes of Human Papillomavirus Type 16 E6 and E7 Proteins," Clinical and Diagnostic Laboratory Immunology 11(5):889-896, American Socity For Microbiology, United States (2004).

Nakagawa, M., et al., "HLA class I Binding Promiscuity of the CD8 T-cell Epitopes of Human Papillomavirus Type 16 E6 Protein," Journal of Virology 81(3):1412-1423, American Society For Microbiology, United States (2007).

Nakamura, Y., et al., "Codon Usage Tabulated from International DNA Sequence Databases: Status for the Year 2000," Nucleic Acids Research 28(1):292, Oxford University Press, United Kingdom (2000).

NCBI, "Codon Usage Database," accessed at http://www.kazusa.or.jp/codon/, accessed on Apr. 23, 2013, accessed on Mar. 10, 2017, 1 page.

Neumann, E., et al., "Gene Transfer into Mouse Lyoma Cells By Electroporation in High Electric Fields," The EMBO Journal 1(7):841-845, IRL Press Limited, England (1982).

Nonn, M., et al., "Dendritic Cell-based Tumor Vaccine for Cervical Cancer I: in Vitro Stimulation With Recombinant Protein-pulsed

(56) References Cited

OTHER PUBLICATIONS

Dendritic Cells Induces Specific T Cells to HPV16 E7 or HPV18 E7," Journal of Cancer Research and Clinical Oncology 129(9):511-520, Springer-Verlag, Germany (2003).
Öhlschläger, P., et al., "An Improved Rearranged Human Papillomavirus Type 16 E7 DNA Vaccine Candidate (HPV-16 E7SH) Induces an E7 Wildtype-Specific T cell Response," Vaccine 24:2880-2893, Elsevier Ltd, England (2006).
Pantaleo, G. and Harari, A., "Functional Signatures in Antiviral T-cell Immunity for Monitoring Virus-associated Diseases," Nature Reviews. Immunology 6(5):417-423, Nature Publishing Group, England (2006).
Park, K.S., et al., "Complete Protection Against a H5N2 Avian Influenza Virus by a DNA Vaccine Expressing a Fusion Protein of H1N1 HA and M2e," Vaccine 29(33):5481-5487, Elsevier Ltd., England (2011).
Parkin, D.M. and Bray, F., "Chapter 2: The Burden of HPV-related Cancers," Vaccine 24(S3):11-25, Elsevier Ltd., Englad (2006).
Peghini, B.C., et al., "Local Cytokine Profiles of Patients With Cervical Intraepithelial and Invasive Neoplasia," Human Immunology 73(9):920-926, Elsevier Inc., United States (2012).
Peng, S., et al., "Development of a DNA Vaccine Targeting Human Papillomavirus Type 16 Oncoprotein E6," Journal of Virology 78(16):8468-8476, American Society For Microbiology, United States (2004).
Ressing, M.E., et al., "Human CTL Epitopes Encoded by Human Papillomavirus Type 16 E6 and E7 Identified Studies of HLA-A*0201-binding peptides," The Journal of Immunology 154(11):5934-5943, American Association of Immunologists, United States (1995).
Ressing, M.E., et al., "Occasional Memory Cytotoxic T-Cell Responses of Patients with Human Papillomavirus Type 16-Positive Cervical Lesions Against a Human Leukocyte Antigen-A *0201-Restricted E7-Encoded Epitope," Cancer Research 56(3):582-588, American Association for Cancer Research, United States (1996).
Ridgway, A. A. G., et al., "Introduction of Vector into Host Cells," in Mammalian Expression Vectors, Chapter 24.2, Rodriguez and Denhardt, eds., pp. 470-472, Butterworths, Boston, Mass., United States (1988).
Ritchie, K.A., et al., "Allelic Exclusion and Control of Endogenous Immunoglobulin Gene Rearrangement in κ Trangenic Mice," Nature 312(5994):517-520, Nature Publishing Group, England (1984).
Robl, J.M., et al., "Artificial Chomosome Vectors and Expression of Complex Proteins in Transgenic Animals," Theriogenology 59(1):107-113, Elsevier Science Inc., United States (2003).
Roederer, M., et al., "SPICE: Exploration and Analysis of Post-Cytometric Complex Multivariate Datasets," Cytometry A 79(2):167-174, Wiley-Liss, United States (2011).
Rudolf, M.P., et al., "Human T-Cell Responses to HLA-A-restricted High Binding Affinity Peptides of Human Papillomavirus Type 18 Proteins E6 and E7," Clinical Cancer Research 7(3 Suppl):788s-795s, The Assocation, United States (2001).
Rüther, U. and Müller-Hill, B., "Easy Identification of cDNA Clones." The EMBO Journal 2(10):1791-1794, IRL Press Ltd. England (1983).
Saade, F. and Petrovsky, N., "Technologies for Enhanced Efficacy of DNA Vaccines," Expert Review of Vaccines 11(2):189-209, Taylor & Francis, England (2012).
Sandoval-Montes, C. and Santos-Argumedo, L., "CD38 is Expressed Selectively During the Activation of a Subset of Mature T Cells With Reduced Proliferation but Improved Potential To Produce Cytokines." Journal of Leukocyte Biology 77(4):513-521, Society for Leukocyte Biology, United States (2005).
Schiffman, M., et al., "Human Papillomavirus and Cervical Cancer," Lancet 370(9590):890-907, Elsevier, England (2007).
Schiffman, M.H., et al., "Epidemiologic Evidence Showing That Human Papillomavirus Infection Causes Most Cervical Intraepithelial Neoplasia." Journal of the National Cancer Institute 85(12):958-964, National Institutes of Health, United States (1993).
Seder, R.A., et al., "T-cell Quality in Memory and Protection: Implications for Vaccine Design," Nature Reviews. Immunology 8(4):247-258, Nature Publishing Group, England (2008).
Seo, S.H., et al., "Optimal Induction of HPV DNA Vaccine-induced CD8+ T cell Responses and Therapeutics Antitumor Effect by Antigen Engineering and Electroporation," Vaccine 27(42):5906-5912, Elsevier, The Netherlands (Aug. 3, 2009).
Shedlock, D.J., et al., "Ki-67 Staining for Determination of Rhesus Macaque T Cell Proliferative Responses Ex Vivo," Cytometry A 77(3):275-284, International Society for Advancement of Cytometry, United States (2010).
Smith, T.F. and Waterman, M.S., "Comparison of Biosequences," Advances in Applied Mathematics 2(4):482-489, Academic Press, Inc., United States (1981).
Soares, A., et al., "Novel Application of Ki67 to Quantify Antigen-specific in vitro Lymphoproliferation." Journal of Immunological Methods 362(1-2):43-50, Elsevier, Netherlands (2020).
Stauss, H.J., et al., "Induction of Cytotoxic T Lymphocytes with Peptides in Vitro: Identification of Candidate T-cell Epitopes in Human Papilloma Virus," Proceedings of the National Academy of Sciences U.S.A. 89(17):7871-7875, National Academy of Sciences, United States (1992).
Streeck, H., et al., "The Role of IFN-γ Elispot Assay in HIV Vaccine Research," Nature Protocols 4(4):461-469, Nature Publishing Group, England (2009).
Trimble, C.L., et al., "Naturally Occurring Systemic Immune Responses to HPV Antigens do not Predict Regression of CIN2/3," Cancer Immunology, Immunotherapy 89(5):799-803, Springer International, Germany (2010).
Urbani, S., et al., "Heterologous T Cell Immunity in Severe Hepatitis C Virus Infection," The Journal of Experimental Medicine 201(5):675-680, Rockefeller University Press, United States (2005).
Vasan, S., et al., "In Vivo Electroporation Enhances The Immunogenicity of an HIV-1 DNA Vaccine Candidate in Healthy Volunteers," PLoS One 6(5):e19252, Public Library of Science, United States, 10 pages (2011).
Von Knebel Doeberitz, M., et al., "Inhibition of Tumorigenicity of Cervical Cancer cells in Nude mice by HPV E6-E7 Anti-Sense RNA," International Journal of Cancer 51:831-834, Wiley-Liss, Inc. United States (1992).
Wagner, T.E., et al., "Microinjection of a Rabbit β-Globin Gene into Zygotes and Its Subsequent Expression in Adult Mice and Their Offspring," Proceedings of the National Academy of Sciences USA 78(10):6376-6380, National Academy of Sciences, United States (1981).
Welters, M.J.P., et al., "Induction of Tumor-specific CD4+ and CD8+ T-cell Immunity in Cervical Cancer Patients by a Human Papillomavirus Type 16 E6 and E7 Long Peptides Vaccine," Clinical Cancer Research 14(1):178-187, American Association of Cancer Research, United States (2008).
Wherry, E.J. and Ahmed, R., "Memory CD8 T-cell Differentiation During Viral Infection," Journal of Virology 78(11):5535-5545, American Society For Microbiology, United States (2004).
Wherry, E.J., et al., "Lineage Relationship and Protective Immunity of Memory CD8 T Cell Subsets," Nature immunology 4(3):225-234, Nature Publishing Group, United States (2003).
Wherry, E.J., et al., "Low CD8 T-cell Proliferative Potential and High Viral Load Limit the Effectiveness of Therapeutic Vaccination," Journal of Virology 79(14):8960-8968, American Society For Microbiology, United States (2005).
Wherry, E.J., et al., "Molecular Signature of CD8* T Cell Exhaustion During Chronic Viral Infection," Immunity 27(4):670-684, Elsevier Inc., United States (2007).
Wherry, E.J., et al., "Viral Persistence Alters CD8 T-cell immunodominance and Tissue Distribution and Results in Distinct States of Functional Impairment," Journal of Virology 77(8):4911-4927, American Society For Microbiology, United States (2003).
Wigler, M., et al., "Biochemical Transfer of Single-Copy Eucaryotic Genes Using Total Cellular DNA as Donor," Cell 14(3):725-731, MIT, United States (1978).
Woo, Y.L., et al., "A Prospective Study on the Natural Course of Low-grade Squamous Intraepithelial Lesions and the Presence of

(56) References Cited

OTHER PUBLICATIONS

HPV16 E2-, E6- and E7-specific T-cell Responses," International Journal of Cancer 126(1):133-141, International Union against Cancer, United States (2010).

Yan, J., et al., "Cellular Immunity Induced by a Novel HPV18 DNA Vaccine Encoding an E6/E7 Fusion Consensus Protein in Mice and Rhesus Macaques," Vaccine 26(40):5210-5215, Elsevier Science, Netherlands (2008).

Yan, J., et al., "Induction of Antitumor immunity in Vivo following Delivery of a Novel HPV-16 DNA Vaccine Encoding an E6/E7 Fusion Antigen," Vaccine 27(3):431-440, Elsevier Science, Netherlands (Jan. 14, 2009).

Yang, S-H., et al., "Correlation of Antiviral T-cell Responses With Suppression of Viral Rebound in Chronic Hepatitis B Carriers: A Proof-of-concept Study," Gene Therapy 13(14):1110-1117, Nature Publishing Group, England (2006).

Yugawa, T. and Kiyono, T., "Molecular Mechanisms of Cervical Carcinogenesis by High-risk Human Papillomaviruses: Novel Functions of E6 and E7 Oncoproteins," Reviews in Medical Virology 19(2):97-113, John Wiley & Sons, Ltd., England (2009).

Zajac A.J. and Harrington L.E., "Immune Response to Viruses: Cell-mediated Immunity," Encyclopedia of Virology 3(3):70-77, Elsevier Ltd., England (2008).

Zanier, K., et al, "Solution Structure Anaiysis of the HPV16 E6 Oncoprotein Reveals a Self-association Mechanism Required for ES-mediated Degradation of p53," Structure 20(4):604-617, Eisevier Ltd. United States (2012).

Zur Hausen, H., "Papillomavirus Infections—A Major Cause of Human Cancers," Biochimica et Biophysica Acta 1288:F55-F78, Eisevier Science B.V., Netherlands (1996).

Kim, T., et al., "Clearance of persistent HPV infection and cervical lesion by the therapeutic DNA vaccine in CIN3 patients," Nature Communications 5:1-14, Macmillan, United Kingdom (2014).

Supplementary European Search Report for EP Application No. EP 15832334, Munich, Germany, dated Mar. 8, 2018, 15 pages.

Clinical Trial Identifier NCT02411019 entitled "Safety and Efficacy of GX-188E DNA Therapeutic Vaccine Administered by Electroporation After Observation (GX-188E)," ClinicalTrials.gov, available at https://clinicaltrials.gov/ct2/show/NCT02411019, last accessed on Jul. 12, 2019, 4 pages.

Mak et al., "Lost in Translation: animal models and clinical trials in cancer treatment", Am J Transl Res, 2014, vol. 6, No. 2, pp. 114-118 (5 pages total).

U.S. National Library of Medicine, "Protocol: the Combination of GX-188E Vaccination and Pembrolizumab in Patients with HPV 16 and/or 18+ Cervical Cancer", History of Changes for Study: NCT03444376, 2018, 6 pages total, last visited Dec. 6, 2022.

Grégoire Marret et al., "Pembrolizumab for the treatment of Cervical Cancer", Expert Opinion on Biological Therapy, 2019, vol. 19, No. 9, pp. 871-877 (31 pages total).

Erminia Massarelli, MD et al., "Combining Immune Checkpoint Blockade and Tumor-Specific Vaccine for Patients With Incurable Human Papillomavirus 16-Related Cancer: A Phase 2 Clinical Trial", JAMA Oncology, 2019, vol. 5, No. 1, pp. 67-73 (7 Pages).

Chiara Di Tucci et al., "Therapeutic vaccines and immune checkpoints inhibition options for gynecological cancers," Critical Reviews in Oncology / Hematology, 2018, vol. 128, pp. 30-42 (14 pages total).

Takeo Shibata et al., "The promise of combining cancer vaccine and checkpoint blockade for treating HPV-related cancer," Cancer Treatment Reviews, 2019, vol. 78, pp. 8-16 (10 pages total).

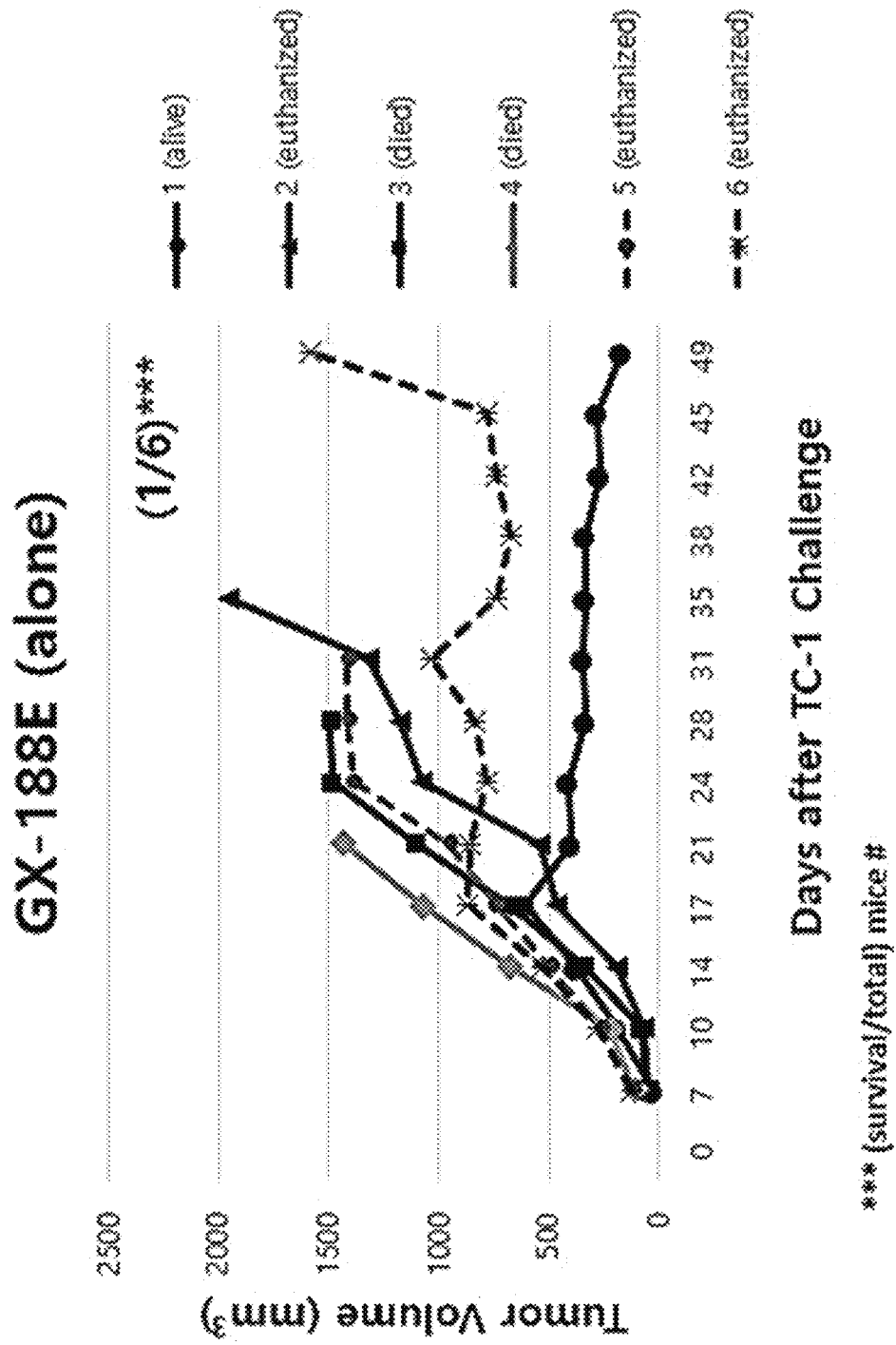

FIG. 4

| Characteristics, N (%) | N=54<br>GX-188E + Pembrolizumab | N=98<br>Pembrolizumab[a] | Characteristics, N (%) | N=54<br>GX-188E + Pembrolizumab | N=98<br>Pembrolizumab[a] |
|---|---|---|---|---|---|
| Age, years | | | HPV type | | |
| Median (Range) | 52 (27-79) | 46.0 (24-75) | 16 | 39 (72.2) | N/A |
| ECOG performance status | | | 18 | 13 (24.1) | |
| 0 | 28 (51.9) | 34 (34.7) | 16 & 18 | 2 (3.7) | |
| 1 | 26 (48.1) | 64 (65.3) | Histology of current diagnosis | | |
| PD-L1 expression status | | | Adenocarcinoma | 14 (25.9) | 5 (5.1) |
| Positive | 41 (75.9) | 82 (83.7) | Adenosquamous carcinoma | - | 1 (1.0) |
| Negative | 13 (24.1) | 15 (15.3) | Squamous cell carcinoma | 40 (74.1) | 92 (93.9) |
| Unknown | | 1 (1.0) | No. of previous lines of therapy | | |
| | | | Adjuvant and/or neoadjuvant | 3 (5.6) | 4 (4.1) |
| | | | 1 | 26 (48.1) | 30 (30.6) |
| | | | 2 | 17 (31.5) | 34 (34.7) |
| | | | ≥3 | 8 (14.8) | 30 (30.6) |

[a] Reference data from Table 1 in J Clin Oncol. 2019; 37(17):1470-1478

FIG. 5

| N=54, TRAEs, N (%) [case] | Any Grade | Grade 3 | Grade 4 |
|---|---|---|---|
| TRAEs by SOC and PT† | 17 (31.5) [38] | 3 (5.6) [4] | 1 (1.9) [1] |
| Endocrine disorders (Hypothyroidism) | 7 (12.9) [7] | | |
| Gastrointestinal disorders | 5 (9.3) [9] | | |
| Diarrhea | 2 (3.7) [3] | | |
| Nausea | 1 (1.9) [2] | | |
| Vomiting | 2 (3.7) [2] | | |
| Gastrointestinal pain | 1 (1.9) [1] | | |
| Mucositis oral | 1 (1.9) [1] | | |
| Skin and subcutaneous tissue disorders | 4 (7.4) [4] | | |
| Pruritus | 1 (1.9) [1] | | |
| Rash | 1 (1.9) [1] | | |
| Urticaria | 1 (1.9) [1] | | |
| Purpura | 1 (1.9) [1] | | |
| Investigations | 2 (3.7) [4] | 2 (3.7) [3] | 1 (1.9) [1] |
| Alanine aminotransferase increased | 2 (3.7) [2] | 1 (1.9) [1] | 1 (1.9) [1] |
| Aspartate aminotransferase increased | 2 (3.7) [2] | 2 (3.7) [2] | |
| Musculoskeletal and connective tissue disorders | 3 (5.6) [3] | | |
| Back pain | 1 (1.9) [1] | | |
| Myalgia | 1 (1.9) [1] | | |
| Pain in extremity | 1 (1.9) [1] | | |
| Nervous system disorders | 3 (5.6) [3] | 1 (1.9) [1] | |
| Syncope | 1 (1.9) [1] | 1 (1.9) [1] | |
| Herpes zoster | 1 (1.9) [1] | | |
| Dizziness | 1 (1.9) [1] | | |

*Any grade ≥ 2 patients; **TRAEs reported as grade 3 or higher regardless of number of patients.
Abbreviations: TRAEs, Treatment-related adverse events.

FIG. 6A

| ORR N (%) | Safety set (N=51) | Efficacy set[a] (N=48) | PD-L1 status[b] | | HPV type | | | Cell type | |
|---|---|---|---|---|---|---|---|---|---|
| | | | Positive (N=36/38) | Negative (N=12/13) | HPV16 (N=34/36) | HPV18 or both (N=14/15) | | SCC (N=36/38) | AC (N=12/13) |
| CR | 6 (11.8) | 6 (12.5) | 6 (16.7) | 0 (0.0) | 6 (17.6) | 0 (0.0) | | 6 (16.7) | 0 (0.0) |
| PR | 10 (19.6) | 10 (20.8) | 9 (25.0) | 1 (8.3) | 6 (17.6) | 4 (28.6) | | 6 (16.7) | 4 (33.3) |
| SD | 8 (15.7) | 8 (16.7) | 7 (19.4) | 1 (8.3) | 6 (17.6) | 2 (14.3) | | 7 (19.4) | 1 (8.3) |
| PD | 26 (51.0) | 24 (50.0) | 14 (38.9) | 10 (83.4) | 16 (47.2) | 8 (57.1) | | 17 (47.2) | 7 (58.4) |
| NE | 1 (1.9) | - | - | - | - | - | | - | - |
| BORR | 16 (31.4) | 16 (33.3) | 15 (41.7/39.5) | 1 (8.3/7.7) | 12 (35.3/33.3) | 4 (28.6/26.7) | | 12 (33.3/31.6) | 4 (33.3/30.8) |
| DCR | 24 (47.1) | 24 (50.0) | 22 (61.1/57.9) | 2 (16.7/15.4) | 18 (52.9/50.0) | 6 (42.9/40.0) | | 19 (52.8/50.0) | 5 (41.7/38.5) |

[a] Patients not receiving 45 days of treatment are considered non-evaluable for response to GX-188E and may be replaced. [b] Criteria for PD-L1: Positive (CPS ≥ 1), Negative (CPS < 1). Abbreviations: BOR, Best Overall Response; DOR, Duration of Response; CR, Complete Response; PR, Partial Response; SD, Stable Disease; PD, Progressive Disease; NE, Non evaluable; DCR, Disease Control Rate; PD-L1, programmed death-ligand 1; SCC, Squamous Cell Carcinoma; AC, Adenocarcinoma

FIG. 6B

| ORR N (%) | Safety set (N=51) | Efficacy set (N=48) | PD-L1 Positive[b] HPV 16 (N=27/20) | | PD-L1 Positive[b] HPV 18 (N=9/10) | | PD-L1 Negative[a] HPV 16 (N=7/8) | | PD-L1 Negative[a] HPV 18 (N=5) | |
|---|---|---|---|---|---|---|---|---|---|---|
| | | | SCC (N=25/26) | AC (N=2) | SCC (N=4) | AC (N=5/10) | SCC (N=4/7) | AC (N=3) | SCC (N=3) | AC (N=2) |
| CR | 6 (11.8) | 6 (12.5) | 6 (24.0) | 0 (0.0) | 0 (0.0) | 0 (0.0) | 0 (0.0) | 0 (0.0) | 0 (0.0) | 0 (0.0) |
| PR | 10 (19.6) | 10 (20.8) | 6 (24.0) | 0 (0.0) | 0 (0.0) | 3 (60.0) | 0 (0.0) | 0 (0.0) | 0 (0.0) | 1 (50.0) |
| SD | 8 (15.7) | 8 (16.7) | 5 (20.0) | 0 (0.0) | 1 (25.0) | 1 (20.0) | 1 (25.0) | 0 (0.0) | 0 (0.0) | 0 (0.0) |
| PD | 26 (51.0) | 24 (50.0) | 8 (32.0) | 2 (100.0) | 3 (75.0) | 1 (20.0) | 3 (75.0) | 3 (100.0) | 3 (100.0) | 1 (50.0) |
| NE | 1 (1.9) | - | - | - | - | - | - | - | - | - |
| BORR | | 16 (33.3) | 12 (48.0/46.2) | 0 (0.0) | 0 (0.0) | 3 (60.0/50.0) | 0 (0.0/0.0) | 0 (0.0) | 0 (0.0) | 1 (50.0) |
| DCR | | 24 (50.0) | 17 (68.0/65.4) | - | 1 (25.0) | 4 (80.0/66.7) | 1 (25.0/20.0) | 0 (0.0) | 0 (0.0) | 1 (50.0) |

[a] Patients not receiving 45 days of treatment are considered non-evaluable for response to GX-188E and may be replaced. [b] Criteria for PD-L1: Positive (CPS ≥ 1), Negative (CPS <1).
Abbreviations: BOR, Best Overall Response; DOR, Duration of Response; CR, Complete Response; PR, Partial Response; SD, Stable Disease; PD, Progressive Disease; NE, Non evaluable; DCR, Disease Control Rate; PD-L1, programmed death-ligand 1; SCC, Squamous Cell Carcinoma; AC, Adenocarcinoma

METHOD FOR TREATING CERVICAL CANCER

CROSS REFERENCE TO RELATED APPLICATIONS

The application claims benefit from U.S. Provisional Application No. 63/015,076 filed on Apr. 24, 2020, the content of which is incorporated herein by reference in its entirety.

SEQUENCE LISTING

The content of the electronically submitted sequence listing, file name: SequenceListing_as_filed.txt; size: 220,516 bytes; and date of creation: Mar. 20, 2021, filed herewith, is incorporated herein by reference in its entirety.

FIELD

This disclosure relates to the treatment of cervical tumor caused by human papillomavirus (HPV) infection. In particular, the disclosure provides methods for improving cervical tumor treatment and methods for treating cervical tumor caused by HPV infection by a combination of a HPV-targeted treatment and an immunomodulatory agent.

BACKGROUND

Persistent viral infection often induces functional inactivation of virus-specific CD8 T cells, impairing their capacity to proliferate, produce immune-stimulatory cytokines, and lyse virally infected cells. Cervical cancer is one of the leading causes of cancer death in women worldwide, and about 75% of its cases are caused by persistent infection with the most common high-risk human papillomavirus (HPV) types, namely HPV16 and HPV18. HPV persistence is usually associated with the lack of demonstrable HPV-specific T-cell immunity, and the virus-specific T cells found in pre-malignant and malignant patients are reported to be generally dysfunctional and sometimes even suppressive. These findings suggest that the functional impairment of virus-specific T cells might be associated with the emergence of HPV-induced cervical cancer.

Cervical cancer arises via a course of high-risk HPV infection, viral persistence, clonal expansion and differentiation of persistently infected cells to a pre-malignant lesion, and their gradual transformation into invasive cancer.

According to World Health Organization (WHO), cervical cancer is the fourth most frequent cancer in women with an estimated 570,000 new cases in 2018 representing 7.5% of all female cancer deaths. The pre-malignant cervical intraepithelial neoplasia 2 and 3 (CIN2 and 3), in particular those positive for HPV16, are considered as high-grade lesions that have approximately a 30% chance of developing into invasive cancer. Therefore, there is urgent need for an effective therapeutic vaccine that can prevent severe complication of persistent HPV infection and eradicate HPV-related neoplasia.

HPV E6 and E7 proteins act as viral oncoproteins by binding and promoting degradation of tumor suppressor proteins, p53 and retinoblastoma (pRb), respectively. These viral oncoproteins are an ideal set of targets for a therapeutic vaccine against CIN2/3 and cervical cancer not only because these proteins induce tumorigenesis but they are also constitutively expressed in HPV-infected pre-malignant and malignant cells. Since the regression of cervical lesions is associated with the presence of a cellular, but not humoral, immune response, a therapeutic vaccine capable of selectively inducing robust E6/E7-specific T-cell immunity is highly desirable.

As one of the ongoing efforts to provide an effective prevention/treatment of cervical cancer caused by HPV, a fusion protein comprising three or more amino acid sequences selected from: (1) an N-terminal portion of an E6 protein of HPV16, (2) a C-terminal portion of an E6 protein of HPV16, (3) an N-terminal portion of an E7 protein of HPV16, (4) a C-terminal portion of an E7 protein of HPV16, (5) an N-terminal portion of an E6 protein of HPV18, (6) a C-terminal portion of an E6 protein of HPV18, (7) an N-terminal portion of an E7 protein of HPV18, and (8) a C-terminal portion of an E7 protein of HPV18, wherein the fusion protein does not bind to p53 or does not form a dimer with an E6 protein of HPV16 or HPV18 and wherein the fusion protein does not bind to pRb or does not form a dimer with an E7 protein of HPV16 or HPV18 was described in co-pending application Ser. No. 15/503,997. The entire content of co-pending application Ser. No. 15/503,997 is incorporated herein by reference.

A fusion protein including a fusion polypeptide configured to transform a 3D structure of E6 and E7 derived from HPV types 16 and 18, and an immunity enhancer peptide, and a polynucleotide encoding the fusion protein are disclosed in co-pending U.S. application Ser. No. 13/816,716. A fusion protein according to one exemplary embodiment of co-pending U.S. application Ser. No. 13/816,716 may include a fusion polypeptide recombined to transform a 3D structure of the E6 and E7 derived from the HPV types 16 and 18. More particularly, the fusion polypeptide is a fusion polypeptide in which 1st to 85th amino acids of the E6 protein derived from the HPV type 16, 1st to 65th amino acids of the E7 protein, 71st to 158th amino acids of the E6 protein, and 51st to 98th amino acids of the E7 protein, 1st to 85th amino acids of the E6 protein derived from the HPV type 18, 1st to 65th amino acids of the E7 protein, 71st to 158th amino acids of the E6 protein, and 51st to 105th amino acids of the E7 protein are bound in sequence. In an embodiment of co-pending U.S. application Ser. No. 13/816,716 is directed to a nucleic acid molecule encoding the fusion polypeptide and an immunity enhancer peptide. Exemplary immunity enhancer peptide includes CD40 ligand, Flt3 ligand, flagellin, and/or OX40. An embodiment of a polynucleotide encoding the fusion protein, an optimized signal sequence (e.g., tPa), and an immunity enhancer peptide (e.g., Flt3 ligand) may be manufactured by reference to Example 1 of co-pending application Ser. No. 13/816,716. The entire content of co-pending U.S. application Ser. No. 13/816,716 is incorporated herein by reference.

Immunotherapy, which enhances the body's own immune system to enable the body to amplify an immune response against cancer cells, can boost or change how the immune system works so it can find and attack cancer cells.

Studies with checkpoint inhibitor antibodies for cancer therapy have generated unprecedented response rates in cancers previously thought to be resistant to cancer treatment. Therapy with antagonistic checkpoint blocking antibodies against CTLA-4, PD-1 and PD-L1 are one of the most promising new avenues of immunotherapy for cancer and other diseases. In contrast to the majority of anti-cancer agents, checkpoint inhibitors do not target tumor cells directly, but rather target lymphocyte receptors or their ligands in order to enhance the endogenous antitumor activity of the immune system. Because immune checkpoint antibodies act primarily by regulating the immune response to diseased cells, tissues or pathogens, they may be used in combination with other therapeutic modalities, such as antibody-drug conjugates to enhance the anti-tumor effect of the antibody-drug conjugates.

Programmed cell death protein 1 (PD-1, also known as CD279) encodes a cell surface membrane protein of the immunoglobulin superfamily, which is expressed in B cells and NK cells. Anti-PD1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer. Exemplary anti-PD1 antibodies include pembrolizumab (KEYTRUDA®, MERCK), nivolumab (BMS-936558, BRISTOL-MYERS SQUIBB), cemiplimab (LIBTAYO®), and pidilizumab (CT-011, CURETECH LTD.).

Programmed cell death 1 ligand 1 (PD-L1, also known as CD274) is a ligand for PD-1, found on activated T cells, B cells, myeloid cells and macrophages. The complex of PD-1 and PD-L1 inhibits proliferation of CD8+ T cells and reduces the immune response. Anti-PDL1 antibodies have been used for treatment of non-small cell lung cancer, melanoma, colorectal cancer, renal-cell cancer, pancreatic cancer, gastric cancer, ovarian cancer, breast cancer, and hematologic malignancies. Exemplary anti-PDL1 antibodies include MDX-1105 (MEDAREX), durvalumab (MEDI4736, MEDIMMUNE), avelumab (BAVENCIO®), atezolizumab (TECENTRIQ®, MPDL3280A, GENENTECH) and BMS-936559 (BRISTOL-MYERS SQUIBB).

Cytotoxic T-lymphocyte antigen 4 (CTLA-4, also known as CD152) is also a member of the immunoglobulin superfamily that is expressed exclusively on T-cells. CTLA-4 acts to inhibit T cell activation and is reported to inhibit helper T cell activity and enhance regulatory T cell immunosuppressive activity. Exemplary anti-CTLA4 antibodies include ipilimumab (Bristol-Myers Squibb) and tremelimumab (PFIZER).

Pembrolizumab (KEYTRUDA®, Merck and Co. Inc.) was recently approved for patients with recurrent or metastatic cervical cancer with disease progression on or after chemotherapy whose tumors express PD-L1 (CPS 1) as determined by an FDA-approved test. The major efficacy outcomes were objective response rate (ORR) according to RECIST 1.1 as assessed by blinded independent central review, and response duration. With a median follow-up time of 11.7 months, the ORR in 77 patients was 14.3% (95% CI: 7.4, 24.1), including 2.6% complete responses and 11.7% partial responses. The estimated median response duration based on 11 patients with a response by independent review was not reached (range 4.1, 18.6+ months); 91% had a response duration of greater than or equal to 6 months. No responses were observed in patients whose tumors did not have PD-L1 expression (CPS<1). The most common adverse reactions in at least 10% of patients with cervical cancer enrolled in clinical trial (KEYNOTE-158) were fatigue, pain, pyrexia, peripheral edema, musculoskeletal pain, diarrhea/colitis, abdominal pain, nausea, vomiting, constipation, decreased appetite, hemorrhage, urinary tract infection (UTI), infections, rash, hypothyroidism, headache, and dyspnea. Pembrolizumab was discontinued due to adverse reactions in 8% of patients. Serious adverse reactions occurred in 39% of patients. The most frequent serious adverse reactions reported included anemia (7%), fistula (4.1%), hemorrhage (4.1%), and infections (except UTIs) (4.1%).

However, there is still need for effective treatment and/or enhancing a treatment of cervical cancer, of which about 70% is caused by HPV 16 and/or 18 infection, and/or a cervical cancer in a patient who is PD-L1 negative.

SUMMARY

The instant disclosure is directed to a combination treatment of cervical cancer, comprising administering to a subject with cervical cancer a fusion protein or a DNA vaccine as described herein and an immunomodulator compound, simultaneously or sequentially. In an embodiment, the cervical cancer is caused by HPV infection.

The instant disclosure is directed to a combination treatment of a cancer comprising administering an effective amount of a HPV vaccine and an immune checkpoint inhibitor, in combination, to treat or enhance the treatment of cervical cancer in a subject in need thereof. In an embodiment, the cervical cancer is caused by HPV infection.

The instant disclosure is directed to a use of a HPV vaccine and an immune checkpoint inhibitor, in combination, in a method to treat or enhance the treatment of cervical cancer in a subject in need thereof, wherein the method comprises administering an effective amount of the HPV vaccine and an effective amount of the immune checkpoint inhibitor to an individual in need of enhancing a treatment or treating a cervical cancer. In an embodiment, the cervical cancer is caused by HPV infection. In an embodiment, the individual is PD-L1 positive or negative. In still an embodiment, the individual is PD-L1 negative. In another embodiment, the individual is PD-L1 positive and infected with HPV 16. In an embodiment, the cervical cancer is advanced, recurrent, or metastatic cervical cancer. In an embodiment, cervical cancer is squamous cell carcinoma or adenocarcinoma. In an embodiment, the individual may be PL-L1 positive and infected with HPV 16, and suffers from squamous cell carcinoma.

The instant disclosure is directed to a combinational therapy composition for treating or enhancing treatment of cervical cancer, in which the combinational therapy composition comprises an effective amount of a HPV vaccine and an effective amount of an immune checkpoint inhibitor, wherein the HPV vaccine and the immune checkpoint inhibitor are administered simultaneously, separately, or sequentially, to an individual in need thereof. In an embodiment, the cervical cancer is caused by HPV infection. In an embodiment, the individual is PD-L1 positive or negative. In still an embodiment, the individual is PD-L1 negative. In another embodiment, the individual is PD-L1 positive and infected with HPV 16. In an embodiment, the cervical cancer is advanced, recurrent, or metastatic cervical cancer. In an embodiment, cervical cancer is squamous cell carcinoma or adenocarcinoma. In an embodiment, the individual may be PL-L1 positive and infected with HPV 16, and suffers from squamous cell carcinoma.

The instant disclosure is directed to a combinational therapy composition for treating or enhancing treatment of cervical cancer, in which the combinational therapy composition consisting essentially of an effective amount of a HPV vaccine and an effective amount of an immune checkpoint inhibitor, wherein the HPV vaccine and the immune checkpoint inhibitor are administered simultaneously, separately, or sequentially, to an individual in need thereof. In an embodiment, the cervical cancer is caused by HPV infection. In an embodiment, the individual is PD-L1 positive or negative. In still an embodiment, the individual is PD-L1 negative. In another embodiment, the individual is PD-L1 positive and infected with HPV 16. In an embodiment, the cervical cancer is advanced, recurrent, or metastatic cervical cancer. In an embodiment, cervical cancer is squamous cell carcinoma or adenocarcinoma. In an embodiment, the individual may be PL-L1 positive and infected with HPV 16, and suffers from squamous cell carcinoma.

The instant disclosure is directed to a pharmaceutical combination for treating human papillomavirus (HPV)-induced cancer in a subject in need thereof, comprising (a) a checkpoint inhibitor therapy component adapted to be administered to the subject including additional boosts of the checkpoint inhibitor therapy, and (b) a HPV vaccine therapy component adapted to be administered to the subject including additional boosts of the HPV vaccine, wherein at therapeutically effective amounts of each of said components (a) and (b), the combined administrations have the capacity to increase the subject's immune response to treat the HPV-induced cancer, over any increase of the individual's immune response by administration of either of the component (a) or (b) alone. In an embodiment, the subject is PD-L1 positive or negative. In still an embodiment, the individual is PD-L1 negative. In another embodiment, the individual is PD-L1 positive and infected with HPV 16. In an embodiment, the cervical cancer is advanced, recurrent, or metastatic cervical cancer. In an embodiment, cervical cancer is squamous cell carcinoma or adenocarcinoma. In an embodiment, the individual may be PL-L1 positive and infected with HPV 16, and suffers from squamous cell carcinoma.

The instant disclosure is directed to a pharmaceutical combination for treating human papillomavirus (HPV)-induced cancer in a subject in need thereof, consisting essentially of (a) a checkpoint inhibitor therapy component adapted to be administered to the subject including additional boosts of the checkpoint inhibitor therapy, and (b) a HPV vaccine therapy component adapted to be administered to the subject including additional boosts of the HPV vaccine, wherein at therapeutically effective amounts of each of said components (a) and (b), the combined administrations have the capacity to increase the subject's immune response to treat the HPV-induced cancer, over any increase of the individual's immune response by administration of either of the component (a) or (b) alone. In an embodiment, the subject is PD-L1 positive or negative. In still an embodiment, the individual is PD-L1 negative. In another embodiment, the individual is PD-L1 positive and infected with HPV 16. In an embodiment, the cervical cancer is advanced, recurrent, or metastatic cervical cancer. In an embodiment, cervical cancer is squamous cell carcinoma or adenocarcinoma. In an embodiment, the individual may be PL-L1 positive and infected with HPV 16, and suffers from squamous cell carcinoma.

The instant disclosure is further directed to a pharmaceutical combination for treating a human papillomavirus (HPV)-cancer patient comprising two separate therapeutic components, including (a) multiple ones of an immune checkpoint inhibitor therapy component to be administered at one dose level, and (b) multiple ones of an HPV vaccine therapy component comprising a polynucleotide of SEQ ID NO: 9, to be administered at a second dose level, wherein the HPV vaccine therapy component (b) is to be administered in combination with the checkpoint inhibitor therapy component (b), wherein each of the components (a) and (b) respectively configured at an effective amount at the first and second dose levels, to increase the immune response of the patient by increasing the potency of the checkpoint inhibitor therapy component (a), to provide a benefit of an enhanced immune response over each of the components (a) and (b) administered alone as monotherapy.

The present disclosure is directed to a use of a pharmaceutical combination in a method of treating a human papillomavirus (HPV)-induced cancer treatment, said method comprising administering an HPV vaccine and a checkpoint inhibitor agent to a subject in need thereof, over a common period of time, for generating a therapeutic effect greater than either the HPV vaccine or checkpoint inhibitor alone when used as monotherapy.

In an aspect of the above-described methods, combination treatments, the uses, the compositions, and the pharmaceutical combinations, the HPV vaccine may be a DNA vaccine. In an embodiment, the immune checkpoint inhibitor is may be a monoclonal antibody. Exemplary embodiments of the monoclonal antibody may be an anti-PD-1 antibody, anti-PD-L1 antibody, or anti-PD-1/PD-L1 antibody, or a combination thereof. In an embodiment, the checkpoint inhibitor may be pembrolizumab. In an embodiment, the HPV vaccine is a DNA vaccine comprising the polynucleotide of SEQ ID NO: 15 or a variant with sequence identity of about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, about 99% or more, or about 100% to SEQ ID NO: 15.

In an aspect of the above-described methods, combination treatments, the uses, the compositions, and the pharmaceutical combinations, the subject, individual, or patient may have advanced, inoperable, or metastatic cervical cancer. The cancer may be recurrent. In an embodiment, the cancer is squamous cell carcinoma or adenocarcinoma. In an embodiment, the cancer is squamous cell carcinoma.

In an aspect of the above-described methods, combination treatments, the uses, the compositions, and the pharmaceutical combinations, the subject, individual, or patient is HPV 16 and/or HPV 18-positive. In another embodiment, the individual is PD-L1 positive and infected with HPV 16. In an embodiment, the individual may be PL-L1 positive and infected with HPV 16, and suffers from squamous cell carcinoma.

In an aspect of the above-described methods, combination treatments, the uses, the compositions, and the pharmaceutical combinations, the subject, individual, or patient has been or is treated with anti-cancer treatment. The anti-cancer treatment may be one of known treatments. In an embodiment, the subject, individual, or patient might have undergone or is taking at least one chemotherapy.

In an aspect of the above-described methods, combination treatments, the uses, the compositions, and the pharmaceutical combinations, the subject, individual, or patient may be PD-L1-positive or PD-1L negative. In another embodiment, the subject, individual, or patient may be HPV 16 positive. In still another embodiment, the subject may be PD-L1-positive and HPV 16 positive, and the cervical cancer is squamous cell carcinoma.

In an aspect of the above-described methods, combination treatments, the uses, the compositions, and the pharmaceutical combinations, the HPV vaccine may be GX-188 or GX-188 variant. GX-188E is a deoxyribonucleic acid construct comprising the sequence of SEQ ID NO: 15 that comprises the sequence encoding an E6/E7 fusion protein of HPV 16 and 18 (SEQ ID NO: 9) coupled to tPA and Flt3L (see, FIG. 1). In an embodiment, about 2 mg GX-188E may be intramuscularly administered at weeks 1, 2, 4, 7, 13, 19, and optional dose at week 46.

In an aspect of the above-described methods, combination treatments, the uses, the compositions, and the pharmaceutical combinations, the checkpoint inhibitor may be pembrolizumab and the dose of the checkpoint inhibitor may be about 200 mg every three weeks. In an embodiment, pembrolizumab may be administered intravenously.

According to an embodiment, a method for treating a HPV-induced cancer in a subject by combining two distinct treatments for administration to the subject within a common time period of at least 13 weeks is disclosed, wherein the method comprises a HPV vaccine therapy and an immune checkpoint inhibitor antibody therapy, wherein an immune checkpoint inhibitor antibody is administered multiple times at a first fixed dose and a vaccine is administered multiple times at a second fixed dose; and wherein a first administration of the HPV vaccine and a first administration of the immune checkpoint inhibitor are occurred on day of the at least 13 weeks period, and subsequent administrations of the HPV vaccine and subsequent administration of the immune checkpoint inhibitor are occurred within the common time period.

In an aspect of the combination treatment, the first fixed dose of the immune checkpoint inhibitor is 50 mg to 500 mg and the second fixed dose of the HPV vaccine is 0.5-5 mg. According to the method, the HPV vaccine is administered intramuscularly and the immune checkpoint inhibitor is administered intravenously. In an embodiment, the immune checkpoint inhibitor is an anti-PD-1 antibody or anti-PD-L1 antibody, and wherein the HPV vaccine comprises a nucleic acid construct of SEQ ID NO: 15 or a functional variant with sequence identity of 85% or more to SEQ ID NO: 15. In still another embodiment, the HPV-induced cancer is metastatic, recurrent or advanced cervical cancer and the subject has been or is subject to an anti-cancer treatment; the HPV is HPV 16, HPV 18, or a combination thereof; and the subject is PD-L1 positive or PD-L1 negative. In another embodiment, the individual is PD-L1 positive and infected with HPV 16. In still another embodiment, the individual may be PL-L1 positive and infected with HPV 16, and suffers from squamous cell carcinoma.

BRIEF DESCRIPTION OF DRAWINGS

FIGS. 2B-2E show anti-tumor efficacy by control (FIG. 2B), anti-mPD1 mAb alone (FIG. 2C), GX-188E alone (FIG. 2D), and a combination of anti-mPD1 mAb+GX-188E (FIG. 2E). GX-188E alone administration group showed a distinct increase in the mean survival period due to retarded tumor cell growth, while the final survival rate was 17% (1/6). GX-188E+anti-mPD-1 mAb combination group showed a distinct increase in the retardation of tumor cell growth and survival period, while the survival rate also increased to 50% (3/6).

FIG. 4 shows baseline characteristics of combinational therapy of GX-188E plus anti-PD1 mAb (pembrolizumab) in comparison with anti-PD1 mAb (pembrolizumab) monotherapy.

FIG. 5 shows safety profile of the GX-188E+anti-PD1 mAb (pembrolizumab) combination treatment, any Grade (31.5), and Grades 3-4 (5.6%), is comparable to anti-PD1 mAb (pembrolizumab) monotherapy employing Keynote-158 monotherapy, where any Grade (65.3%) & Grades 3-4 (12.2%). One of the 3 patients experiencing grade 3 treatment-related adverse events (TRAEs) also had grade 4. No trial drug-related deaths occurred. Overall, GX-188E combined with anti-PD1 mAb (pembrolizumab) was safe and tolerable.

FIGS. 6A and 6B show Best overall response rate (BORR) assessed by RECIST. Six complete responses (CRs) are confirmed, and all cases of CR are observed in patients with PD-L1 positive, HPV 16+ and squamous cell carcinoma. Clinical response is observed in patients with PD-L1 negative, HPV 18+ or adenocarcinoma.

In FIG. 9A, a 63-year-old cervical cancer patient with HPV 16, PD-L1-positive, squamous cell carcinoma who previously received two lines of chemotherapy and had right hilar lymph node metastasis. Axial lung CT showed metastatic lymphadenopathy (arrow). FIG. 9B shows the level of two tumor markers (CEA and TA4) after the combination treatment; dotted lines indicate the cutoff criteria for normal level of tumor markers. In FIG. 9C, a 41-year-old cervical cancer patient with HPV 18, PD-L1-positive, adenocarcinoma who received two lines of chemotherapy. Pelvis CT revealed ova, low-density metastatic mass (arrow) in the pelvic cavity. FIG. 9D shows the level of two tumor markers (CEA and TA4) after the combination treatment; dotted lines indicate the cutoff criteria for normal level of tumor markers.

DETAILED DESCRIPTION

An aspect of the instant disclosure involves the combined administration of an HPV vaccine therapy and an anti-PD-1 checkpoint inhibitory antibody therapy over a common time period, after extensive experimentation, was found to increase the suppressive effect on the growth of cervical cancer, in particular advanced, metastatic, recurrent cervical cancer, compared to anti-PD-1 checkpoint inhibitory antibody therapy. The instant combination treatment shows an enhancement in treatment efficacy in PD-1 positive patients, HPV-16 positive and/or HPV-17 positive patients than HPV vaccine alone or anti-PD-1 checkpoint inhibitory antibody monotherapy. Surprisingly the instant combination therapy further shows a treatment efficacy in PD-1 negative patients, who are not responsive at all in anti-PD-1 antibody monotherapy.

Definition of Terms

Figure 1:
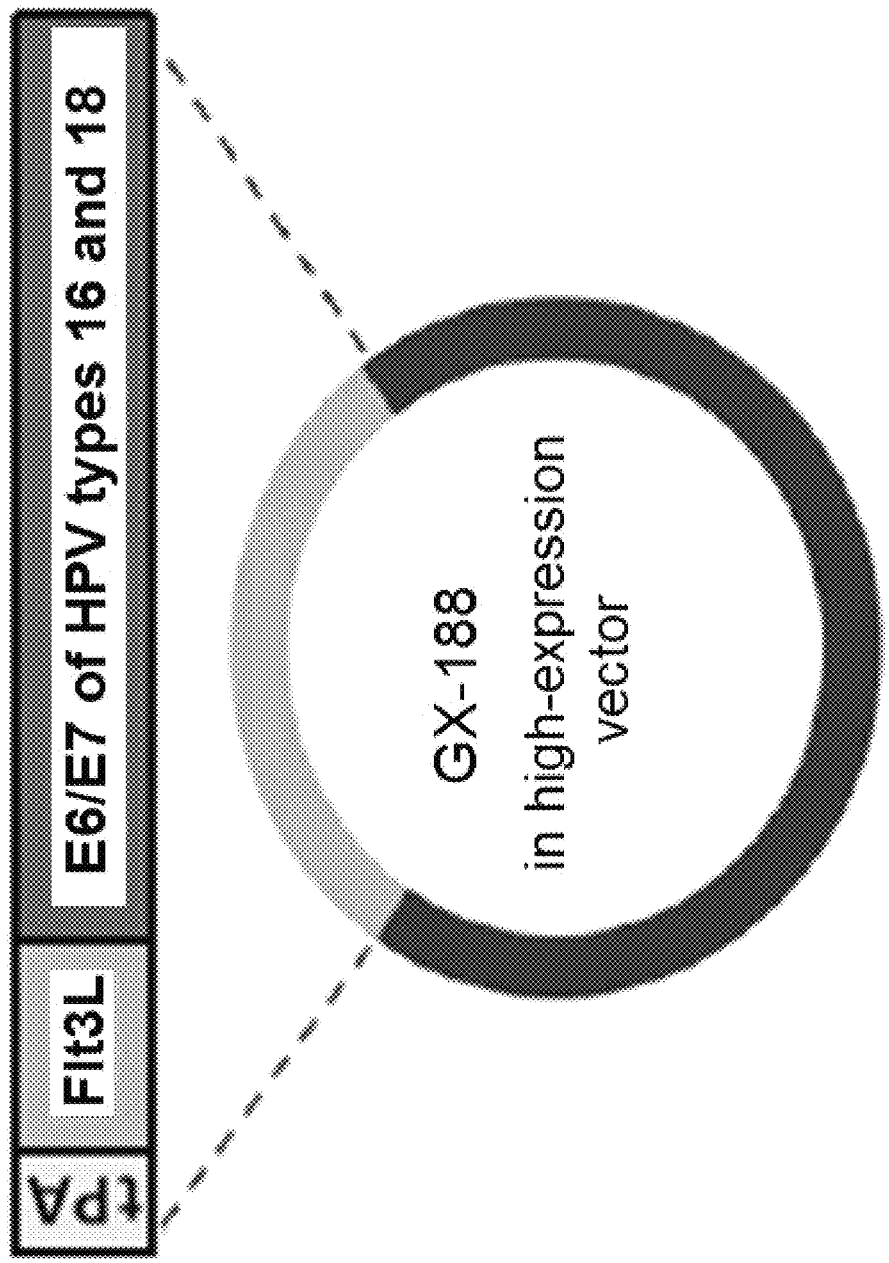
FIG. 1 is a schematic illustration of the structure of a vector carrying GX-188.

The term "GX-188 variant," "GX-188 analogue," "GX-188 variant construct," "GX-188 analogue construct" or any similar terms as used herein indicate that the construct, after administration of at least one dose of the construct, induces a cellular immune response in vivo similar to the cellular immune response induced after administration of GX-188 (FIG. 1 or SEQ ID NO: 9). The cellular immune response can be similar if the variant construct can induce a cellular immune response the same as or higher than the cellular immune response induced by GX-188. In other embodiments, the cellular immune response can be similar if the variant construct induces a cellular immune response at least about 0.9 fold (e.g., 90%), about 0.8 fold, about 0.7 fold, about 0.6 fold, about 0.5 fold, or about 0.4 fold higher than the immune response induced by GX-188. In one embodiment, the cellular immune response is a CD8 T cell response, CD4 T cell response, cytokine secretion, or any combination thereof. In another embodiment, the cellular immune response comprises an increased number of polyfunctional T cells. In certain embodiments, the poly-functional T cells exhibit at least three, at least four, or at least five markers selected from the group consisting of IFN-γ, IL-2, TNF-α, MIP-β, CD107a/b, and any combination thereof, when measured by flow cytometry. An example of the GX-188 variant may be GX-188E (SEQ ID NO: 15).

As used herein the term "GX-188E" is the nucleic acid construct having the nucleotide sequence of SEQ ID NO: 15 or its variant having sequence identify of at least about 80% or more, about 81% or more, about 82% or more, about 84% or more, about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, about 99% or more, or about 100% to SEQ ID NO: 15.

The term "sequence identity" between two polypeptides is determined by comparing the amino acid sequence of one polypeptide to the sequence of a second polypeptide. When discussed herein, whether any particular polypeptide is at least about 50%, about 60%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In an embodiment, the "immunomodulatory compound" includes but is not limited to cytokines, such as interferons, monoclonal antibodies, such as a PD-1/PD-L1 pathway inhibitor (PD-1/PD-L1 inhibitor), anti-CTLA4 antibodies, cyclophosphamide, Thalidomide, Levamisole, Lenalidomide, or a combination thereof. In an embodiment, the immunomodulatory compound is an anti-PD-1 antibody, anti-PD-1/PD-L1 antibody, anti-CTLA4 antibody, a combination of anti-PD1 antibody and an anti-CTLA4 antibody, a combination of anti-PDL1 antibody and an anti-CTLA antibody. The term "PD-1/PD-L1 pathway inhibitor" is a compound inhibits or blocks a binding of PD-L1 to PD-1 and may include an anti-PD-1 antibody, an anti-PD-L1 antibody, and an anti-PD-1/PD-L1 antibody.

The immunomodulatory compounds may be selected from an anti-PD1 antibody such as pembrolizumab or MDX-1106 (Merck), THALOMID® (thalidomide), cyclophosphamide, Levamisole, lenalidomide, CC-4047 (pomalidomide), CC-11006 (Celgene), and CC-10015 (Celgene), and immunomodulatory compound described in any one of WO2007028047, WO2002059106, and WO2002094180. The immunomodulatory compound may an anti-PD1 antibody. In an embodiment, the anti-PD1 antibody is pembrolizumab.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The term "tumor" and "neoplasm" refer to any mass of tissue that result from excessive cell growth or proliferation, either benign (noncancerous) or malignant (cancerous) including pre-cancerous lesions. Tumor can be a cervical tumor. In specific embodiments, the cervical tumor is a benign tumor or a malignant tumor. In certain embodiments, the cervical tumor is squamous cell carcinoma (SCC), adenocarcinoma, adenosquamous carcinoma, small cell carcinoma, neuroendocrine tumor (NET), glassy cell carcinoma, villoglandular adenocarcinoma (VGA), non-carcinoma malignancies, melanoma, lymphoma, or cervical intraepithelial neoplasia (CIN). In some embodiments, the cervical tumor is CIN1, CIN2, CIN3, or cervical cancer.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells).

An "effective amount" of a polynucleotide encoding a fusion protein as disclosed herein is an amount sufficient to carry out a specifically stated purpose. An "effective amount" can be determined empirically and in a routine manner, in relation to the stated purpose.

As used herein, a "therapeutically effective amount" refers to an amount effective, at dosages and for periods of time necessary, to achieve a desired therapeutic result. A therapeutic result may be, e.g., lessening of symptoms, prolonged survival, reduction in size and/or volume of tumor, inhibition of growth of tumor, and the like. A therapeutic result need not be a "cure".

Terms such as "treating" or "treatment" or "to treat" or "alleviating" or "to alleviate" refer to therapeutic measures that cure, slow down, lessen symptoms of, halt progression of a diagnosed pathologic condition or disorder, reduce in size or volume of tumor tissue, and/or stop of tumor growth. Thus, the subjects in need of treatment include those already diagnosed with or suspected of having the disorder.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject.

The term "combination treatment/therapy," "combined treatment," "combinatorial" or "in combination" means at least a vaccine and checkpoint inhibitor treatment, at the same time and/or at different times, within a prescribed time period, with at least the said two distinct therapeutic agents.

The term "checkpoint inhibitor" and/or "antibody" means any one or more of commercial drugs and/or non-commercial drugs designed, whether or not commercialized and/or sold to administer to an individual (or an animal), for unblocking checkpoints in the body which may prevent the immune system, in part or in whole, from attacking a cancer using the body's T cells, and regardless of how administered.

The term "PD-1" or "programmed cell death protein 1" (which also known as CD279) is one example of a checkpoint.

The term "baseline" means the tumor volume (TV) at day 1 for Experiments.

The term "vector" is a term that contains a transcription unit (also known as the "expression vector") and as used herein refers to a viral and/or non-viral expression vector that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like. Viral vectors are preferably made replication defective in normal cells. For example, see U.S. Pat. Nos. 6,669,942; 6,566,128; 6,794,188; 6,110,744 and 5,133,029. The vector can be administered parenterally, such as intravenously, intra-arterially, intramuscularly, subcutaneously, or the like. Administration can also be orally, nasally, rectally, trans-dermally or aerosol inhalation. The vectors may be administered as a bolus or slowly infused. The vector in the instant application is preferably administered subcutaneously.

Composition and Treatment

The composition of GX-188 may be administered parenterally, by injection, for example, either subcutaneously, intracutaneously, intradermally, subdermally or intramuscularly. The terms "GX-188 composition," "composition of GX-188," "GX-188 formulation" and "GX-188-containing formulation" as used herein refers to a composition or formulation comprising a polynucleotide construct comprising the sequence of SEQ ID NO: 9 or 15 or a variant thereof with sequence identity of about 85% or more, about 86% or more, about 87% or more, about 88% or more, about 89% or more, about 89% or more, about 90% or more, about 91% or more, about 92% or more, about 93% or more, about 94% or more, about 95% or more, about 96% or more, about 97% or more, about 98% or more, or about 99% or more to SEQ ID NO: 9 or SEQ ID NO: 15.

Additional formulations which are suitable for other modes of administration include suppositories and, in some cases, oral, nasal, buccal, sublingual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10% (w/w), preferably 1-2% (w/w). Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and may contain 10-95% (w/w) of active ingredient, preferably 25-70% (w/w).

The GX-188-containing formulation may be administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of immunity desired. Suitable dosage ranges are of the order of several hundred micrograms of active ingredient per vaccination with a preferred range from about 1 μg to 20 mg, such as in the range from about 5 μg to 10 mg. In an embodiment, the dose may range from about 0.5 μg to 1000 μg, 1 μg to 1000 μg, or in the range from 1 μg to 500 μg and especially in the range from about 10 μg to 100 μg. In another aspect, the dosage may be in a range from 0.1 mg to 20 mg. In another aspect, the dosage may range from 0.5 mg to 10 mg. In still another aspect, the dosage may range from 1 mg to 5 mg. In still another aspect, the dosage may be in ranges of 0.5-20 mg, 1-20 mg, 0.5-5 mg, 1.5-10 mg, 2-5 mg, 2.5-5 mg, 3-5 mg, or 2-10 mg. In another embodiments, the dosage of GX-188 may be about 0.5 mg, about 0.6 mg, about 0.7 mg, about 0.8 mg, about 0.9 mg, about 1 mg, about 1.1 mg, about 1.2 mg, about 1.3 mg, about 1.3 mg, about 1.4 mg, about 1.5 mg, about 1.6 mg, about 1.7 mg, about 1.8 mg, about 1.9 mg, about 2 mg, about 2.1 mg, about 1.2 mg, about 1.3 mg, about 1.4 mg, about 1.5 mg, about 1.6 mg, about 1.7 mg, about 1.8 mg, about 1.9 mg, about 2 mg, about 2.1 mg, about 2.2 mg, about 2.3 mg, about 2.4 mg, about 2.5 mg, about 2.6 mg, about 2.7 mg, about 2.8 mg, about 2.9 mg, about 3 mg, about 3.1 mg, about 3.2 mg, about 3.3 mg, about 3.4 mg, about 3.5 mg, about 3.6 mg, about 3.7 mg, about 3.8 mg, about 3.9 mg, about 4 mg, about 4.1 mg, about 4.2 mg, about 4.3 mg, about 4.4 mg, about 4.5 mg, about 4.6 mg, about 4.7 mg, about 4.8 mg, about 4.9 mg, or about 5 mg, administered in at intervals of about every week, once every other week, once every three weeks, once every four weeks. The GX-188 formulation may be administered at an interval of 5 days, 10 days, 15 days, 20 days, or 30 days, or 40 days.

According to an aspect, suitable regimens for initial administration and booster shots are also variable but are typified by an initial administration followed by subsequent inoculations or other administrations. For example, in one embodiment, the GX-188 may be administered at a fixed dosage of about 2 mg at week 1, week 2, week 4, week 7, week 13, and week 19, and optionally further at week 46. The administration may be made via an intramuscular route. In another embodiment, GX-188 may be administered at a fixed dosage of about 2 mg at week 1, week 2, week 4, week 8, week 14, and week 20, and optionally further at week 46. In other embodiments, the dosage could vary at each administration.

The immunomodulatory agent may be administered as a separate formulation. In an embodiment, an anti-PD1 antibody may be administered intravenously simultaneously or at different time from the GX-188 administration. The anti-PD1 antibody may be administered at a dose of about 1-1000 mg. In an embodiment, the dose of anti-PD1 antibody may be in ranges of about 10-500 gm, about 50-500 mg, about 100-500 mg, abut 100-300 mg, about 150-300 mg, about 180-250 mg, about 190-250 mg, about 185-225 mg, about 185-220 mg, about 195-250 mg, about 195-225 mg, about 190-230 mg, about 200-400 mg, about 200-300 mg, about 250-300 mg, about 280-350 mg, about 300-500 mg, about 300-400 mg, about 300-1000 mg, about 300-900 mg, about 300-800 mg, about 300-700 mg, or about 300-600 mg. The anti-PD antibody may be administered at intervals of once per week, twice a week, three times a week, four times a week, every week, every 10 days, once every other week, every 20 days, every three weeks, every four weeks, once a month, once every other month, or once every three months, etc. In an embodiment, anti-PD1 antibody is pembrolizumab and may be administered at a dose of 200 mg intravenously three times a week, starting before, at the same time, or after the first administration of GX-188 for the duration of 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks or longer. The duration may be measured by calendar months such as for 1 month, 2 months, 3 months, 4 months, 5 months, 6 months, 7 months, or longer. Or the treatment regimen may include the number of administrations such as 10 doses, 11 doses, 12 doses, 13 doses, 14 doses, 15 doses, 16 doses, 17 doses, 18 doses, 19 doses, 20 doses, 21 doses, 22 doses, 23 doses, 24 doses, 25 doses, 26 doses, 27 doses, 28 doses, 29 doses, 30 doses, 31 doses, 32 doses, 33 doses, 34 doses, 35 doses, or more, at a fixed dosage of, for example, about 200 mg.

A fusion protein comprising the sequence of SEQ ID NO: 10 or its functional variant may be formulated into a vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and organic bases such as isopropylamine, trimethylamine, 2-ethylamino ethanol, histidine, procaine, and the like. A functional variant of fusion protein comprising the sequence of SEQ ID NO: 10 may be a polypeptide of sequence identity of about 85% or more, about 86% or more, about 87% or more, about 88% or more, about 89% or more, about 89% or more, about 90% or more, about 91% or more, about 92% or more, about 93% or more, about 94% or more, about 95% or more, about 96% or more, about 97% or more, about 98% or more, or about 99% or more to SEQ ID NO: 10.

According to an embodiment, the administration of GX-188 and anti-PD1 antibody to a patient with an advanced, inoperable, or metastatic cervical cancer, shows significant treatment effects such as decrease in the size and/or volume of tumor, and improved anti-cancer immune responses as measured by T cell response, PD-L1, CEA, and/or TA4 levels. For example, the administration of a GX-188 variant and an anti-PD1 antibody effectively induced HPV-specific T cell responses. Whereas pembraolizumab monotherapy has no effects on PD-1 negative patients, the combination therapy of GX-188 and pembraolizumab is effective in treating or enhancing treatment of cervical cancer patient who is PD1 negative.

Experiment 1: Pre-Clinical Study

Anti-tumor efficacy of a combination therapy with GX-188E and anti-PD-1 antibody on cervical cancer was assessed in an animal model.

TC-1 cells, which are a cell line from C57BL/6 mouse lung epithelial cells transformed to express E7 of HPV type 16, were selected as the cell line for the production of an animal model for GX-188E efficacy assessments.

Figure 2A:
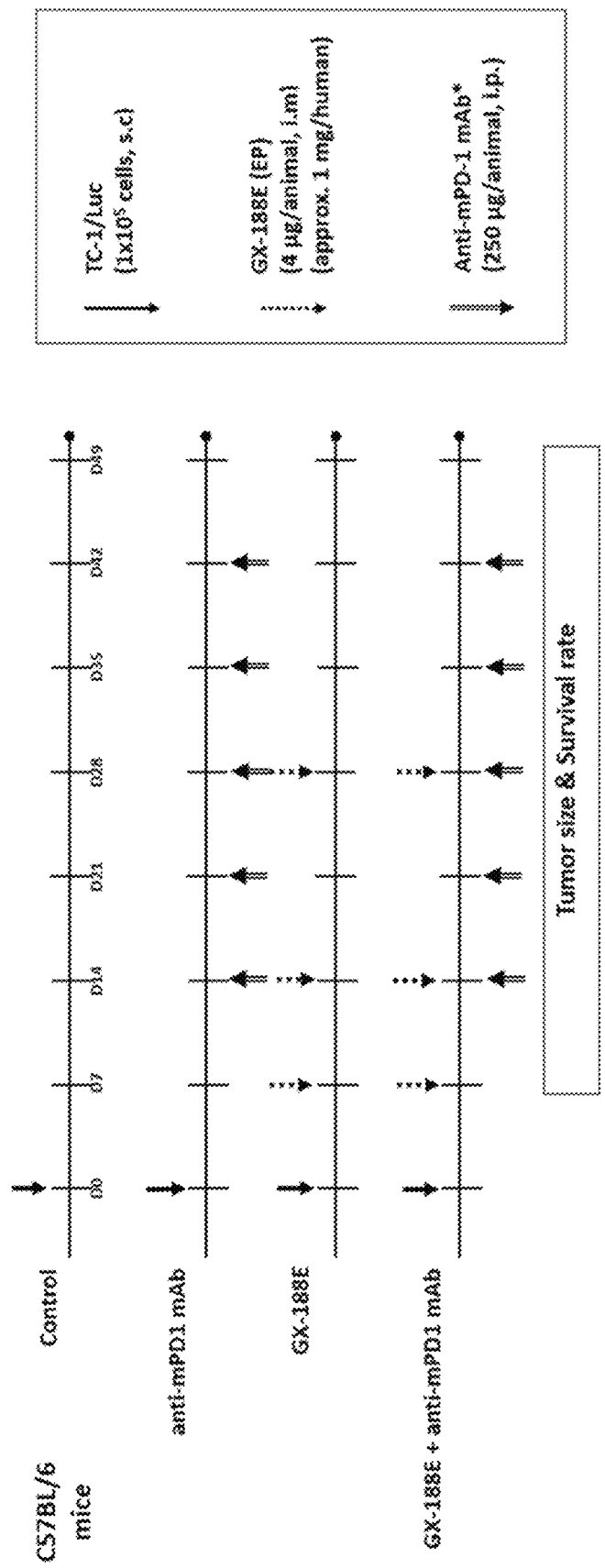
FIG. 2A illustrates a schedule of administrations of tested drug(s) and evaluations of anti-tumor effects in cervical cancer animal model using C57BL/6 mice. D0, D7, D14, D21, D28, D35, D42, and D49 indicate the number of days from the start (D0). Test drugs include anti-mPD1 monoclonal antibody (mAb), GX-188E, and a GX-188E+anti-mPD1 mAb. TC-1/Luc, which is a cell line from C57BL/6 mouse lung epithelial cells transformed to express E7 of HPV type 16, is used to induce tumor in C57BL/6 mice, as described in Experiment 1.
Figure 2B:
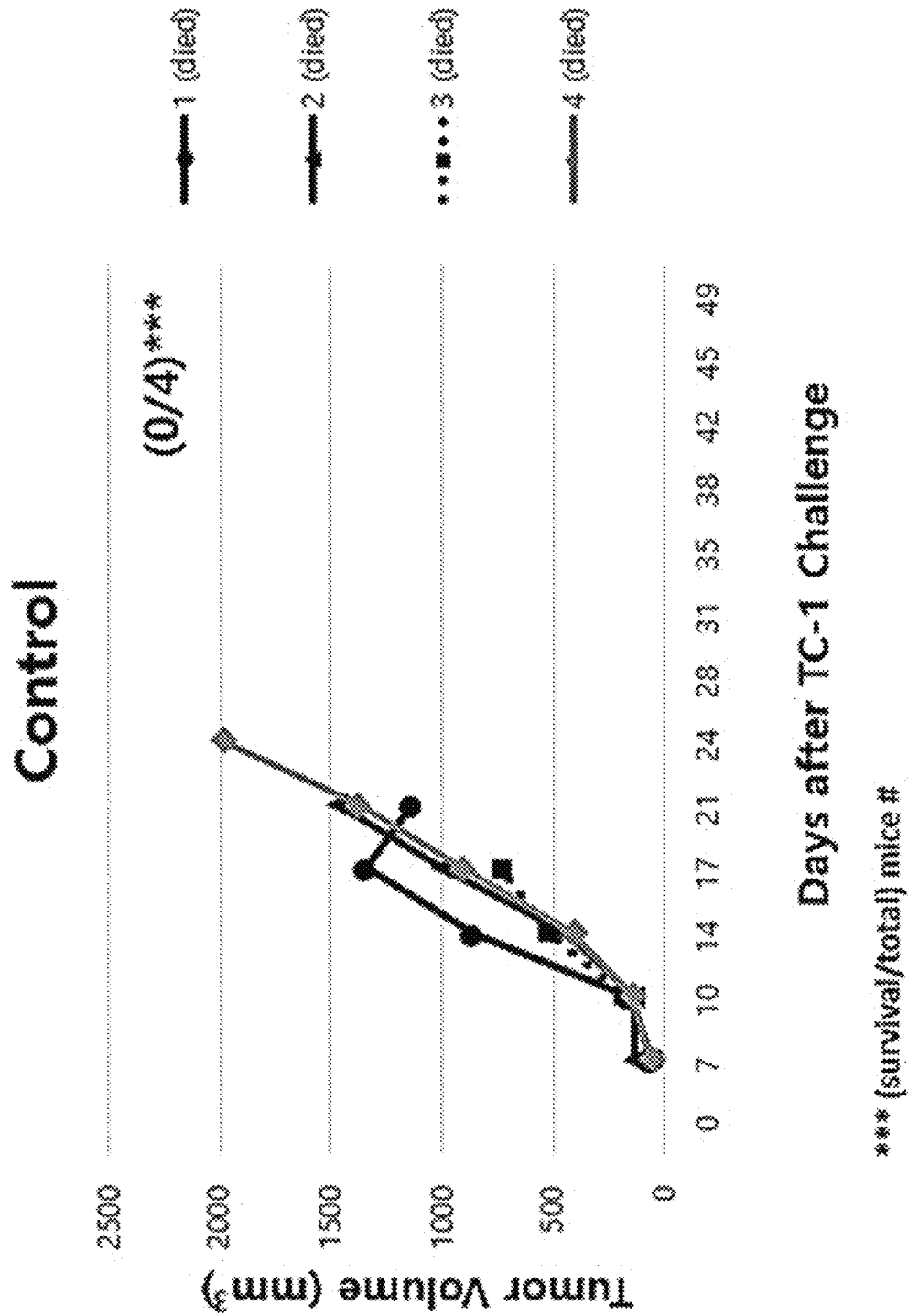
Figure 2C:
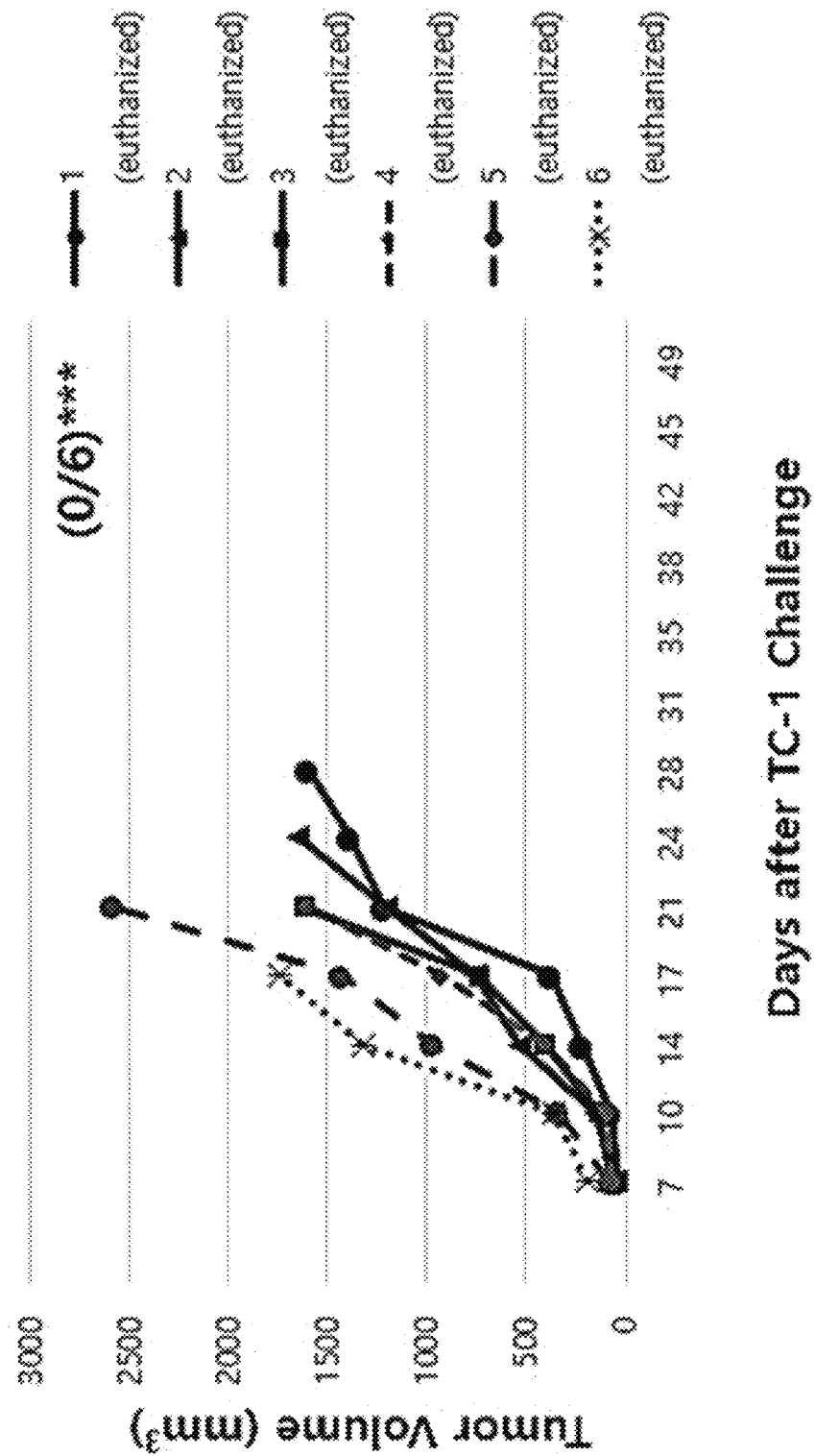
Figure 2E:
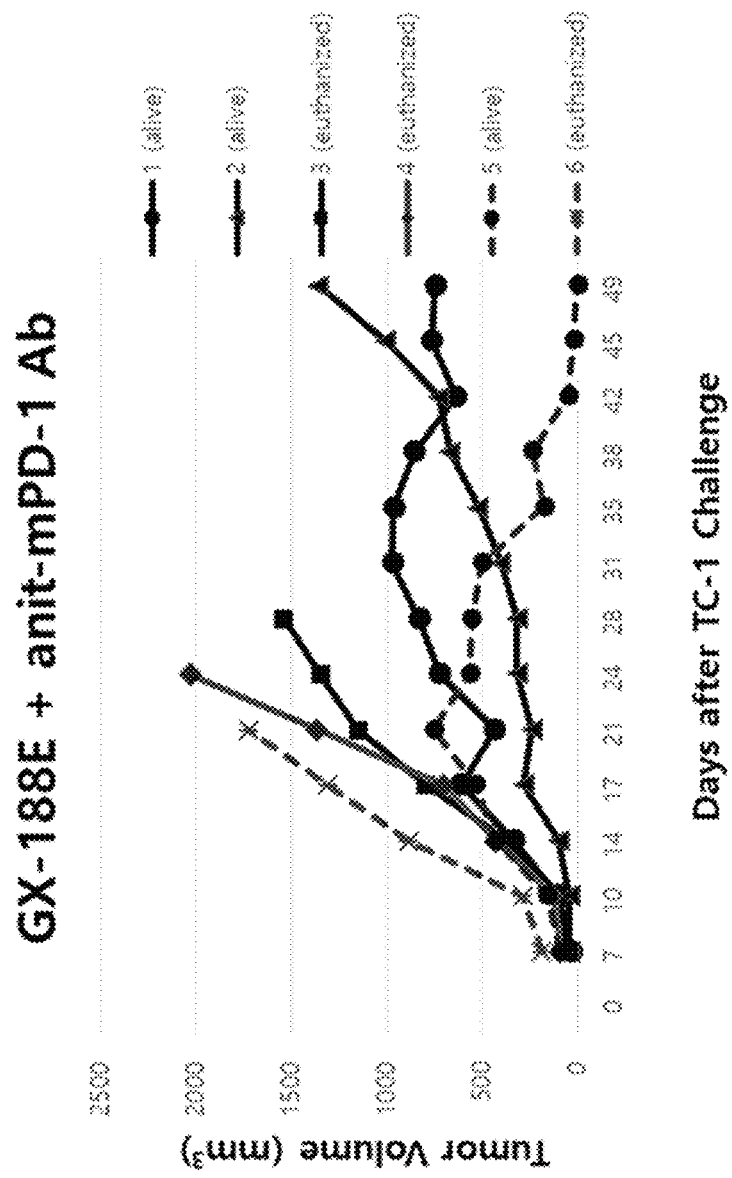

After tumor formation by the subcutaneous transplantation of 1×10⁵ TC-1 tumor cells (provided by Professor Jaetae Lee, Kyungpook National University Hospital) in C57BL/6 mice, the mice were intramuscularly administered 4 µg of GX-188E or formulation buffer (PBS) via electroporation (ORBIJECTOR™, Elimtek Co., Ltd) at weeks 1, 2, and 4. For the combination therapy and anti-mouse PD-1 antibody (anti-mPD-1 mAb) alone groups, 250 µg anti-mPD1 antibodies (BioXcell, clone RMP1-14) were intraperitoneally administered five times at 1-week intervals, starting 2 weeks after the transplantation of TC-1 cells. After the tumor cell challenge, tumor size was measured and survival rate was checked twice a week (FIG. 2A).

All animals in the control (PBS) group died, which confirmed that the tumor challenge conditions used were appropriate. When only anti-mPD-1 antibody was administered, some animals showed a weak effect, i.e. a delayed tumor cell growth, compared to that in the control group. However, because all animals eventually died, the anti-mPD-1 antibody did not induce any change in survival rate. When only GX-188E was administered, there was a distinct increase in the mean survival period due to retarded tumor cell growth, while the final survival rate was 17% (1/6). On the other hand, when a combination of GX-188E and the anti-mPD-1 antibody was administered, there was a distinct increase in the retardation of tumor cell growth and survival period, while the survival rate also increased to 50% (3/6) FIGS. 2B-2E).

Based on the findings, the inventors determined that the antigen-specific cellular immune response induced by GX-188E was able to effectively remove tumor cells that had already formed, which lead to delayed tumor cell growth and an increased survival period. Moreover, the group that received the combination of an immunomodulatory compound and GX-188E therapeutic vaccine showed similar levels of delayed tumor cell growth and prolonged survival as the GX-188E alone group, which also lead to an increase in the survival rate from a long-term perspective.

Inferring based on the mechanism of action of the given immune checkpoint inhibitor, the findings of this study were similar to results of previous studies, which indicated that the anti-PD-1 antibody prolonged the anti-tumor killing activities of T cells. Accordingly, the findings suggest that an immune checkpoint inhibitor is a suitable synergistic partner for enhancing the efficacy of a HPV-targeted immunotherapeutic vaccine including GX-188E.

The findings of this study showed that combining an anti-PD-1 antibody with the immunotherapeutic vaccine GX-188E enhanced the efficacy of GX-188E, which suggested that an immune checkpoint inhibitor could be a suitable candidate for use in combination therapy with an immunotherapeutic vaccine.

Experiment 2: Clinical Study

GX-188E (SEQ ID NO: 15) is an HPV therapeutic DNA vaccine encoding HPV 16/18 E6/E7. Twelve (12) precancer patients were immunized with GX-188E, and seven of nine patients in phase I and 35 of 52 patients in phase II presented regression of cervical lesion within 36 weeks after vaccination. The clinical benefits were associated with enhanced HPV specific IFN-γ responses by GX-188E vaccination. Given the clinical proof of concept in precancer patients, the inventors speculated that, in cervical cancer patients, GX-188E vaccination increases the proportion of clinical responders to immune checkpoint inhibitor by increasing the frequency of HPV-specific T cells.

In phase II clinical trial, the inventors evaluated the safety and efficacy of GX-188E combined with pembrolizumab in patients with HPV 16 and/or 18-positive recurrent/advanced cervical cancer who failed the first or later lines of chemotherapy.

A. Study Design and Participants

The study was a prospective, open-label, phase II study. The protocol was approved by the institutional review board or ethics committee at each study site, and a written informed consent was obtained from each patient. The study was conducted in accordance with the Declaration of Helsinki and all applicable laws.

Fifty-four patients were enrolled and treated with the investigational combination. The inclusion criteria included female patients aged≥18 years who signed an informed consent; those who presented with Eastern Cooperative Oncology Group performance status of 0-1 and histologically confirmed recurrent/advanced HPV-positive (HPV 16 and/or HPV 18) cervical cancer; those who had disease progression after treatment with available therapies for recurrent/advanced cancer. Patients were excluded from the study if they had a history of active central nervous system metastases or active autoimmune disease, an allogeneic solid organ or bone marrow transplant, or a diagnosis of immunodeficiency. All patients submitted either an archival or fresh biopsy sample of their tumor for molecular and histological analyses at screening/baseline. Peripheral blood samples were taken from the patients at screening and at week 1, 4, 7, 10, 16, 22, and 49 for IFN-γ ELISpot assays.

B. Procedures

GX-188E was administered intramuscularly 2 mg either into deltoid or lateralis muscles, followed immediately by co-localized electroporation (TriGrid Delivery System, Ichor medical systems, Inc.) at weeks 1, 2, 4, 7, 13, and 19 with one optional dose at week 46. Pembrolizumab was administered using an intravenous infusion on day 1 of each 3-week treatment cycle after all procedures and assessments have been completed, based on the standard clinical and institutional practices.

To investigate the cellular immune response induced by GX-188E, HPV 16/18 E6/E7-specific T cell responses were analyzed at indicated time in 'Study design and participants'. For the IFN-γ ELISpot analysis (BD Bioscience, CA, USA), cryopreserved and thawed peripheral blood mononuclear cells (PBMCs) were adapted and further processed as described previously in Kim T J, Jin H-T, Hur S-Y, et al. Clearance of persistent HPV infection and cervical lesion by therapeutic DNA vaccine in CIN3 patients. Nature communications 2014; 5(1): 1-14. T cell responses to HPV E6/E7 were measured by comparing signals to the baseline levels and considered positive when the response after vaccination was ≥five-fold higher than that at baseline.

C. Outcomes

Patients were radiographically assessed for responses (by both RECIST v1.1 and iRECIST) approximately every 9 weeks. The safety of the investigational product was evaluated by recording, reporting, and analyzing the results of the laboratory tests and physical examination findings, which considered the patient's underlying disease, adverse reactions, and vital signs. The adverse events (AEs) experienced by patients, such as drug toxicity, was comprehensively evaluated. The investigators evaluated the severity of AEs based on the Common Terminology Criteria for Adverse Events (CTCAE v4.03) by the National Cancer Institute.

D. Statistical Analysis

All patients who received at least one dose of the investigational treatment were included in the safety population and analyzed for safety profile. AEs were coded according to the MedDRA adverse event dictionary. The results were tabulated to examine their frequency, the organ systems they affected, and their relationship to the study treatment. Efficacy results, including Best overall response rate, were analyzed using descriptive statistics. Objective responses were evaluated according to both RECIST v1.1 and Response Evaluation Criteria in Solid Tumors for Immunotherapeutics (iRECIST). Confirmatory scans were acquired for all determinations of objective response (PR or CR), stable disease (SD), and disease progression (PD).

Figure 3:
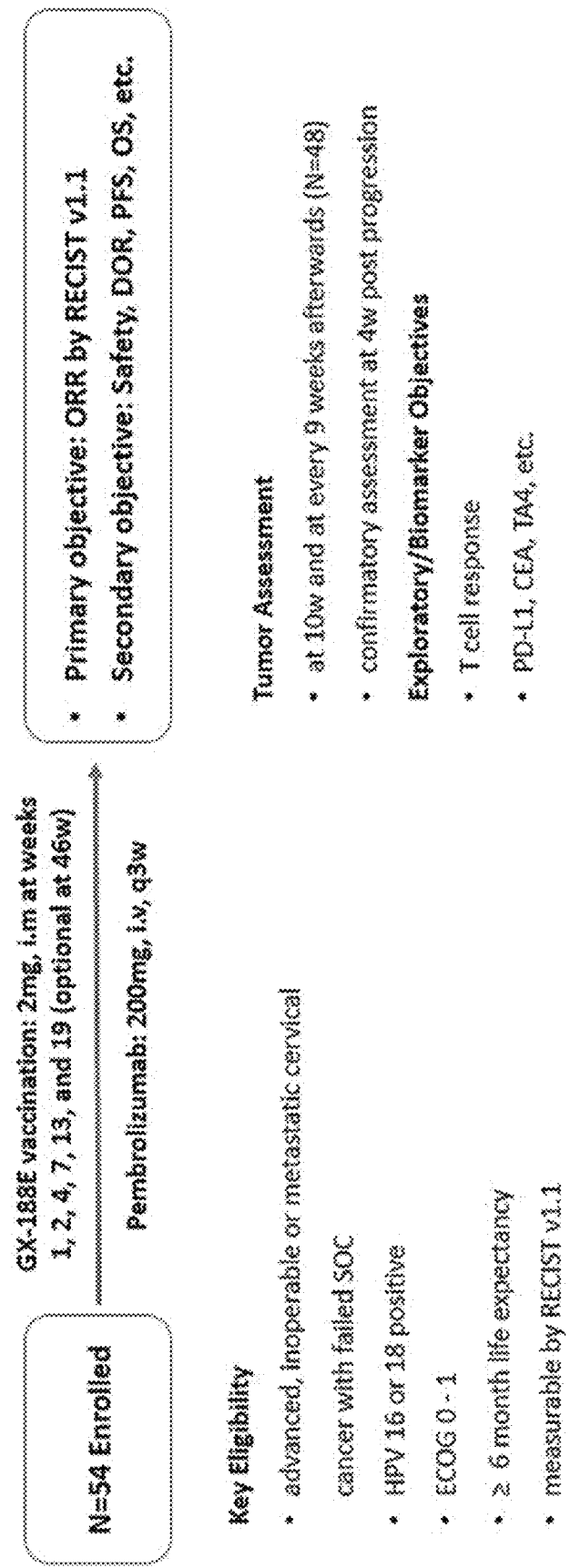
FIG. 3 shows patient enrolment eligibility and primary objectives and secondary objectives. 54 patients were enrolled and 15 patients are ongoing with treatment. For safety analysis, 54 patients receiving at least one dose of either GX-188E or anti-mPD1 mAb (pembrolizumab) were included. For efficacy analysis, 48 patients receiving at least 45 days of treatment were considered evaluable for response to GX-188E by protocol. This interim analysis was performed after obtaining at least one post baseline tumor assessment data.

E. Results 54 patients were enrolled and 48 patients were evaluated for safety (FIG. 3). Three patients not receiving 45 days of treatment were considered non-eligible for evaluation of response to GX-188E vaccination by protocol. Therefore, 48 patients were evaluated for treatment efficacy. The baseline characteristics of the patients who received GX-188E and pembrolizumab combination are shown in FIG. 4, and were similar to those treated with previously reported pembrolizumab monotherapy, except histology and HPV types.

Fifty-four (54) patients were treated and evaluated for safety, showing 31.5% TRAEs (Treatment related Adverse Events) of any grade and 5.6 of grade 3-4 TRAEs (FIG. 5). The most common TRAEs, as classified by the systemic organ class, were gastrointestinal disorders (9.3%) and skin and subcutaneous tissue disorders (7.4%). Three patients (5.6%) experienced grade 3 TRAEs, including one patient with a grade 3 elevation of aspartate aminotransferase (AST) level associated with a grade 4 elevation of alanine aminotransferase (ALT) level. This patient discontinued treatment owing to TRAEs, which were assessed as immune-related adverse events (irAEs). Overall, GX-188E vaccination in combination with an anti-PD1 antibody (pembrolizumab) administration was considered safe and tolerable. FIGS. 6A and 6B show a summary of antitumor responses assessed by radiologists at the study sites.

In FIGS. 5, 6A, and 6B, abbreviations stand for the following meanings:

TRAE: Treatment related Adverse Event;
BOR: Best Overall Response;
DOR: Duration of Response;
CR: Complete Response;
PR: Partial Response;
SD: Stable Disease;
PD: Progressive Disease;
NE: Non evaluable;
DCR: Disease Control Rate;
PD-L1: programmed death-ligand 1;
SCC: Squamous Cell Carcinoma; and
AC: Adenocarcinoma.

As seen in FIG. 6A, BORR 33.3% (16/48) and DCR was 50% (24/48). Among 16 patients with BORR, six patients were confirmed to have CR, which was all durable and ongoing, with duration of response ranging from 1.3 to 24.2 months at the cutoff time; all CR patients were PD-L1 positive, and with HPV 16 and squamous cell carcinoma. Responses were observed in both HPV 16- and/or 18-positive patients, although HPV 16-positive showed favorable response (35.3% vs. 28.6%). Unexpectedly, the response was observed not only in PD-L1-positive tumor but also in PD-L1-negative tumor: the BORR and DCR were 41.7% (15/36) and 61.1% (22/36) in patients with PD-L1-positive tumor and 8.3% (1/12) and 16.7% (2/12) in PD-L1-negative tumor, respectively.

Figure 7:
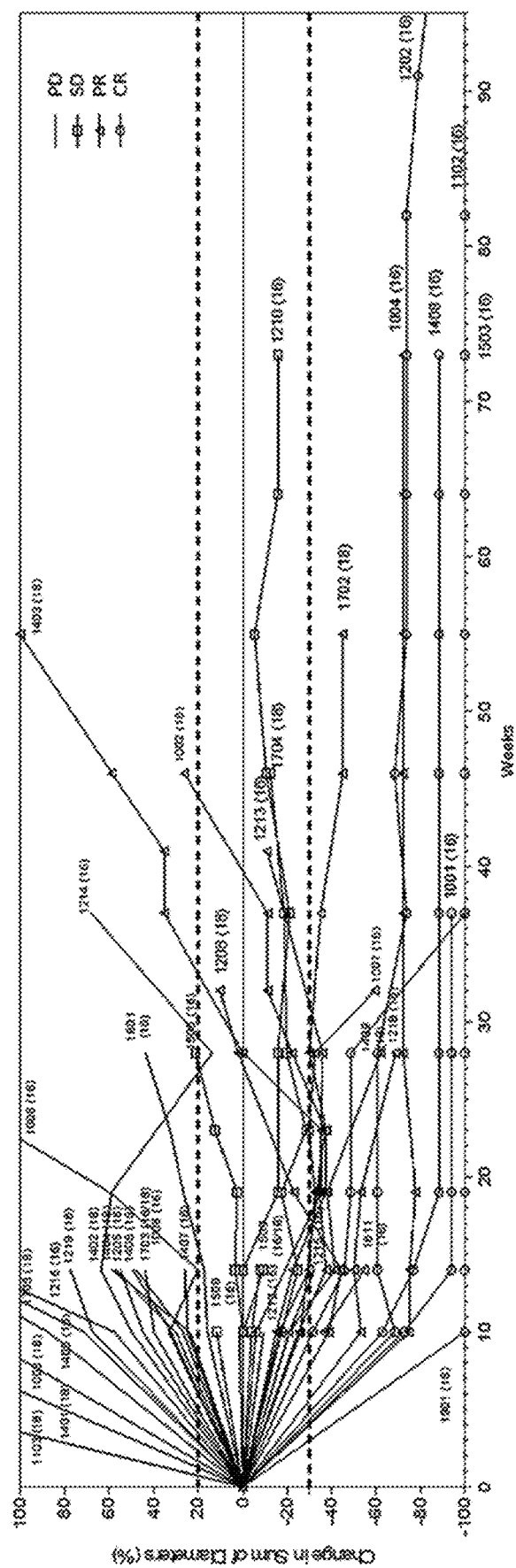
FIG. 7 shows longitudinal change in target lesion from baseline in tumor burden. Currently, Median follow-up was 6.1 months (range; 1.7-24.2 months). CR: Complete response; PR: Partial response; SD: Stable disease; PD: Progressive disease.
Figure 8:
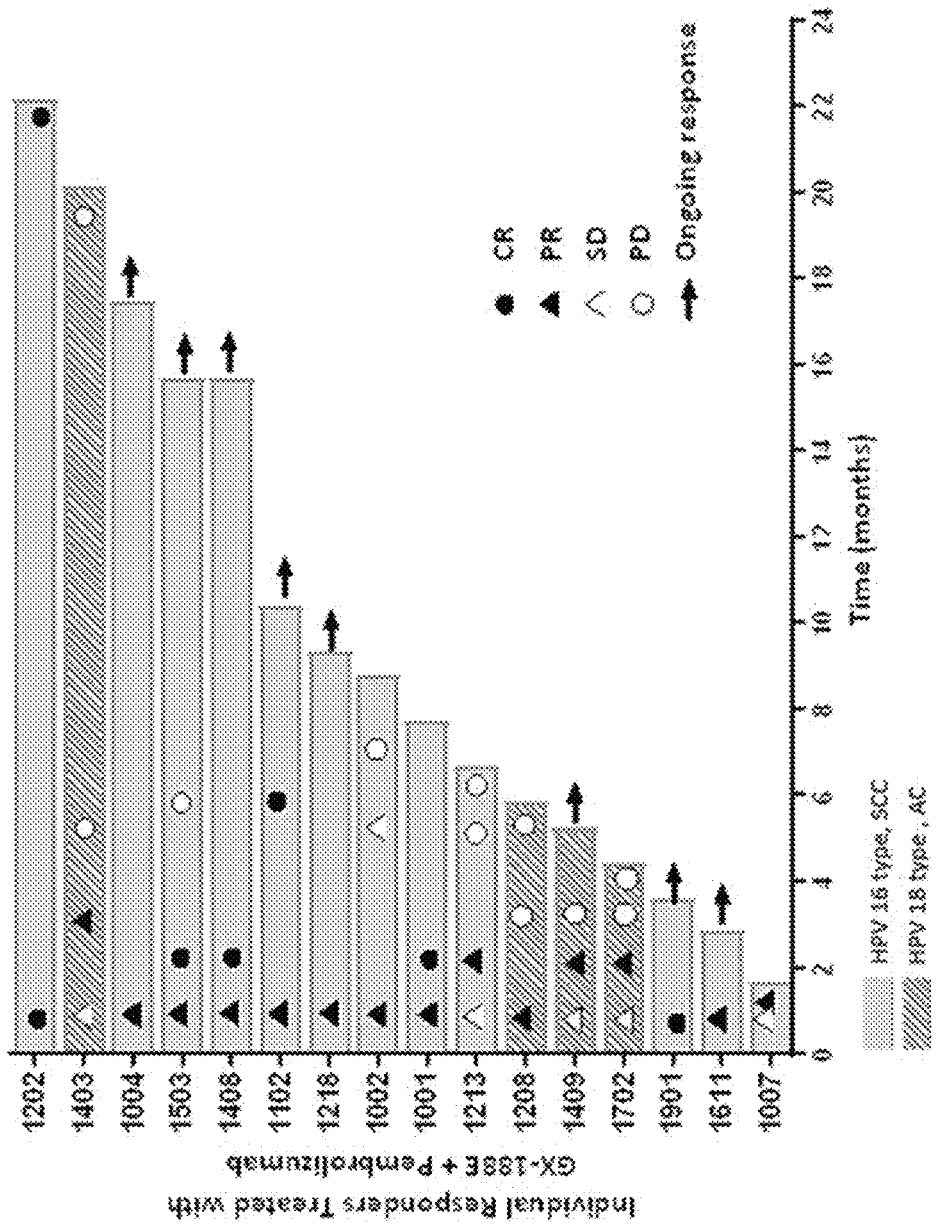
FIG. 8 show the duration of response in patients whose best overall response was CR and PR (N=16) and eight of 16 responses were ongoing. Median PFS was 2.7 months (range; 1.3-24.2) and median OS was not reached.
Figure 9A:
FIGS. 9A-9D show T scan of the target lesion at baseline and post GX-188E with pembrolizumab treatment at weeks 10 and 19 in a patient with CR (FIGS. 9A and 9B), and in a patient with PR (FIGS. 9C and 9D).
Figure 9B:
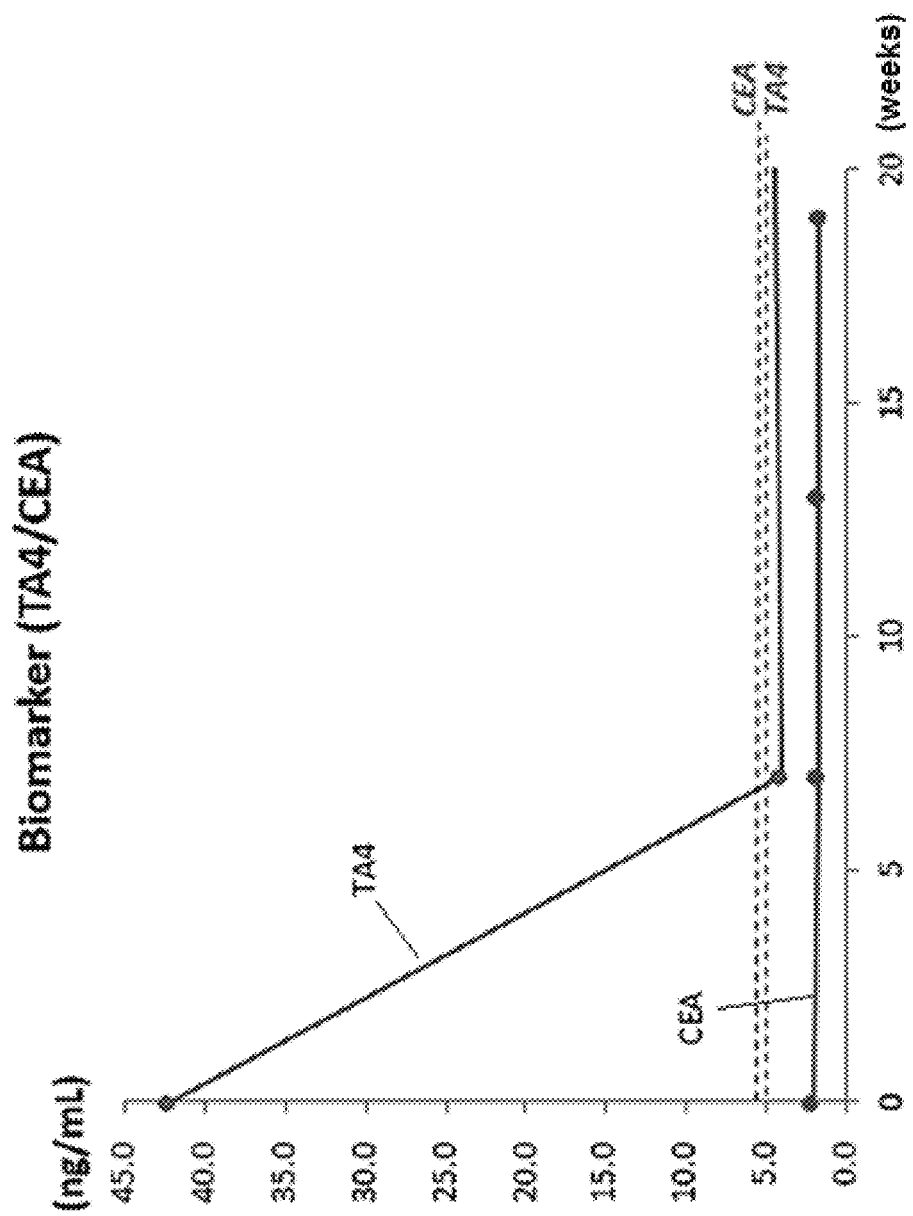
Figure 9C:
Figure 9D:
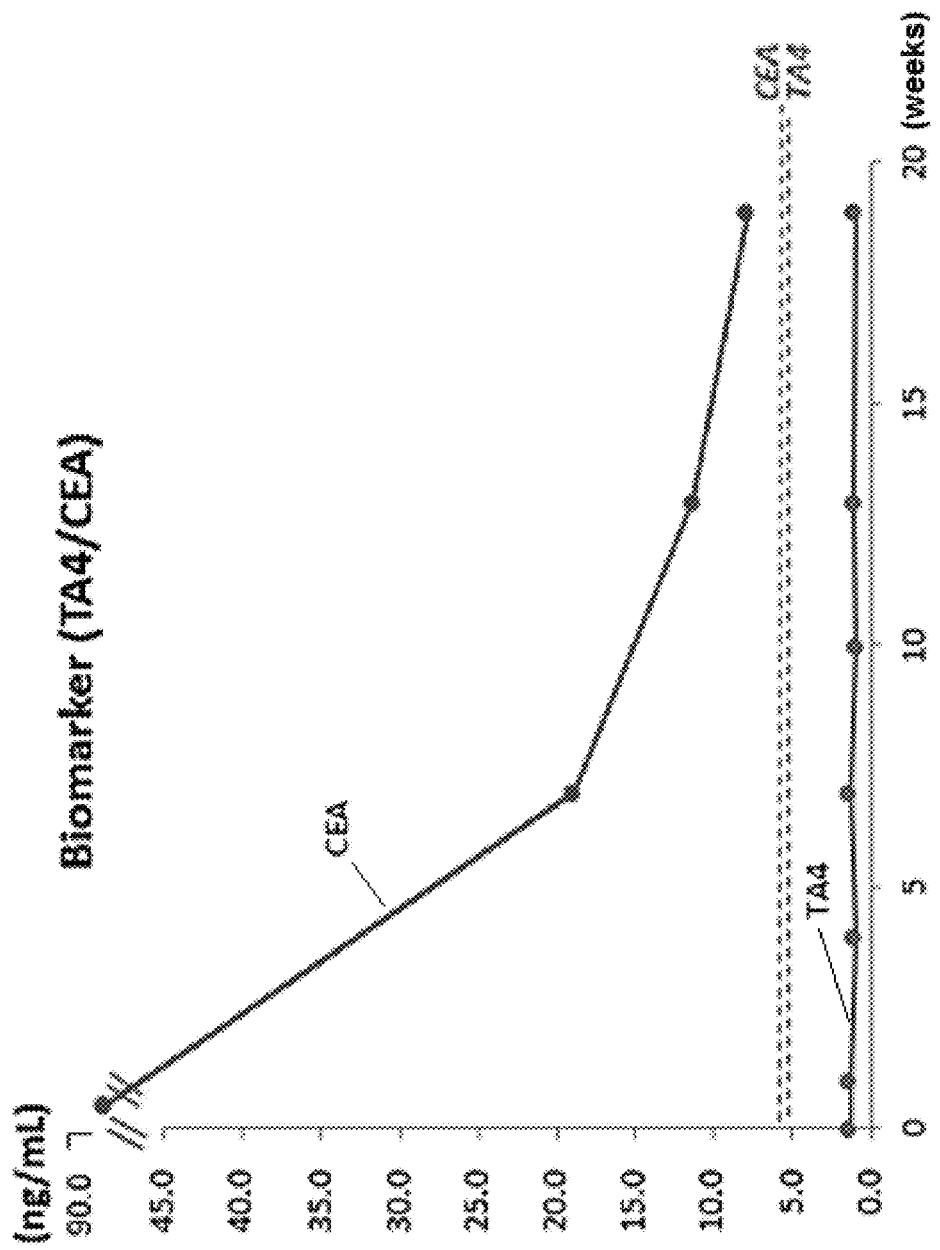

As shown in FIG. 7 and FIG. 8, the patients who showed tumor reduction at week 10 tended to have their responses improved over time. The median follow-up is 6.1 months (range, 1.7 to 24.2 months at cutoff date), by which time 24 patients (50.0%) developed progressive disease (PD). Images of tumor from a 63-year-old patient are shown in FIG. 9A. The patient had HPV 16- and PD-L1-positive squamous cell carcinoma and previously received two lines of chemotherapy and had lymph node metastasis. Following the treatment, the patient showed CR and a significant decrease to normal level in the tumor marker TA4. FIG. 9C shows images of tumor from a 41-year-old patient with HPV 18- and PD-L1-positive adenocarcinoma who previously received two lines of chemotherapy and had pelvic mass and lymph node metastasis. Following treatment, the patient showed PR and a significant decrease in another tumor marker CEA over time. FIGS. 9B and 9D show the level of two tumor markers (CEA and TA4) after the combination treatment; dotted lines indicate the cutoff criteria for normal level of tumor markers.

Figure 10:
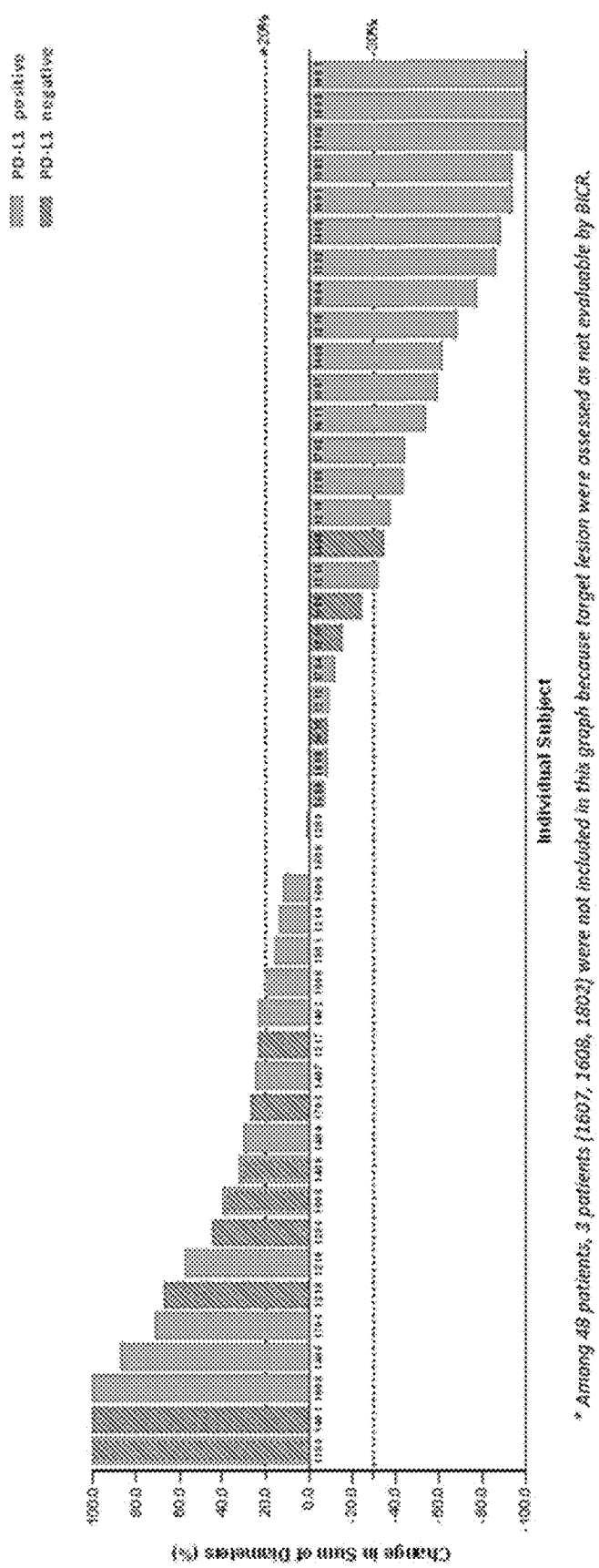
FIG. 10 is a graph showing maximum changes from baseline in sum of target lesion size. Maximum changes from baseline in target lesion were assessed by RECIST v1.1 in patients with one or more evaluable post-baseline images (n=45). Each bar represents one patient and dotted lines indicate RECIST v1.1 criteria for PD (+20%) or PR (−30%). Among 48 patients, 3 patients (patient ID 1607, 1608, 1802) were not included in this graph because target lesion were assessed as not evaluable by blinded independent central review (BICR).

In FIG. 10, maximum changes from the baseline (shown in FIG. 7) in target lesion size are summarized in a waterfall plot with PD-L1 expression status. PD-L1-positive patients responded better to the combination therapy of GX-188E plus pembrolizumab than did PD-L1-negative patients in terms of BORR (15/36 vs. 1/12) (FIG. 6A).

Importantly, target size reduction higher than 30% was observed in one PD-L1-negative patients whereas no responses were observed in PD-L1-negative patients in the previous study of pembrolizumab alone. Regarding antigen-specific T cell responses, results of IFN-γ ELISpot assay were shown as fold-change from the baseline (not shown). Eighteen of 23 response-evaluable patients (78.3%) showed DNA vaccine-induced T cell responses, indicating that GX-188E in combination with pembrolizumab effectively induced HPV E6/E7-specific T cell responses even in heavily pretreated cancer patients.

F. Discussion

The clinical study results show that an HPV vaccination combined with pembrolizumab induced effective antitumor responses in recurrent/advanced, inoperable, or metastatic cervical cancer patients. The clinical benefit was promising (33.3% BORR in total patients, and 41.7% BORR in PD-L1-positive patients). To our knowledge, this is the first report of a combination therapy with a cancer vaccine and an immune checkpoint inhibitor for recurrent/advanced cervical cancer patients. Once tumor antigen-specific T cells are induced by a cancer vaccine, they migrate to and infiltrate tumor tissue, converting cold to hot tumor. Tumor-infiltrating lymphocytes (TIL) secrets IFN-γ which in turn induces expression of PD-L1 from tumor cells, as an adaptive resistance mechanism against immune attack. As an immune checkpoint inhibitor induces antitumor responses by reinvigorating the tumor cytolytic function of the exhausted TIL, the presence of tumor-specific TIL is a prerequisite for antitumor responses to an immune checkpoint inhibitor. As evidenced by the correlation of the absence of TIL and PD-L1 negativity with relatively poor clinical response to immune checkpoint inhibitor, it is suggested that non-immunogenic cold tumors with PD-L1 negativity requires additional strategies for increasing TIL and PD-L1 expression.

Cancer vaccines are regarded as the most efficient method to induce tumor-specific T cell responses. GX-188E vaccination effectively induced Ag-specific T cell responses in HPV precancer patients. It is likely that GX188E vaccination increases the frequency of Tit, followed by enhanced PD-L1 expression in tumor. This is a possible explanation about how GX188E vaccination enhanced clinical efficacy in combination with an anti-PD-1 antibody.

The results show that compared with HPV 16 infection, PD-L1 positive, and squamous cell carcinoma, recurrent/advanced cervical cancer with HPV 18 infection, PD-L1 negative, and adenocarcinoma tends to result in poor clinical responses.

In summary, a combined treatment with GX-188E and an immune checkpoint inhibitor (such as a PD-1/PD-L1 pathway inhibitor including pembrolizumab) in patients with heavily pretreated recurrent/advanced cervical cancer was safe and tolerable, showing similar safety profile to the previously reported pembrolizumab monotherapy. This result indicated that GX-188E vaccination did not add any significant adverse effects while it effectively induced HPV-specific T cell responses in heavily pretreated cervical cancer patients. The present combination treatment showed high response rate of approximately 41.7 in PD-L1-positive patients, 35.3% in HPV 16 positive patients, and 33.3% in squamous cell carcinoma. And the present combination treatment was effective in PD-L1-negative patients, as opposed to the pembrolizumab monotherapy was not effective. Furthermore, the present combination treatment demonstrated clinical responses also in HPV 18 and adenocarcinoma.

Therefore, the present combination treatment of employing GX-188E combined with an anti-PD1 antibody was safe and efficacious for the treatment of patients with HPV 16-/18-positive recurrent or advanced cervical cancer who failed currently available standard therapies, and has a potential to be a new standard therapy for HPV 16/18-related cancers, such as oropharyngeal and anogenital cancers as well as cervical cancer.

The invention claimed is:

1. A method for treating human papillomavirus (HPV)-induced cancer in a subject in need thereof, comprising administering an HPV vaccine and a checkpoint inhibitor agent to the subject, over a common period of time, for generating a therapeutic effect greater than either the HPV vaccine or checkpoint inhibitor alone when used as monotherapy.

2. The method of claim 1, wherein the HPV vaccine comprises a nucleic acid construct of SEQ ID NO: 15 or a functional variant with sequence identity of 85% or more to SEQ ID NO: 15.

3. The method of claim 1, wherein the checkpoint inhibitor agent is a programmed cell death protein (PD)-1/PD-L1 inhibitor.

4. The method of claim 1, wherein a dose of the HPV vaccine is 0.5-5 mg and the HPV vaccine is administered multiple times.

5. The method of claim 1, wherein the HPV vaccine is administered intramuscularly and the checkpoint inhibitor is administered intravenously.

6. The method of claim 1, wherein the checkpoint inhibitor is an anti-PD-1 antibody or anti-PD-L1 antibody.

7. The method of claim 6, wherein the checkpoint inhibitor is selected from the group consisting of pembrolizumab, nivolumab, atezolizumab, avelumab, durvalumab, cemiplimab, and a combination thereof.

8. The method of claim 1, wherein a dose of the checkpoint inhibitor is in a range from about 50 mg to 500 mg and the checkpoint inhibitor is administered before, at the same time, of after the first administration of the HPV vaccine.

9. The method of claim 1, wherein the dose of the HPV vaccine is a 2 mg and the HPV vaccine is administered at week 1, 2, 4, 7, 13, and 19, and further optionally at week 46; and wherein the dose of the checkpoint inhibitor is a 200 mg and the checkpoint inhibitor is administered at an interval of 3 weeks.

10. The method of claim 1, wherein the HPV-induced cancer is cervical cancer.

11. The method of claim 1, wherein the cervical cancer is squamous cell carcinoma or adenocarcinoma.

12. The method of claim 1, wherein the HPV-induced caner is metastatic, recurrent, or advanced cancer and the subject has been or is subject to an anti-cancer treatment.

13. The method of claim 1, wherein the HPV is HPV 16, HPV 18, or a combination thereof.

14. The method of claim 1, wherein the subject is PD-L1 positive or PD-L1 negative.

15. The method of claim 1, wherein the subject is PD-L1 positive and HPV is HPV 16.

16. A method for treating a human papillomavirus (HPV)-induced cancer patient by combining two distinct treatments for administration to the subject within a common time period of at least 13 weeks, said method comprising a HPV vaccine therapy and an immune checkpoint inhibitor therapy, wherein an immune checkpoint inhibitor is administered multiple times at a first fixed dose and a vaccine is administered multiple times at a second fixed dose; and wherein a first administration of the HPV vaccine and a first administration of the immune checkpoint inhibitor are occurred on day of the at least 13 weeks period, and subsequent administrations of the HPV vaccine and subsequent administration of the immune checkpoint inhibitor are occurred within the common time period,
  wherein the HPV-induced cancer is metastatic, recurrent or advanced cervical cancer and the subject has been or is subject to an anti-cancer treatment, said cervical cancer being squamous cell carcinoma or adenocarcinoma;
  wherein the HPV is HPV 16, HPV 18, or a combination thereof; and/or
  wherein the subject is PD-L1 positive or PD-L1 negative.

17. The method of claim 16, wherein the first fixed dose of the immune checkpoint inhibitor is 50 mg to 500 mg and the second fixed dose of the HPV vaccine is 0.5-5 mg.

18. The method of claim 16, wherein the HPV vaccine is administered intramuscularly and the immune checkpoint inhibitor is administered intravenously.

19. The method of claim 16, wherein the immune checkpoint inhibitor is an anti-PD1 antibody or anti-PDL1 antibody, and wherein the HPV vaccine comprises a nucleic acid construct of SEQ ID NO: 15 or a functional variant with sequence identity of 85% or more to SEQ ID NO: 15.

20. The method of claim 16, wherein the cervical cancer is squamous cell carcinoma;
  wherein the HPV is HPV 16; and/or
  wherein the subject is PD-L1 positive.

21. The method of claim 1, wherein the HPV vaccine comprises a nucleic acid construct of SEQ ID NO: 15 or a functional variant thereof with sequence identity of 85% or more to SEQ ID NO: 15 and wherein the checkpoint inhibitor agent is pembrolizumab.

* * * * *

SEQUENCE LISTING

```
<160> NUMBER OF SEQ ID NOS: 116

<210> SEQ ID NO 1
<211> LENGTH: 477
<212> TYPE: DNA
<213> ORGANISM: Human papillomavirus 16
<220> FEATURE:
<221> NAME/KEY: misc_feature
<223> OTHER INFORMATION: E6 nucleotide sequence

<400> SEQUENCE: 1
atgcaccaaa agagaactgc aatgtttcag gacccacagg agcgacccag aaagttacca      60
catttatgca cagagctgca aacaactata catgatataa tattagaatg tgtgtactgc     120
aagcaacagt tactgcgacg tgaggtatat gactttgctt ttcgggattt atgcatagta     180
tatagagatg ggaatccata tgcagtgtgt gataaatgtt taaagtttta ttctaaaatt     240
agtgagtata gatattattg ttatagtgtg tatggaacaa cattagaaca gcaatacaac     300
aaaccgttgt gtgatttgtt aattaggtgt attaactgtc aaaagccact gtgtcctgaa     360
gaaaagcaaa gacatctgga caaaaagcaa agattccata atataagggg tcggtggacc     420
ggtcgatgta tgtcttgttg cagatcatca agaacacgta gagaaaccca gctgtaa       477

<210> SEQ ID NO 2
<211> LENGTH: 158
<212> TYPE: PRT
<213> ORGANISM: Human papillomavirus 16
<220> FEATURE:
<221> NAME/KEY: MISC_FEATURE
<223> OTHER INFORMATION: E6 protein

<400> SEQUENCE: 2

Met His Gln Lys Arg Thr Ala Met Phe Gln Asp Pro Gln Glu Arg Pro
1               5                   10                  15

Arg Lys Leu Pro His Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg Tyr Tyr Cys Tyr Ser Val Tyr Gly Thr Thr Leu Glu
                85                  90                  95
```

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
130                 135                 140

Ser Cys Cys Arg Ser Ser Arg Thr Arg Arg Glu Thr Gln Leu
145                 150                 155

<210> SEQ ID NO 3
<211> LENGTH: 477
<212> TYPE: DNA
<213> ORGANISM: Human papillomavirus 18
<220> FEATURE:
<221> NAME/KEY: misc_feature
<223> OTHER INFORMATION: E6 nucleotide sequence

<400> SEQUENCE: 3

```
atggcgcgct ttgaggatcc aacacggcga ccctacaagc tacctgatct gtgcacggaa      60
ctgaacactt cactgcaaga catagaaata acctgtgtat attgcaagac agtattggaa     120
cttacagagg tatttgaatt tgcattcaaa gatttatttg tagtgtatag agacagtata     180
ccgcatgctg catgccataa atgtatagat ttctattcta gaattagaga attaagatat     240
tattcagact ctgtgtatgg agacacatta gaaaaactaa ctaacactgg gttatacaat     300
ttattaataa ggtgcctgcg gtgccagaaa ccgttgaatc cagcagaaaa acttagacac     360
cttaatgaaa aacgacgatt ccacaaaata gctgggcact atagaggcca gtgccattcg     420
tgctgcaacc gagcacgaca ggagagactc caacgacgca gagaaacaca gtataa        477
```

<210> SEQ ID NO 4
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: E6 protein

<400> SEQUENCE: 4

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg Tyr
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Lys Ile Ala Gly His Tyr Arg Gly Gln Cys His Ser Cys Cys Asn Arg
    130                 135                 140

Ala Arg Gln Glu Arg Leu Gln Arg Arg Glu Thr Gln Val
145                 150                 155

<210> SEQ ID NO 5
<211> LENGTH: 297
<212> TYPE: DNA
<213> ORGANISM: Human papillomavirus 16
<220> FEATURE:
<221> NAME/KEY: misc_feature
<223> OTHER INFORMATION: E7 nucleotide sequence

<400> SEQUENCE: 5

```
atgcatggag atacacctac attgcatgaa tatatgttag atttgcaacc agagacaact    60
gatctctact gttatgagca attaaatgac agctcagagg aggaggatga aatagatggt   120
ccagctggac aagcagaacc ggacagagcc cattacaata ttgtaacctt ttgttgcaag   180
tgtgactcta cgcttcggtt gtgcgtacaa agcacacacg tagacattcg tactttggaa   240
gacctgttaa tgggcacact aggaattgtg tgccccatct gttctcagaa accataa      297
```

<210> SEQ ID NO 6
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: E7 protein

<400> SEQUENCE: 6

```
Met His Gly Asp Thr Pro Thr Leu His Glu Tyr Met Leu Asp Leu Gln
1               5                  10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```

<210> SEQ ID NO 7
<211> LENGTH: 318
<212> TYPE: DNA
<213> ORGANISM: Human papillomavirus 18
<220> FEATURE:
<221> NAME/KEY: misc_feature
<223> OTHER INFORMATION: E7 nucleotide sequence

<400> SEQUENCE: 7

```
atgtatggac ctaaggcaac attgcaagac attgtattgc atttagagcc tcaaaatgaa    60
attccggttg accttctatg tcacgagcaa ttaagcgact cagaggaaga aaacgatgaa   120
atagatggag ttaatcatca acatttacca gcccgacgag ccgaaccaca acgtcacaca   180
atgttgtgta tgtgttgtaa gtgtgaagcc agaattgagc tagtagtaga aagctcagca   240
gacgaccttc gagcattcca gcagctgttt ctgagcaccc tgtcctttgt gtgtccgtgg   300
tgtgcatccc agcagtaa                                                  318
```

<210> SEQ ID NO 8
<211> LENGTH: 105

<212> TYPE: PRT
<213> ORGANISM: Human papillomavirus 18
<220> FEATURE:
<221> NAME/KEY: MISC_FEATURE
<223> OTHER INFORMATION: E7 protein

<400> SEQUENCE: 8

Met Tyr Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Ser Thr Leu Ser Phe
                85                  90                  95

Val Cys Pro Trp Cys Ala Ser Gln Gln
            100                 105

<210> SEQ ID NO 9
<211> LENGTH: 1737
<212> TYPE: DNA
<213> ORGANISM: Artificial Sequence
<220> FEATURE:
<223> OTHER INFORMATION: codon optimized sequence of GX-188 without
      FLT3L and signal peptide

<400> SEQUENCE: 9

```
atgcaccaga agagaaccgc catgttccag gaccctcagg agagacctag gaagctgcct      60
cacctgtgta cagagctcca gacaaccatc cacgacatca tcctggagtg cgtgtactgt     120
aagcagcagc tgctgagaag agaggtgtac gacttcgcct tcagagacct gtgcatcgtg     180
tacagagacg gcaaccctta cgccgtgtgc gataagtgtc tgaagttcta ttccaaaatc     240
tccgaatata ggtacatgca cggcgacacc cctaccctgc acgagtacat gctggacctc     300
cagcctgaga ccacagacct gtactgctac gagcagctga cgacagctc tgaggaagag     360 gacgagattg acggacctgc tggccaggcc gagcctgaca gagcccacta caatatcgtg     420
acattctgtt gcaaatgcga ctccacactg gacaagtgcc tgaagttcta cagcaagatc     480
tctgagtaca gatactactg ctactctgtg tacggcacca cactggagca gcagtacaac     540
aagcctctgt gcgacctcct gatccgctgc atcaactgcc agaagcctct gtgccctgag     600
gagaagcaga gacaccctgga caagaagcag cggttccaca acatcagagg cagatggacc     660
ggcaggtgca tgtcctgctg tagatcctcc agaaccagac gggagaccca gctgcactac     720
aacatcgtga ccttctgctg caagtgcgac tctaccctga actgtgcgt gcagtctacc     780 cacgtggaca tcagaaccct ggaggacctg ctgatgggca ccctgggcat cgtgtgccct     840
atctgctctc agaagcctat ggccaggttc gaggacccta ccagaagacc ctacaagctg     900
cctgacctgt gcaccgagct gaacacctct ctgcaagaca tcgagatcac ctgcgtgtac     960
tgcaagaccg tgctggagct gaccgaggtg ttcgagttcg ccttcaagga cctgttcgtg    1020
gtgtacagag acagcatccc tcacgctgcc tgccacaagt gcatcgactt ctattccagg    1080
atcagggagc tgcgctatta ctccgactct gtgatgtacg ccccaaggc caccctccag    1140 gacatcgtgc tgcacctgga gcctcagaac agagatcccg tggacctgct gtgccacgag    1200
```

-continued

```
cagctgtctg actctgaaga ggagaacgac gagatcgacg gcgtgaacca ccagcacctg    1260
cctgccagga gagctgaacc ccagcggcat accatgctgt gtatgtgctt ctactctagg    1320
atcagagagc tgaggtacta ctctgactct gtgtacggcg acaccctgga agctgacc     1380 aacaccggcc tgtacaacct gctgatccgg tgcctgaggt gccagaagcc tctgaaccct    1440
gccgagaagc tgagacacct gaacgagaag agaagattcc acaagatcgc tggccactac    1500
agaggccagt gccactcttg ctgcaacaga gccagacagg agagactcca gcggagaagg    1560
gagacccagg tggccagaag agccgagcct cagagacaca ccatgctgtg catgtgctgc    1620
aagtgcgagg ccagaatcga gctggtggtg gagagctctg ccgacgacct gagagccttc    1680
cagcagctgt tcctgtctac cctgagcttc gtgtgccctt ggtgcgcctc tcagcag     1737
```

<210> SEQ ID NO 10
<211> LENGTH: 579
<212> TYPE: PRT
<213> ORGANISM: Artificial Sequence
<220> FEATURE:
<223> OTHER INFORMATION: amino acid sequence of GX-188 without FLT3L and
      signal peptide

<400> SEQUENCE: 10

```
Met His Gln Lys Arg Thr Ala Met Phe Gln Asp Pro Gln Glu Arg Pro
1               5                   10                  15

Arg Lys Leu Pro His Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg Tyr Met His Gly Asp Thr Pro Thr Leu His Glu Tyr
                85                  90                  95

Met Leu Asp Leu Gln Pro Glu Thr Thr Asp Leu Tyr Cys Tyr Glu Gln
            100                 105                 110

Leu Asn Asp Ser Ser Glu Glu Glu Asp Glu Ile Asp Gly Pro Ala Gly
        115                 120                 125

Gln Ala Glu Pro Asp Arg Ala His Tyr Asn Ile Val Thr Phe Cys Cys
    130                 135                 140

Lys Cys Asp Ser Thr Leu Asp Lys Cys Leu Lys Phe Tyr Ser Lys Ile
145                 150                 155                 160

Ser Glu Tyr Arg Tyr Tyr Cys Tyr Ser Val Tyr Gly Thr Thr Leu Glu
                165                 170                 175

Gln Gln Tyr Asn Lys Pro Leu Cys Asp Leu Leu Ile Arg Cys Ile Asn
            180                 185                 190

Cys Gln Lys Pro Leu Cys Pro Glu Glu Lys Gln Arg His Leu Asp Lys
        195                 200                 205

Lys Gln Arg Phe His Asn Ile Arg Gly Arg Trp Thr Gly Arg Cys Met
    210                 215                 220

Ser Cys Cys Arg Ser Ser Arg Thr Arg Arg Glu Thr Gln Leu His Tyr
225                 230                 235                 240

Asn Ile Val Thr Phe Cys Cys Lys Cys Asp Ser Thr Leu Arg Leu Cys
                245                 250                 255

Val Gln Ser Thr His Val Asp Ile Arg Thr Leu Glu Asp Leu Leu Met
```

|  |  |  |  | 260 |  |  |  | 265 |  |  |  | 270 |  |  |
|---|---|---|---|---|---|---|---|---|---|---|---|---|---|---|

Gly Thr Leu Gly Ile Val Cys Pro Ile Cys Ser Gln Lys Pro Met Ala
              275              280              285

Arg Phe Glu Asp Pro Thr Arg Arg Pro Tyr Lys Leu Pro Asp Leu Cys
290                    295              300

Thr Glu Leu Asn Thr Ser Leu Gln Asp Ile Glu Ile Thr Cys Val Tyr
305                310              315              320

Cys Lys Thr Val Leu Glu Leu Thr Glu Val Phe Glu Phe Ala Phe Lys
              325              330              335

Asp Leu Phe Val Val Tyr Arg Asp Ser Ile Pro His Ala Ala Cys His
              340              345              350

Lys Cys Ile Asp Phe Tyr Ser Arg Ile Arg Glu Leu Arg Tyr Tyr Ser
              355              360              365

Asp Ser Val Met Tyr Gly Pro Lys Ala Thr Leu Gln Asp Ile Val Leu
              370              375              380

His Leu Glu Pro Gln Asn Glu Ile Pro Val Asp Leu Leu Cys His Glu
385                390              395              400

Gln Leu Ser Asp Ser Glu Glu Asn Asp Glu Ile Asp Gly Val Asn
              405              410              415

His Gln His Leu Pro Ala Arg Arg Ala Glu Pro Gln Arg His Thr Met
              420              425              430

Leu Cys Met Cys Phe Tyr Ser Arg Ile Arg Glu Leu Arg Tyr Tyr Ser
              435              440              445

Asp Ser Val Tyr Gly Asp Thr Leu Glu Lys Leu Thr Asn Thr Gly Leu
450                455              460

Tyr Asn Leu Leu Ile Arg Cys Leu Arg Cys Gln Lys Pro Leu Asn Pro
465                470              475              480

Ala Glu Lys Leu Arg His Leu Asn Glu Lys Arg Arg Phe His Lys Ile
              485              490              495

Ala Gly His Tyr Arg Gly Gln Cys His Ser Cys Cys Asn Arg Ala Arg
              500              505              510

Gln Glu Arg Leu Gln Arg Arg Glu Thr Gln Val Ala Arg Arg Ala
              515              520              525

Glu Pro Gln Arg His Thr Met Leu Cys Met Cys Cys Lys Cys Glu Ala
              530              535              540

Arg Ile Glu Leu Val Val Glu Ser Ser Ala Asp Asp Leu Arg Ala Phe
545                550              555              560

Gln Gln Leu Phe Leu Ser Thr Leu Ser Phe Val Cys Pro Trp Cys Ala
              565              570              575

Ser Gln Gln

<210> SEQ ID NO 11
<211> LENGTH: 489
<212> TYPE: DNA
<213> ORGANISM: Artificial Sequence
<220> FEATURE:
<223> OTHER INFORMATION: Nucleotide sequence of FLT3L (fms-like tyrosine
    kinase-3 ligand)

<400> SEQUENCE: 11
atcacccagg actgctcctt ccaacacagc cccatctcct ccgacttcgc tgtcaaaatc    60
cgtgagctgt ctgactacct gcttcaagat tacccagtca ccgtggcctc caacctgcag   120
gacgaggagc tctgcggggg cctctggcgg ctggtcctgg cacagcgctg gatggagcgg   180
ctcaagactg tcgctgggtc caagatgcaa ggcttgctgg agcgcgtgaa cacggagata   240

```
cactttgtca ccaaatgtgc ctttcagccc cccccagct gtcttcgctt cgtccagacc    300
aacatctccc gcctcctgca ggagacctcc gagcagctgg tggcgctgaa gccctggatc    360
actcgccaga acttctcccg gtgcctggag ctgcagtgtc agcccgactc ctcaaccctg    420 ccaccccat ggagtccccg gccctggag ccacagccc cgacagcccc gggcggcggc    480
agcggcgat                                                              489
```

```
<210> SEQ ID NO 12
<211> LENGTH: 163
<212> TYPE: PRT
<213> ORGANISM: Artificial Sequence
<220> FEATURE:
<223> OTHER INFORMATION: Amino acid sequence of FLT3L (fms-like tyrosine
      kinase-3 ligand)

<400> SEQUENCE: 12

Ile Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Gly Leu
        35                  40                  45

Trp Arg Leu Val Leu Ala Gln Arg Trp Met Glu Arg Leu Lys Thr Val
    50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
                85                  90                  95

Phe Val Gln Thr Asn Ile Ser Arg Leu Leu Gln Glu Thr Ser Glu Gln
            100                 105                 110

Leu Val Ala Leu Lys Pro Trp Ile Thr Arg Gln Asn Phe Ser Arg Cys
        115                 120                 125

Leu Glu Leu Gln Cys Gln Pro Asp Ser Ser Thr Leu Pro Pro Pro Trp
    130                 135                 140

Ser Pro Arg Pro Leu Glu Ala Thr Ala Pro Thr Ala Pro Gly Gly Gly
145                 150                 155                 160

Ser Gly Asp
```

```
<210> SEQ ID NO 13
<211> LENGTH: 69
<212> TYPE: DNA
<213> ORGANISM: Artificial Sequence
<220> FEATURE:
<223> OTHER INFORMATION: Signal peptide of tPA

<400> SEQUENCE: 13
atggatgcta tgaaacgggg cctgtgctgc gtgctgctcc tgtgcggcgc tgtgtttgtg    60
agccctagc                                                             69
```

```
<210> SEQ ID NO 14
<211> LENGTH: 23
<212> TYPE: PRT
<213> ORGANISM: Artificial Sequence
<220> FEATURE:
<223> OTHER INFORMATION: Signal peptide of tPA

<400> SEQUENCE: 14

Met Asp Ala Met Lys Arg Gly Leu Cys Cys Val Leu Leu Leu Cys Gly
```

```
1               5                  10                 15
Ala Val Phe Val Ser Pro Ser
            20
```

<210> SEQ ID NO 15
<211> LENGTH: 6085
<212> TYPE: DNA
<213> ORGANISM: Artificial Sequence
<220> FEATURE:
<223> OTHER INFORMATION: GX-188E

<400> SEQUENCE: 15

| | | | | | |
|---|---|---|---|---|---|
| acgcgttgac | attgattatt | gactagttat | taatagtaat | caattacggg | gtcattagtt | 60 |
| catagcccat | atatggagtt | ccgcgttaca | taacttacgg | taaatggccc | gcctggctga | 120 |
| ccgcccaacg | acccccgccc | attgacgtca | ataatgacgt | atgttcccat | agtaacgcca | 180 |
| atagggactt | tccattgacg | tcaatgggtg | gagtatttac | ggtaaactgc | ccacttggca | 240 |
| gtacatcaag | tgtatcatat | gccaagtacg | cccctattg | acgtcaatga | cggtaaatgg | 300 |
| cccgcctggc | attatgccca | gtacatgacc | ttatgggact | ttcctacttg | gcagtacatc | 360 |
| tacgtattag | tcatcgctat | taccatggtg | atgcggtttt | ggcagtacat | caatgggcgt | 420 |
| ggatagcggt | ttgactcacg | gggatttcca | agtctccacc | ccattgacgt | caatgggagt | 480 |
| ttgttttggc | accaaaatca | acgggacttt | ccaaaatgtc | gtaacaactc | cgccccattg | 540 |
| acgcaaatgg | gcggtaggcg | tgtacggtgg | gaggtctata | taagcagagc | tctctggcta | 600 |
| actagagaac | ccactgctta | ctggcttatc | gaaattaata | cgactcacta | tagggagacc | 660 |
| caagctggct | agcgtgagtt | tggggaccct | tgattgttct | ttcttttcg | ctattgtaaa | 720 |
| attcatgtta | tatggagggg | caaagttttt | cagggtgttg | tttagaacgg | gaagatgtcc | 780 |
| cttgtatcac | catggaccct | catgataatt | tgtttctttt | cactttctac | tctgttgaca | 840 |
| accattgtct | cctcttattt | tcttttcatt | ttctgtaact | ttttcgttaa | actttagctt | 900 |
| gcatttgtaa | cgaattttta | aattcacttt | tgtttatttg | tcagattgta | agtactttct | 960 |
| ctaatcactt | tttttcaag | gcaatcaggg | tatattatat | tgtacttcag | cacagtttta | 1020 |
| gagaacaatt | gttataatta | aatgataagg | tagaatattt | ctgcatataa | attctggctg | 1080 |
| gcgtggaaat | attcttattg | gtagaaacaa | ctacatcctg | gtcatcatcc | tgcctttctc | 1140 |
| tttatggtta | caatgatata | cactgtttga | gatgaggata | aaatactctg | agtccaaacc | 1200 |
| gggcccctct | gctaaccatg | ttcatgcctt | cttctttttc | ctacagctcc | tgggcaacgt | 1260 |
| gctggttatt | gtgctgtctc | atcattttgg | caaagaattg | taatacgact | cactataggg | 1320 |
| cgaattgaag | cttggtaccg | ccaccatgga | tgctatgaaa | cggggcctgt | gctgcgtgct | 1380 |
| gctcctgtgc | ggcgctgtgt | tgtgagccc | tagcatcacc | caggactgct | ccttccaaca | 1440 |
| cagccccatc | tcctccgact | cgctgtcaa | aatccgtgag | ctgtctgact | acctgcttca | 1500 |
| agattaccca | gtcaccgtgg | cctccaacct | gcaggacgag | gagctctgcg | ggggcctctg | 1560 |
| gcggctggtc | ctggcacagc | gctggatgga | gcggctcaag | actgtcgctg | gtccaagat | 1620 |
| gcaaggcttg | ctggagcgcg | tgaacacgga | gatacacttt | gtcaccaaat | gtgccttca | 1680 |
| gccccccccc | agctgtcttc | gcttcgtcca | gaccaacatc | tcccgcctcc | tgcaggagac | 1740 |
| ctccgagcag | ctggtggcgc | tgaagccctg | gatcactcgc | agaacttct | cccggtgcct | 1800 |
| ggagctgcag | tgtcagcccg | actcctcaac | cctgccaccc | ccatggagtc | cccggccct | 1860 |
| ggaggccaca | gccccgacag | cccgggcgg | cggcagcggc | gatgctagca | tgcaccagaa | 1920 |

| | | | | | |
|---|---|---|---|---|---|
| gagaaccgcc | atgttccagg | accctcagga | gagacctagg | aagctgcctc | acctgtgtac | 1980 |
| agagctccag | acaaccatcc | acgacatcat | cctggagtgc | gtgtactgta | agcagcagct | 2040 |
| gctgagaaga | gaggtgtacg | acttcgcctt | cagagacctg | tgcatcgtgt | acagagacgg | 2100 |
| caacccttac | gccgtgtgcg | ataagtgtct | gaagttctat | tccaaaatct | ccgaatatag | 2160 |
| gtacatgcac | ggcgacaccc | ctaccctgca | cgagtacatg | ctggacctcc | agcctgagac | 2220 |
| cacagacctg | tactgctacg | agcagctgaa | cgacagctct | gaggaagagg | acgagattga | 2280 |
| cggacctgct | ggccaggccg | agcctgacag | agcccactac | aatatcgtga | cattctgttg | 2340 |
| caaatgcgac | tccacactgg | acaagtgcct | gaagttctac | agcaagatct | ctgagtacag | 2400 |
| atactactgc | tactctgtgt | acggcaccac | actggagcag | cagtacaaca | agcctctgtg | 2460 |
| cgacctcctg | atccgctgca | tcaactgcca | aaagcctctg | tgcctgagg | agaagcagag | 2520 |
| acacctggac | aagaagcagc | ggttccacaa | catcagaggc | agatggaccg | gcaggtgcat | 2580 |
| gtcctgctgt | agatcctcca | gaaccagacg | ggagacccag | ctgcactaca | acatcgtgac | 2640 |
| cttctgctgc | aagtgcgact | ctaccctgag | actgtgcgtg | cagtctaccc | acgtggacat | 2700 |
| cagaacccctg | gaggacctgc | tgatgggcac | cctgggcatc | gtgtgcccta | tctgctctca | 2760 |
| gaagcctatg | gccaggttcg | aggacccctac | cagaagaccc | tacaagctgc | ctgacctgtg | 2820 |
| caccgagctg | aacacctctc | tgcaagacat | cgagatcacc | tgcgtgtact | gcaagaccgt | 2880 |
| gctggagctg | accgaggtgt | tcgagttcgc | cttcaaggac | ctgttcgtgg | tgtacagaga | 2940 |
| cagcatccct | cacgctgcct | gccacaagtg | catcgacttc | tattccagga | tcagggagct | 3000 |
| gcgctattac | tccgactctg | tgatgtacgg | ccccaaggcc | accctccagg | acatcgtgct | 3060 |
| gcacctggag | cctcagaacg | agatccccgt | ggacctgctg | tgccacgagc | agctgtctga | 3120 |
| ctctgaagag | gagaacgacg | agatcgacgg | cgtgaaccac | cagcacctgc | ctgccaggag | 3180 |
| agctgaaccc | cagcggcata | ccatgctgtg | tatgtgcttc | tactctagga | tcagagagct | 3240 |
| gaggtactac | tctgactctg | tgtacggcga | caccctggag | aagctgacca | acaccggcct | 3300 |
| gtacaacctg | ctgatccggt | gcctgaggtg | ccagaagcct | ctgaaccctg | ccgagaagct | 3360 |
| gagacacctg | aacgagaaga | gaagattcca | caagatcgct | ggccactaca | gaggccagtg | 3420 |
| ccactcttgc | tgcaacagag | ccagacagga | gagactccag | cggagaaggg | agacccaggt | 3480 |
| ggccagaaga | gccgagcctc | agagacacac | catgctgtgc | atgtgctgca | agtgcgaggc | 3540 |
| cagaatcgag | ctggtggtgg | agagctctgc | cgacgacctg | agagccttcc | agcagctgtt | 3600 |
| cctgtctacc | ctgagcttcg | tgtgcccttg | gtgcgcctct | cagcagtaat | ctagagtcgg | 3660 |
| ggcggccggc | cgcttcgagc | agacatgata | agatacattg | atgagtttgg | acaaaccaca | 3720 |
| actagaatgc | agtgaaaaaa | atgctttatt | tgtgaaattt | gtgatgctat | tgctttattt | 3780 |
| gtaaccatta | taagctgcaa | taaacaagtt | aacaacaaca | attgcattca | ttttatgttt | 3840 |
| caggttcagg | gggaggtgtg | ggaggttttt | taaagcaagt | aaaacctcta | caaatgtggt | 3900 |
| aaaatcgata | aggatctgaa | cgatggagcg | agaatgggc | ggaactgggc | ggagttaggg | 3960 |
| gcgggatggg | cggagttagg | ggcgggacta | tggttgctga | ctaattgaga | tgcatgcttt | 4020 |
| gcatacttct | gcctgctggg | gagcctgggg | actttccaca | cctggttgct | gactaattga | 4080 |
| gatgcatgct | ttgcatactt | ctgcctgctg | gggagcctgg | ggactttcca | caccctaact | 4140 |
| gacacacatt | ccacagcgga | tccgtcgact | tcagaagaac | tcgtcaagaa | ggcgatagaa | 4200 |
| ggcgatgcgc | cgcgaatcgg | gagcggcgat | accgtagagc | acgaggaagc | ggtcagccca | 4260 |
| ttcgccgcca | agctcttcag | caatatcacg | ggtagccaac | gctatgtcct | gatagcggtc | 4320 |

```
cgccacaccc agccggccac agtcgatgaa tccagaaaag cggccatttt ccaccatgat    4380
attcggcaag caggcatcgc catgggtcac gacgagatcc tcgccgtcgg gcatgctcgc    4440
cttgagcctg gcgaacagtt cggctggcgc gagcccctga tgctcttcgt ccagatcatc    4500
ctgatcgaca agaccggctt ccatccgagt acgtgctcgc tcgatgcgat gtttcgcttg    4560
gtggtcgaat gggcaggtag ccggatcaag cgtatgcagc cgccgcattg catcagccat    4620
gatggatact ttctcggcag gagcaaggtg agatgacagg agatcctgcc ccggcacttc    4680
gcccaatagc agccagtccc ttcccgcttc agtgacaacg tcgagcacag ctgcgcaagg    4740
aacgcccgtc gtggccagcc acgatagccg cgctgcctcg tcttgcagtt cattcagggc    4800
accggacagg tcggtcttga caaaaagaac cgggcgcccc tgcgctgaca gccggaacac    4860
ggcggcatca gagcagccga ttgtctgttg tgcccagtca tagccgaata gcctctccac    4920
ccaagcggcc ggagaacctg cgtgcaatcc atcttgttca atcatgcgaa acgatcctca    4980
tcctgtctct tgatcagatc ttgatcccct gcgccatcag atcctggcg caagaaagc    5040
catccagttt actttgcagg gcttcccaac cttaccagag ggcgccccag ctggcaattc    5100
cggttcgctt gctgtccata aaaccgccca gtctagctat cgccatgtaa gcccactgca    5160
agctacctgc tttctctttg cgcttgcgtt ttcccttgtc cagatagccc agtagctgac    5220
attcatccgg ggtcagcacc gtttctgcgg actggctttc tacgtgaaaa ggatctaggt    5280
gaagatcctt tttgataatc tcatgaccaa aatcccttaa cgtgagtttt cgttccactg    5340
agcgtcagac cccgtagaaa agatcaaagg atccttcttga gatccttttt ttctgcgcgt    5400
aatctgctgc ttgcaaacaa aaaaaccacc gctaccagcg gtggtttgtt tgccggatca    5460
agagctacca actcttttc cgaaggtaac tggcttcagc agagcgcaga taccaaatac    5520
tgttcttcta gtgtagccgt agttaggcca ccacttcaag aactctgtag caccgcctac    5580
atacctcgct ctgctaatcc tgttaccagt ggctgctgcc agtggcgata agtcgtgtct    5640
taccgggttg gactcaagac gatagttacc ggataaggcg cagcggtcgg gctgaacggg    5700
gggttcgtgc acacagccca gcttggagcg aacgacctac accgaactga gatacctaca    5760
gcgtgagcta tgagaaagcg ccacgcttcc cgaagggaga aaggcggaca ggtatccggt    5820
aagcggcagg gtcggaacag gagagcgcac gagggagctt ccaggggaa acgcccggta    5880
tctttatagt cctgtcgggt ttcgccacct ctgacttgag cgtcgatttt tgtgatgctc    5940
gtcagggggg cggagcctat ggaaaaacgc cagcaacgcg gccttttac ggttcctggc    6000
cttttgctgg ccttttgctc acatgttcgg gccaatcga cccgggcgac ggccagtgaa    6060
ttgtaccgat gtacgggcca gatat                                          6085
```

<210> SEQ ID NO 16
<211> LENGTH: 12
<212> TYPE: PRT
<213> ORGANISM: Artificial Sequence
<220> FEATURE:
<223> OTHER INFORMATION: alpha-1 helix of E7 protein of HPV16 (position 73-84)

<400> SEQUENCE: 16

His Val Asp Ile Arg Thr Leu Glu Asp Leu Leu Met
1               5                   10

<210> SEQ ID NO 17
<211> LENGTH: 8
<212> TYPE: PRT

```
<213> ORGANISM: Artificial Sequence
<220> FEATURE:
<223> OTHER INFORMATION: beta-2 sheet of E7 protein of HPV16 (position
      64-71)

<400> SEQUENCE: 17

Thr Leu Arg Leu Cys Val Gln Ser
1               5

<210> SEQ ID NO 18
<211> LENGTH: 11
<212> TYPE: PRT
<213> ORGANISM: Artificial Sequence
<220> FEATURE:
<223> OTHER INFORMATION: beta-1 sheet of E7 protein of HPV16 (position
      48-58)

<400> SEQUENCE: 18

Asp Arg Ala His Tyr Asn Ile Val Thr Phe Cys
1               5                   10

<210> SEQ ID NO 19
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91670.1 E6 Variant

<400> SEQUENCE: 19

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 20
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91673.1 E6 Variant

<400> SEQUENCE: 20

Met Phe Gln Asp Pro Gln Glu Arg Pro Arg Lys Leu Pro Gln Leu Cys
1               5                   10                  15
```

```
Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 21
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91669.1 E6 Variant

<400> SEQUENCE: 21

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Lys Asn Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 22
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91674.1 E6 Variant

<400> SEQUENCE: 22
```

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 23
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91680.1 E6 Variant

<400> SEQUENCE: 23

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 24
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91681.1

```
<400> SEQUENCE: 24

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 25
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91668.1 E6 Variant

<400> SEQUENCE: 25

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 26
<211> LENGTH: 151
<212> TYPE: PRT
<213> ORGANISM: Human papillomavirus 16
```

```
<220> FEATURE:
<221> NAME/KEY: MISC_FEATURE
<223> OTHER INFORMATION: AAA91658.1 E6 Variant

<400> SEQUENCE: 26

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 27
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91662.1 E6 Variant

<400> SEQUENCE: 27

Met Phe Gln Asp Pro Gln Glu Arg Pro Arg Lys Leu Pro Gln Leu Cys
1               5                   10                  15

Thr Glu Leu Gln Thr Thr Ile His Glu Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 28
```

```
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91667.1 E6 Variant

<400> SEQUENCE: 28

Met Phe Gln Asp Pro Gln Glu Arg Pro Arg Lys Leu Pro Gln Leu Cys
1               5                   10                  15

Thr Glu Leu Gln Thr Thr Ile His Glu Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 29
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91676.1 E6 Variant

<400> SEQUENCE: 29

Met Phe Gln Asp Pro Gln Glu Arg Pro Arg Lys Leu Pro Gln Leu Cys
1               5                   10                  15

Thr Glu Leu Gln Thr Thr Ile His Glu Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

```
<210> SEQ ID NO 30
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91671.1 E6 Variant

<400> SEQUENCE: 30

Met Phe Gln Asp Pro Gln Glu Arg Pro Arg Lys Leu Pro Gln Leu Cys
1               5                   10                  15

Thr Glu Leu Gln Thr Thr Ile His Glu Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 31
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91656.1 E6 Variant

<400> SEQUENCE: 31

Met Phe Gln Asp Pro Gln Glu Arg Pro Gly Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140
```

Thr Arg Arg Glu Thr Gln Leu
145                 150

<210> SEQ ID NO 32
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91682.1 E6 Variant

<400> SEQUENCE: 32

Met Phe Gln Asp Pro Gln Glu Arg Pro Gly Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 33
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91657.1 E6 Variant

<400> SEQUENCE: 33

Met Phe Gln Asp Pro Gln Glu Arg Pro Gly Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Arg Ser Arg
        130                 135                 140

Thr Arg Arg Glu Thr Gln Leu
145                 150

<210> SEQ ID NO 34
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91660.1 E6 Variant

<400> SEQUENCE: 34

Met Phe Gln Asp Pro Gln Glu Arg Pro Gly Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 35
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91677.1 E6 Variant

<400> SEQUENCE: 35

Met Phe Gln Asp Pro Gln Glu Arg Pro Thr Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 36
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91678.1 E6 Variant

<400> SEQUENCE: 36

Met Phe Gln Asp Pro Gln Glu Arg Pro Thr Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 37
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91672.1 E6 Variant

<400> SEQUENCE: 37

Met Phe Gln Asp Pro Gln Glu Arg Pro Thr Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

```
Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 38
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91661.1 E6 Variant

<400> SEQUENCE: 38

Met Phe Gln Asp Pro Gln Glu Arg Pro Thr Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 39
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91664.1 E6 Variant

<400> SEQUENCE: 39

Met Phe Gln Asp Pro Gln Glu Arg Pro Ile Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80
```

```
Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

<210> SEQ ID NO 40
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91675.1 E6 Variant

<400> SEQUENCE: 40

```
Met Phe Gln Asp Pro Gln Glu Arg Pro Ile Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

<210> SEQ ID NO 41
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91665.1 E6 Variant

<400> SEQUENCE: 41

```
Met Phe Gln Asp Pro Gln Glu Arg Pro Ile Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60
```

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 42
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91663.1 E6 Variant

<400> SEQUENCE: 42

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 43
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91659.1 E6 Variant

<400> SEQUENCE: 43

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

-continued

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg Tyr Tyr Cys
 65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 44
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91654.1 E6 Variant

<400> SEQUENCE: 44

Met Phe Gln Asp Pro Gln Glu Arg Pro Arg Lys Leu Pro His Leu Cys
 1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
 65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 45
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91666.1 E6 Variant

<400> SEQUENCE: 45

Met Phe Gln Asp Pro Gln Glu Arg Pro Arg Lys Leu Pro His Leu Cys
 1               5                   10                  15

Thr Glu Leu Gln Thr Thr Ile His Asp Ile Ile Leu Glu Cys Val Tyr
            20                  25                  30

```
Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
                    100                 105                 110

Glu Glu Lys Gln Arg His Leu Asp Lys Lys Gln Arg Phe His Asn Ile
                115                 120                 125

Arg Gly Arg Trp Thr Gly Arg Cys Met Ser Cys Cys Arg Ser Ser Arg
            130                 135                 140

Thr Arg Arg Glu Thr Gln Leu
145                 150

<210> SEQ ID NO 46
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91679.1 E6 Variant

<400> SEQUENCE: 46

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
                    100                 105                 110

Glu Glu Lys Gln Arg His Leu Asp Lys Lys Gln Arg Phe His Asn Ile
                115                 120                 125

Arg Gly Arg Trp Thr Gly Arg Cys Met Ser Cys Cys Arg Ser Ser Arg
            130                 135                 140

Thr Arg Arg Glu Thr Gln Leu
145                 150

<210> SEQ ID NO 47
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91655.1 E6 Variant

<400> SEQUENCE: 47

Met Phe Gln Asp Pro Gln Glu Arg Pro Arg Lys Leu Pro His Leu Cys
1               5                   10                  15
```

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Arg Ser Ser Arg
        130                 135                 140

Thr Arg Arg Glu Thr Gln Leu
145                 150

<210> SEQ ID NO 48
<211> LENGTH: 147
<212> TYPE: PRT
<213> ORGANISM: Human papillomavirus 18
<220> FEATURE:
<221> NAME/KEY: MISC_FEATURE
<223> OTHER INFORMATION: AHZ96678.1 E6 Variant

<400> SEQUENCE: 48

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg Tyr
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
            115                 120                 125

Lys Ile Ala Gly His Tyr Arg Gly Gln Cys His Ser Cys Cys Asn Arg
        130                 135                 140

Ala Arg Gln
145

<210> SEQ ID NO 49
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ABP99784.1 E6 Variant

<400> SEQUENCE: 49

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg Tyr
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Lys Ile Ala Gly His Tyr Arg Gly Gln Cys His Ser Cys Cys Asn Arg
        130                 135                 140

Ala Arg Gln Glu Arg Leu Gln Arg Arg Arg Glu Thr Gln Val
145                 150                 155

<210> SEQ ID NO 50
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: CAB53096.1 E6 Variant

<400> SEQUENCE: 50

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Lys Ile Ala Gly His Tyr Arg Gly Gln Cys His Ser Cys Cys Asn Arg
        130                 135                 140

Ala Arg Gln Glu Arg Leu Gln Arg Arg Arg Glu Thr Gln Val
145                 150                 155

<210> SEQ ID NO 51
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: AGU90327.1 E6 Variant

<400> SEQUENCE: 51

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Lys Ile Ala Gly His Tyr Arg Gly Gln Cys His Ser Cys Cys Asn Gln
130                 135                 140

Ala Arg Gln Glu Arg Leu Gln Arg Arg Glu Thr Gln Val
145                 150                 155

<210> SEQ ID NO 52
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ADC35660.1 E6 Variant

<400> SEQUENCE: 52

Met Ala Arg Phe Glu Asp Pro Thr Arg Arg Pro Tyr Lys Val Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
130                 135                 140

Ala Arg Gln Glu Arg Leu Gln Arg Arg Glu Thr Gln Val
145                 150                 155

<210> SEQ ID NO 53
<211> LENGTH: 158
<212> TYPE: PRT

```
<213> ORGANISM: Human papillomavirus 18
<220> FEATURE:
<221> NAME/KEY: MISC_FEATURE
<223> OTHER INFORMATION: AHZ96677.1 E6 Variant

<400> SEQUENCE: 53

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
                35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
                115                 120                 125

Asn Ile Ala Gly His Tyr Arg Gly Gln Cys His Ser Cys Cys Asn Arg
                130                 135                 140

Ala Arg Gln Glu Arg Leu Gln Arg His Arg Glu Thr Gln Val
145                 150                 155

<210> SEQ ID NO 54
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ABP99736.1 E6 Variant

<400> SEQUENCE: 54

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Gly Val Phe Glu Phe Ala
                35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
                115                 120                 125

Asn Ile Ala Gly His Tyr Arg Gly Gln Cys His Ser Cys Cys Asn Arg
                130                 135                 140

Ala Arg Gln Glu Arg Leu Gln Arg Arg Arg Glu Thr Gln Val
145                 150                 155
```

<210> SEQ ID NO 55
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ABP99704.1 E6 Variant

<400> SEQUENCE: 55

```
Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly Arg Tyr Arg Gly Gln Cys His Ser Cys Cys Asn Arg
    130                 135                 140

Ala Arg Gln Glu Arg Leu Gln Arg Arg Glu Thr Gln Val
145                 150                 155
```

<210> SEQ ID NO 56
<211> LENGTH: 90
<212> TYPE: PRT
<213> ORGANISM: Human papillomavirus 16
<220> FEATURE:
<221> NAME/KEY: MISC_FEATURE
<223> OTHER INFORMATION: ABL96587.1 E7 Variant

<400> SEQUENCE: 56

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Arg Ser Thr His Val Asp Ile Arg Thr Leu Glu
65                  70                  75                  80

Asp Leu Leu Met Gly Thr Leu Gly Ile Val
                85                  90
```

<210> SEQ ID NO 57
<211> LENGTH: 90
<212> TYPE: PRT
<213> ORGANISM: Human papillomavirus 16
<220> FEATURE:
<221> NAME/KEY: MISC_FEATURE
<223> OTHER INFORMATION: ABL96591.1 E7 Variant

<400> SEQUENCE: 57

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Cys Thr Leu Glu
65                  70                  75                  80

Asp Leu Leu Met Gly Thr Leu Gly Ile Val
                85                  90

<210> SEQ ID NO 58
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19726.1 E7 Variant

<400> SEQUENCE: 58

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Val Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 59
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19722.1 E7 Variant

<400> SEQUENCE: 59

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Val Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 60
```

```
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19752.1 E7 Variant

<400> SEQUENCE: 60

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Thr Asp
        35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 61
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19732.1 E7 Variant

<400> SEQUENCE: 61

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Lys Asp Ser Ser
            20                  25                  30

Glu Glu Glu Asp Glu Val Asp Gly Pro Ala Gly Gln Ala Glu Pro Asp
        35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 62
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19762.1 E7 Variant

<400> SEQUENCE: 62

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Arg Cys Lys Cys Asp Ser Thr
50                  55                  60
```

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
            85                  90

<210> SEQ ID NO 63
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19668.1 E7 Variant

<400> SEQUENCE: 63

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Met Leu Glu
65                  70                  75                  80

Asp Leu Leu Met Gly Thr Leu Gly Ile Val Cys Pro
            85                  90

<210> SEQ ID NO 64
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19664.1 E7 Variant

<400> SEQUENCE: 64

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Ser Thr Leu Gly Ile Val Cys Pro
            85                  90

<210> SEQ ID NO 65
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19766.1 E7 Variant

<400> SEQUENCE: 65

Met His Gly Asp Thr Pro Thr Leu His Glu Tyr Met Leu Asp Leu Gln
1               5                   10                  15

Pro Glu Thr Asn Asp Leu Tyr Cys Tyr Glu Gln Leu Asn Asp Ser Ser

```
                    20                  25                  30

Glu Glu Glu Asp Glu Ile Asp Gly Pro Ala Gly Gln Ala Glu Pro Asp
                35                  40                  45

Arg Ala His Tyr Asn Ile Val Thr Phe Cys Cys Lys Cys Asp Phe Thr
            50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 66
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19756.1 E7 Variant

<400> SEQUENCE: 66

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Lys Asp Gly Pro Ala Gly Gln Ala Glu Pro Asp
                35                  40                  45

Arg Ala His Tyr Asn Ile Val Thr Phe Cys Cys Lys Cys Asp Ser Thr
            50                  55                  60

Leu Arg Leu Cys Val Gln Ser Thr His Val Asp Ile Arg Thr Leu Glu
65                  70                  75                  80

Asp Leu Leu Ile Gly Thr Leu Gly Ile Val Cys Pro
                85                  90

<210> SEQ ID NO 67
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19680.1 E7 Variant

<400> SEQUENCE: 67

Met His Gly Asp Thr Pro Thr Leu His Glu Tyr Lys Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Thr Gly Gln Ala Glu Pro Asp
                35                  40                  45

Arg Ala His Tyr Asn Ile Val Thr Phe Cys Cys Lys Cys Asp Ser Thr
            50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 68
<211> LENGTH: 92
<212> TYPE: PRT
<213> ORGANISM: Human papillomavirus 16
<220> FEATURE:
<221> NAME/KEY: MISC_FEATURE
```

<223> OTHER INFORMATION: AFJ19772.1 E7 Variant

<400> SEQUENCE: 68

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Asp Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Asp Thr Leu Gly Ile Val Cys Pro
                85                  90

<210> SEQ ID NO 69
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19696.1 E7 Variant

<400> SEQUENCE: 69

Met His Gly Asp Thr Pro Thr Leu His Glu Tyr Lys Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Lys Gly Thr Leu Gly Ile Val Cys Pro
                85                  90

<210> SEQ ID NO 70
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19690.1 E7 Variant

<400> SEQUENCE: 70

Met His Gly Asp Thr Pro Thr Leu His Glu Tyr Met Leu Val Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Gly Leu Leu Met Gly Thr Leu Gly Ile Val Cys Pro
                85                  90

```
<210> SEQ ID NO 71
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19712.1 E7 Variant

<400> SEQUENCE: 71

Met His Gly Asp Thr Pro Thr Leu His Glu Tyr Lys Leu Asp Leu Gln
1               5                   10                  15

Pro Glu Thr Thr Asp Leu His Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Ile Thr Phe Cys Cys Arg Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 72
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AGO04504.1 E7 Variant

<400> SEQUENCE: 72

Met His Gly Asp Thr Pro Thr Leu His Glu Tyr Met Leu Gly Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Met Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Ala Leu Gly Ile Val Cys Pro
                85                  90

<210> SEQ ID NO 73
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19770.1 E7 Variant

<400> SEQUENCE: 73

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Tyr Asp Ser Ser
            20                  25                  30

Glu Glu Glu Asp Glu Ile Asp Gly Pro Ala Gly Gln Ala Glu Pro Asp
            35                  40                  45
```

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Gln Thr Leu Glu
65                  70                  75                  80

Asp Leu Leu Met Gly Ala Leu Gly Ile Val Cys Pro
                85                  90

<210> SEQ ID NO 74
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19520.2 E7 Variant

<400> SEQUENCE: 74

Met His Gly Asp Thr Pro Thr Leu His Lys Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Tyr Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Ser Thr Leu Gly Ile Val Cys Pro
                85                  90

<210> SEQ ID NO 75
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19708.1 E7 Variant

<400> SEQUENCE: 75

Met His Gly Asp Thr Pro Lys Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Gln Ala Gly Gln Ala Lys Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Gly Leu Leu Met Gly Thr Leu Gly Ile Val Cys Pro
                85                  90

<210> SEQ ID NO 76
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19674.1 E7 Variant

<400> SEQUENCE: 76

Met His Gly Asp Thr Pro Thr Leu His Glu Tyr Met Leu Asp Leu Gln

```
                1               5                  10                 15
        Pro Glu Thr Thr Asp Leu Tyr Cys Tyr Glu Gln Leu Asn Asp Asn Ser
                        20                  25                  30

Glu Glu Asp His Glu Ile Asp Gly Pro Asp Gly Gln Ala Glu Pro Asp
                        35                  40                  45

Arg Ala His Tyr Asn Ile Val Thr Phe Cys Cys Lys Cys Asp Ser Thr
                    50                  55                  60

Leu Arg Leu Cys Val Gln Ser Thr His Val Asp Ile Arg Thr Leu Glu
        65                  70                  75                  80

Asp Leu Leu Met Gly Thr Leu Gly Ile Val Cys Pro
                        85                  90
```

<210> SEQ ID NO 77
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AGO04498.1 E7 Variant

<400> SEQUENCE: 77

```
        Met His Gly Asp Thr Ser Thr Leu His Glu Tyr Met Leu Asp Leu Gln
        1               5                   10                  15

Pro Glu Thr Thr Asp Leu Tyr Cys Tyr Glu Gln Leu Asn Asp Ser Ser
                        20                  25                  30

Glu Glu Glu Asp Glu Ile Asp Gly Pro Ala Gly Gln Ala Glu Pro Asp
                        35                  40                  45

Arg Ala His Tyr Asn Asn Val Thr Phe Cys Cys Lys Cys Asp Ser Thr
                    50                  55                  60

Leu Arg Leu Cys Val Gln Ser Thr Leu Val Asp Ile Arg Thr Leu Glu
        65                  70                  75                  80

Asp Met Leu Met Gly Thr Leu Gly Ile Val Ser Pro
                        85                  90
```

<210> SEQ ID NO 78
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AGO04496.1 E7 Variant

<400> SEQUENCE: 78

```
        Met His Gly Asp Thr Pro Thr Leu His Glu Tyr Val Leu Gly Leu Gln
        1               5                   10                  15

Pro Glu Thr Thr Asp Leu Tyr Cys Tyr Glu Gln Leu Asn Asp Ser Ser
                        20                  25                  30

Glu Glu Glu Asp Glu Ile Asp Gly Pro Ala Gly Gln Ala Glu Pro Val
                        35                  40                  45

Arg Ala His Tyr Asn Ile Val Thr Phe Cys Cys Lys Cys Asp Ser Thr
                    50                  55                  60

Leu Arg Phe Cys Val Gln Ser Thr Arg Leu Asp Ile Arg Thr Leu Glu
        65                  70                  75                  80

Asp Leu Leu Met Gly Thr Leu Gly Ile Val Cys Pro
                        85                  90
```

<210> SEQ ID NO 79
<211> LENGTH: 92
<212> TYPE: PRT

<213> ORGANISM: Human papillomavirus 16
<220> FEATURE:
<221> NAME/KEY: MISC_FEATURE
<223> OTHER INFORMATION: AFJ19684.1 E7 Variant

<400> SEQUENCE: 79

Met His Gly Asp Thr Pro Thr Leu His Glu Tyr Lys Leu Asp Leu Gln
1               5                   10                  15

Pro Glu Thr Thr Asp Leu Tyr Cys Tyr Glu His Leu Asn Asp Ser Ser
                20                  25                  30

Glu Glu Glu Asp Glu Ile Asp Cys Pro Ala Gly Gln Ala Glu Pro Asp
            35                  40                  45

Arg Ala His Tyr Lys Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Ile Leu Gly Ile Val Cys Pro
                85                  90

<210> SEQ ID NO 80
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19678.1 E7 Variant

<400> SEQUENCE: 80

Met His Gly Asp Thr Pro Thr Leu His Glu Tyr Lys Leu Asp Leu Gln
1               5                   10                  15

Pro Glu Thr Thr Asp Leu Cys Cys Tyr Glu Gln Leu Asn Asp Ser Ser
                20                  25                  30

Glu Glu Glu Asp Glu Ile Asp Gly Pro Thr Gly Gln Ala Glu Pro Asp
            35                  40                  45

Arg Ala His Tyr Thr Ile Val Thr Phe Cys Cys Met Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 81
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19698.1 E7 Variant

<400> SEQUENCE: 81

Met His Gly Asp Thr Pro Thr Leu His Glu Tyr Lys Leu Asp Leu Gln
1               5                   10                  15

Pro Glu Thr Thr Asp Leu Tyr Cys Tyr Glu Gln Leu Asn His Ser Ser
                20                  25                  30

Glu Gly Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Pro Arg Leu Cys Val Gln Ser Thr His Val Asp Ile Arg Thr Leu Glu
65                  70                  75                  80

Asp Leu Leu Met Asp Thr Leu Gly Ile Val Cys Pro
            85                  90

<210> SEQ ID NO 82
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19746.1 E7 Variant

<400> SEQUENCE: 82

Met His Gly Asp Thr Pro Thr Leu His Glu Tyr Lys Leu Asp Leu Gln
1               5                   10                  15

Pro Glu Thr Thr Asp Leu Tyr Cys Asp Glu Gln Leu Asn His Ser Ser
            20                  25                  30

Glu Gly Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Pro Arg Leu Cys Val Gln Ser Thr His Val Asp Ile Arg Thr Leu Glu
65                  70                  75                  80

Asp Leu Leu Met Gly Thr Leu Gly Ile Val Cys Pro
            85                  90

<210> SEQ ID NO 83
<211> LENGTH: 93
<212> TYPE: PRT
<213> ORGANISM: Human papillomavirus 16
<220> FEATURE:
<221> NAME/KEY: MISC_FEATURE
<223> OTHER INFORMATION: AAF13395.1 E7 Variant

<400> SEQUENCE: 83

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Phe Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile
            85                  90

<210> SEQ ID NO 84
<211> LENGTH: 95
<212> TYPE: PRT
<213> ORGANISM: Human papillomavirus 16
<220> FEATURE:
<221> NAME/KEY: MISC_FEATURE
<223> OTHER INFORMATION: AFU06654.1 E7 Variant

<400> SEQUENCE: 84

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

```
Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser
                85                  90                  95

<210> SEQ ID NO 85
<211> LENGTH: 95
<212> TYPE: PRT
<213> ORGANISM: Human papillomavirus 16
<220> FEATURE:
<221> NAME/KEY: MISC_FEATURE
<223> OTHER INFORMATION: AFU06650.1 E7 Variant

<400> SEQUENCE: 85

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Phe Asn Asp Ser Ser
            20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser
                85                  90                  95

<210> SEQ ID NO 86
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: AAB70738.1 E7 Variant

<400> SEQUENCE: 86

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Phe Asn Asp Ser Ser
            20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 87
<211> LENGTH: 98
<212> TYPE: PRT
<213> ORGANISM: Human papillomavirus 16
<220> FEATURE:
<221> NAME/KEY: MISC_FEATURE
```

<223> OTHER INFORMATION: ACN22555.1 E7 Variant

<400> SEQUENCE: 87

Met His Gly Asp Thr Pro Thr Leu His Glu Tyr Met Leu Asp Val Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 88
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ABK32510.1 E7 Variant

<400> SEQUENCE: 88

Met His Gly Asp Thr Pro Thr Leu His Glu Tyr Met Leu Asp Leu Gln
1               5                   10                  15

Pro Glu Thr Ser Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 89
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ABC54573.1 E7 Variant

<400> SEQUENCE: 89

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Ala Leu Glu 65                  70                  75                  80

Asp Leu Leu Met Gly Thr Leu Gly Ile Val Cys Pro Ile Cys Ser Gln
                85                  90                  95

Lys Pro

<210> SEQ ID NO 90
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ACN22554.1 E7 Variant

<400> SEQUENCE: 90

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Arg Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 91
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ABK32511.1 E7 Variant

<400> SEQUENCE: 91

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Lys Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Ser Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 92
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ACQ90216.1 E7 Variant

<400> SEQUENCE: 92

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Arg Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 93
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ADY75576.1 E7 Variant

<400> SEQUENCE: 93

Met His Gly Asp Thr Pro Thr Leu His Glu Tyr Met Leu Asp Leu Gln
1               5                   10                  15

Pro Glu Thr Asn Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Phe Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 94
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: AAM03025.1 E7 Variant

<400> SEQUENCE: 94

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Cys Thr Leu Glu
65                  70                  75                  80

Asp Leu Leu Met Gly Thr Leu Gly Ile Val Cys Pro Ile Cys Ser Gln 85                  90                  95

Lys Pro

<210> SEQ ID NO 95
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: AAL96634.1 E7 Variant

<400> SEQUENCE: 95

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Trp Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 96
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: ABP99785.1 E7 Variant

<400> SEQUENCE: 96

Met Tyr Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Ser Thr Leu Ser Phe
                85                  90                  95

Val Cys Pro Trp Cys Ala Ser Gln Gln
            100                 105

<210> SEQ ID NO 97
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: AGU90416.1 E7 Variant

<400> SEQUENCE: 97

Met Tyr Gly Pro Lys Ala Thr Leu Gln Asp Ile Val Leu His Leu Glu

```
                1               5                  10                 15
    Pro Gln Asn Glu Ile Pro Val Asp Leu Leu Cys His Glu Gln Leu Ser
                        20                  25                  30

Asp Ser Glu Glu Glu Asn Asp Glu Ile Asp Gly Val Asn His Gln His
                        35                  40                  45

Leu Pro Ala Arg Arg Ala Glu Pro Gln Arg His Thr Met Leu Cys Met
            50                  55                  60

Cys Cys Lys Cys Glu Ala Arg Ile Glu Leu Val Val Glu Ser Ser Ala
    65                  70                  75                  80

Asp Asp Leu Arg Ala Phe Gln Gln Leu Phe Leu Asn Thr Leu Ser Phe
                        85                  90                  95

Val Cys Pro Trp Cys Ala Ser Gln Gln
                    100                 105
```

<210> SEQ ID NO 98
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: AGU90384.1 E7 Variant

<400> SEQUENCE: 98

```
    Met Tyr Gly Pro Lys Ala Thr Leu Gln Asp Ile Val Leu His Leu Glu
    1               5                   10                  15

Pro Gln Asn Asp Ile Pro Val Asp Leu Leu Cys His Glu Gln Leu Ser
                        20                  25                  30

Asp Ser Glu Glu Glu Asn Asp Glu Ile Asp Gly Val Asn His Gln His
                        35                  40                  45

Leu Pro Ala Arg Arg Ala Glu Pro Gln Arg His Thr Met Leu Cys Met
            50                  55                  60

Cys Cys Lys Cys Glu Ala Arg Ile Glu Leu Val Val Glu Ser Ser Ala
    65                  70                  75                  80

Asp Asp Leu Arg Ala Phe Gln Gln Leu Phe Leu Ser Thr Leu Ser Phe
                        85                  90                  95

Val Cys Pro Trp Cys Ala Ser Gln Gln
                    100                 105
```

<210> SEQ ID NO 99
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: CAB53097.1 E7 Variant

<400> SEQUENCE: 99

```
    Met His Gly Pro Lys Ala Thr Leu Gln Asp Ile Val Leu His Leu Glu
    1               5                   10                  15

Pro Gln Asn Glu Ile Pro Val Asp Leu Leu Cys His Glu Gln Leu Ser
                        20                  25                  30

Asp Ser Glu Glu Glu Asn Asp Glu Ile Asp Gly Val Asn His Gln His
                        35                  40                  45

Leu Pro Ala Arg Arg Ala Glu Pro Gln Arg His Thr Met Leu Cys Met
            50                  55                  60

Cys Cys Lys Cys Glu Ala Arg Ile Glu Leu Val Val Glu Ser Ser Ala
    65                  70                  75                  80

Asp Asp Leu Arg Ala Phe Gln Gln Leu Phe Leu Lys Thr Leu Ser Phe
```

Val Cys Pro Trp Cys Ala Ser Gln Gln
            100                 105

<210> SEQ ID NO 100
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: P06788.2 E7 Variant

<400> SEQUENCE: 100

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 101
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: CAB53098.1 E7 Variant

<400> SEQUENCE: 101

Met His Gly Pro Lys Ala Thr Leu Gln Asn Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Lys Thr Leu Ser Phe
                85                  90                  95

Val Cys Pro Trp Cys Ala Ser Gln Gln
            100                 105

<210> SEQ ID NO 102
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: CAB53099.1 E7 Variant

<400> SEQUENCE: 102

Met His Gly Pro Lys Ala Thr Leu Gln Asp Ile Val Leu His Leu Glu
1               5                   10                  15

Pro Gln Asn Glu Ile Pro Val Gly Leu Leu Cys His Glu Gln Leu Ser
            20                  25                  30

Asp Ser Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Lys Thr Leu Ser Phe
                85                  90                  95

Val Cys Pro Trp Cys Ala Ser Gln Gln
            100                 105

<210> SEQ ID NO 103
<211> LENGTH: 145
<212> TYPE: PRT
<213> ORGANISM: Human papillomavirus 18
<220> FEATURE:
<221> NAME/KEY: MISC_FEATURE
<223> OTHER INFORMATION: AGM34425.1 E6 Variant

<400> SEQUENCE: 103

Leu Pro Asp Leu Cys Thr Glu Leu Asn Thr Ser Leu Gln Asp Ile Glu
1               5                   10                  15

Ile Thr Cys Val Tyr Cys Lys Thr Val Leu Glu Leu Thr Glu Val Phe
            20                  25                  30

Glu Phe Ala Phe Lys Asp Leu Phe Val Val Tyr Arg Asp Ser Ile Pro
        35                  40                  45

His Ala Ala Cys His Lys Cys Ile Asp Phe Tyr Ser Arg Ile Arg Glu
    50                  55                  60

Leu Arg Tyr Tyr Ser Asp Ser Val Tyr Gly Asp Thr Leu Glu Lys Leu
65                  70                  75                  80

Thr Asn Thr Gly Leu Tyr Asn Leu Leu Ile Arg Cys Leu Arg Cys Gln
                85                  90                  95

Lys Pro Leu Asn Pro Ala Glu Lys Leu Arg His Leu Asn Glu Lys Arg
            100                 105                 110

Arg Phe His Lys Ile Ala Gly His Tyr Arg Gly Gln Cys His Ser Cys
        115                 120                 125

Cys Asn Arg Ala Arg Gln Glu Arg Leu Gln Arg Arg Glu Thr Gln
    130                 135                 140

Val
145

<210> SEQ ID NO 104
<211> LENGTH: 145
<212> TYPE: PRT
<213> ORGANISM: Human papillomavirus 18
<220> FEATURE:
<221> NAME/KEY: MISC_FEATURE
<223> OTHER INFORMATION: AGM34424.1 E6 Variant

<400> SEQUENCE: 104

Leu Pro Asp Leu Cys Thr Glu Leu Asn Thr Ser Leu Gln Asp Ile Glu
1               5                   10                  15

Ile Thr Cys Val Tyr Cys Lys Thr Val Leu Glu Leu Thr Glu Val Phe
            20                  25                  30

```
Glu Phe Ala Phe Lys Asp Leu Phe Val Val Tyr Arg Asp Ser Ile Pro
         35                  40                  45
His Ala Ala Cys His Lys Cys Ile Asp Phe Tyr Ser Arg Ile Arg Glu
 50                  55                  60
Leu Arg His Tyr Ser Asp Ser Val Tyr Gly Asp Thr Leu Glu Lys Leu
 65                  70                  75                  80
Thr Asn Thr Gly Leu Tyr Asn Leu Leu Ile Arg Cys Leu Arg Cys Gln
                 85                  90                  95
Lys Pro Leu Asn Pro Ala Glu Lys Leu Arg His Leu Asn Glu Lys Arg
             100                 105                 110
Arg Phe His Asn Ile Ala Gly His Tyr Arg Gly Gln Cys His Ser Cys
             115                 120                 125
Cys Asn Arg Ala Arg Gln Glu Arg Leu Gln Arg Arg Glu Thr Gln
         130                 135                 140
Val
145

<210> SEQ ID NO 105
<211> LENGTH: 6085
<212> TYPE: DNA
<213> ORGANISM: Artificial Sequence
<220> FEATURE:
<223> OTHER INFORMATION: C-1 mutant
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2186)
<223> OTHER INFORMATION: 16E6N (H21Q)
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2187)..(2381)
<223> OTHER INFORMATION: 16E7N
<220> FEATURE:
<221> NAME/KEY: misc_feature
<222> LOCATION: (2382)..(2645)
<223> OTHER INFORMATION: 16E6C (Y85H, V90L)
<220> FEATURE:
<221> NAME/KEY: misc_feature
<222> LOCATION: (2646)..(2789)
<223> OTHER INFORMATION: 16E7C
<220> FEATURE:
<221> NAME/KEY: misc_feature
<222> LOCATION: (2790)..(3671)
<223> OTHER INFORMATION: 18E6/E7

<400> SEQUENCE: 105
taccgatgta cgggccagat atacgcgttg acattgatta ttgactagtt attaatagta      60
atcaattacg gggtcattag ttcatagccc atatatggag ttccgcgtta cataacttac     120
ggtaaatggc ccgcctggct gaccgcccaa cgacccccgc ccattgacgt caataatgac     180
gtatgttccc atagtaacgc caatagggac tttccattga cgtcaatggg tggagtattt     240
acggtaaact gcccacttgg cagtacatca agtgtatcat atgccaagta cgccccctat     300
tgacgtcaat gacggtaaat ggcccgcctg gcattatgcc cagtacatga cctatatggga   360
```

```
ctttcctact tggcagtaca tctacgtatt agtcatcgct attaccatgg tgatgcggtt    420
ttggcagtac atcaatgggc gtggatagcg gtttgactca cggggatttc caagtctcca    480
ccccattgac gtcaatggga gtttgttttg gcaccaaaat caacgggact ttccaaaatg    540
tcgtaacaac tccgcccat tgacgcaaat gggcggtagg cgtgtacggt gggaggtcta    600
tataagcaga gctctctggc taactagaga acccactgct tactggctta tcgaaattaa    660
tacgactcac tatagggaga cccaagctgg ctagcgtgag tttggggacc cttgattgtt    720
ctttcttttt cgctattgta aaattcatgt tatatggagg gggcaaagtt ttcagggtgt    780
tgtttagaac gggaagatgt cccttgtatc accatggacc ctcatgataa ttttgtttct    840
ttcactttct actctgttga caaccattgt ctcctcttat tttcttttca ttttctgtaa    900 cttttcgtt aaactttagc ttgcatttgt aacgaatttt taaattcact tttgtttatt    960
tgtcagattg taagtacttt ctctaatcac ttttttttca aggcaatcag ggtatattat   1020
attgtacttc agcacagttt tagagaacaa ttgttataat taaatgataa ggtagaatat   1080
ttctgcatat aaattctggc tggcgtggaa atattcttat tggtagaaac aactacatcc   1140
tggtcatcat cctgcctttc tctttatggt tacaatgata tacactgttt gagatgagga   1200
taaaatactc tgagtccaaa ccgggcccct ctgctaacca tgttcatgcc ttcttctttt   1260
tcctacagct cctgggcaac gtgctggtta ttgtgctgtc tcatcatttt ggcaaagaat   1320
tgtaatacga ctcactatag gcgaattga agcttggtac cgccaccatg gatgctatga   1380 aacgggcct gtgctgcgtg ctgctcctgt gcggcgctgt gtttgtgagc cctagcatca   1440
cccaggactc ctccttccaa cacagcccca tctcctccga cttcgctgtc aaaatccgtg   1500
agctgtctga ctacctgctt caagattacc cagtcaccgt ggcctccaac ctgcaggacg   1560
aggagctctg cggggcctc tggcggctgg tcctggcaca cgctggatg gagcggctca   1620 agactgtcgc tgggtccaag atgcaaggct tgctggagcg cgtgaacacg gagatacact   1680
ttgtcaccaa atgtgccttt cagccccccc ccagctgtct tcgcttcgtc cagaccaaca   1740
tctcccgcct cctgcaggag acctccgagc agctggtggc gctgaagccc tggatcactc   1800
gccagaactt ctccccggtgc ctggagctgc agtgtcagcc cgactcctca acccctgccac   1860 ccccatggag tccccggccc ctggaggcca cagccccgac agccccgggc ggcggcagcg   1920
gcgatgctag catgcaccag aagagaaccg ccatgttcca ggaccctcag gagagaccta   1980
ggaagctgcc tcagctgtgt acagagctcc agacaaccat ccacgacatc atcctggagt   2040
gcgtgtactg taagcagcag ctgctgagaa gagaggtgta cgacttcgcc ttcagagacc   2100
tgtgcatcgt gtacagagac ggcaaccctt acgccgtgtg cgataagtgt ctgaagttct   2160
attccaaaat ctccgaatat aggtacatgc acggcgacac ccctacctg cacgagtaca   2220 tgctggacct ccagcctgag accacagacc tgtactgcta cgagcagctg aacgacagct   2280
ctgaggaaga ggacgagatt gacggacctg ctggccaggc cgagcctgac agagcccact   2340
acaatatcgt gacattctgt tgcaaatgcg actccacact ggacaagtgc ctgaagttct   2400
acagcaagat ctctgagtac agacactact gctactctct gtacggcacc acactggagc   2460
agcagtacaa caagcctctg tgcgacctcc tgatccgctg catcaactgc cagaagcctc   2520
tgtgccctga ggagaagcag agacacctgg acaagaagca gcggttccac aacatcagag   2580
gcagatggac cggcaggtgc atgtcctgct gtagatcctc cagaaccaga cgggagaccc   2640
agctgcacta caacatcgtg accttctgct gcaagtgcga ctctacccctg agactgtgcg   2700 tgcagtctac ccacgtggac atcagaaccc tggaggacct gctgatgggc accctgggca   2760
```

```
tcgtgtgccc tatctgctct cagaagccta tggccaggtt cgaggaccct accagaagac    2820
cctacaagct gcctgacctg tgcaccgagc tgaacacctc tctgcaagac atcgagatca    2880
cctgcgtgta ctgcaagacc gtgctggagc tgaccgaggt gttcgagttc gccttcaagg    2940
acctgttcgt ggtgtacaga gacagcatcc ctcacgctgc ctgccacaag tgcatcgact    3000
tctattccag gatcagggag ctgcgctatt actccgactc tgtgatgtac ggccccaagg    3060
ccaccctcca ggacatcgtg ctgcacctgg agcctcagaa cgagatcccc gtggacctgc    3120
tgtgccacga gcagctgtct gactctgaag aggagaacga cgagatcgac ggcgtgaacc    3180
accagcacct gcctgccagg agagctgaac cccagcggca taccatgctg tgtatgtgct    3240
tctactctag gatcagagag ctgaggtact actctgactc tgtgtacggc gacaccctgg    3300
agaagctgac caacaccggc ctgtacaacc tgctgatccg gtgcctgagg tgccagaagc    3360
ctctgaaccc tgccgagaag ctgagacacc tgaacgagaa gagaagattc cacaagatcg    3420
ctggccacta cagaggccag tgccactctt gctgcaacag agccagacag gagagactcc    3480
agcggagaag ggagacccag gtggccagaa gagccgagcc tcagagacac accatgctgt    3540
gcatgtgctg caagtgcgag gccagaatcg agctggtggt ggagagctct gccgacgacc    3600
tgagagcctt ccagcagctg ttcctgtcta ccctgagctt cgtgtgccct tggtgcgcct    3660
ctcagcagta atctagagtc ggggcggccg gccgcttcga gcagacatga taagatacat    3720
tgatgagttt ggacaaacca actagaat gcagtgaaaa aaatgcttta tttgtgaaat    3780
ttgtgatgct attgctttat ttgtaaccat tataagctgc aataaacaag ttaacaacaa    3840
caattgcatt cattttatgt ttcaggttca gggggaggtg tgggaggttt tttaaagcaa    3900
gtaaaacctc tacaaatgtg gtaaaatcga taaggatctg aacgatggag cggagaatgg    3960
gcggaactgg gcggagttag gggcgggatg ggcggagtta ggggcgggac tatggttgct    4020
gactaattga gatgcatgct ttgcatactt ctgcctgctg gggagcctgg ggactttcca    4080
cacctggttg ctgactaatt gagatgcatg cttttgcatac ttctgcctgc tggggagcct    4140
ggggactttc cacaccctaa ctgacacaca ttccacagcg gatccgtcga cttcagaaga    4200
actcgtcaag aaggcgatag aaggcgatgc gccgcgaatc gggagcggcg ataccgtaga    4260 gcacaggaa gcggtcagcc cattcgccgc caagctcttc agcaatatca cgggtagcca    4320
acgctatgtc ctgatagcgg tccgccacac ccagccggcc acagtcgatg aatccagaaa    4380
agcggccatt ttccaccatg atattcggca agcaggcatc gccatgggtc acgacgagat    4440
cctcgccgtc gggcatgctc gccttgagcc tggcgaacag ttcggctggc gcgagcccct    4500
gatgctcttc gtccagatca tcctgatcga caagaccggc ttccatccga gtacgtgctc    4560
gctcgatgcg atgtttcgct tggtggtcga atgggcaggt agccggatca gcgtatgca    4620 gccgccgcat tgcatcagcc atgatggata cttctcggc aggagcaagg tgagatgaca    4680
ggagatcctg ccccggcact cgcccaata gcagccagtc ccttcccgct tcagtgacaa    4740
cgtcgagcac agctgcgcaa ggaacgcccg tcgtggccag ccacgatagc cgcgctgcct    4800
cgtcttgcag ttcattcagg gcaccggaca ggtcggtctt gacaaaaaga accgggcgcc    4860
cctgcgctga cagccggaac acggcggcat cagagcagcc gattgtctgt tgtgcccagt    4920
catagccgaa tagcctctcc acccaagcgg ccggagaacc tgcgtgcaat ccatcttgtt    4980
caatcatgcg aaacgatcct catcctgtct cttgatcaga tcttgatccc ctgcgccatc    5040
agatccttgg cggcaagaaa gccatccagt ttactttgca gggcttccca accttaccag    5100
```

-continued

```
agggcgcccc agctggcaat tccggttcgc ttgctgtcca taaaaccgcc cagtctagct    5160
atcgccatgt aagcccactg caagctacct gctttctctt tgcgcttgcg ttttcccttg    5220
tccagatagc ccagtagctg acattcatcc ggggtcagca ccgtttctgc ggactggctt    5280
tctacgtgaa aaggatctag gtgaagatcc tttttgataa tctcatgacc aaaatccctt    5340
aacgtgagtt ttcgttccac tgagcgtcag accccgtaga aagatcaaa ggatcttctt     5400 gagatccttt ttttctgcgc gtaatctgct gcttgcaaac aaaaaaacca ccgctaccag    5460
cggtggtttg tttgccggat caagagctac caactctttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagataccta cagcgtgagc tatgagaaag cgccacgctt cccgaaggga    5820
gaaaggcgga caggtatccg gtaagcggca gggtcggaac aggagagcgc acgagggagc    5880
ttccaggggg aaacgcccgg tatctttata gtcctgtcgg gtttcgccac ctctgacttg    5940
agcgtcgatt tttgtgatgc tcgtcagggg gcggagcct atggaaaaac gccagcaacg     6000
cggccttttt acggttcctg gccttttgct ggccttttgc tcacatgttc gggcccaatc    6060
gacccgggcg acggccagtg aattg                                          6085
```

<210> SEQ ID NO 106
<211> LENGTH: 767
<212> TYPE: PRT
<213> ORGANISM: Artificial Sequence
<220> FEATURE:
<223> OTHER INFORMATION: C-1

<400> SEQUENCE: 106

```
Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Gly Ser Gly Asp Ala Ser Met His Gln Lys
            180                 185                 190
```

```
Arg Thr Ala Met Phe Gln Asp Pro Gln Glu Arg Pro Arg Lys Leu Pro
        195                 200                 205

Gln Leu Cys Thr Glu Leu Gln Thr Thr Ile His Asp Ile Ile Leu Glu
    210                 215                 220

Cys Val Tyr Cys Lys Gln Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
                245                 250                 255

Val Cys Asp Lys Cys Leu Lys Phe Tyr Ser Lys Ile Ser Glu Tyr Arg
                260                 265                 270

Tyr Met His Gly Asp Thr Pro Thr Leu His Glu Tyr Met Leu Asp Leu
            275                 280                 285

Gln Pro Glu Thr Thr Asp Leu Tyr Cys Tyr Glu Gln Leu Asn Asp Ser
        290                 295                 300

Ser Glu Glu Glu Asp Glu Ile Asp Gly Pro Ala Gly Gln Ala Glu Pro
305                 310                 315                 320

Asp Arg Ala His Tyr Asn Ile Val Thr Phe Cys Cys Lys Cys Asp Ser
                325                 330                 335

Thr Leu Asp Lys Cys Leu Lys Phe Tyr Ser Lys Ile Ser Glu Tyr Arg
                340                 345                 350

His Tyr Cys Tyr Ser Leu Tyr Gly Thr Thr Leu Glu Gln Gln Tyr Asn
            355                 360                 365

Lys Pro Leu Cys Asp Leu Leu Ile Arg Cys Ile Asn Cys Gln Lys Pro
        370                 375                 380

Leu Cys Pro Glu Glu Lys Gln Arg His Leu Asp Lys Lys Gln Arg Phe
385                 390                 395                 400

His Asn Ile Arg Gly Arg Trp Thr Gly Arg Cys Met Ser Cys Cys Arg
                405                 410                 415

Ser Ser Arg Thr Arg Arg Glu Thr Gln Leu His Tyr Asn Ile Val Thr
                420                 425                 430

Phe Cys Cys Lys Cys Asp Ser Thr Leu Arg Leu Cys Val Gln Ser Thr
            435                 440                 445

His Val Asp Ile Arg Thr Leu Glu Asp Leu Leu Met Gly Thr Leu Gly
        450                 455                 460

Ile Val Cys Pro Ile Cys Ser Gln Lys Pro Met Ala Arg Phe Glu Asp
465                 470                 475                 480

Pro Thr Arg Arg Pro Tyr Lys Leu Pro Asp Leu Cys Thr Glu Leu Asn
                485                 490                 495

Thr Ser Leu Gln Asp Ile Glu Ile Thr Cys Val Tyr Cys Lys Thr Val
            500                 505                 510

Leu Glu Leu Thr Glu Val Phe Glu Phe Ala Phe Lys Asp Leu Phe Val
        515                 520                 525

Val Tyr Arg Asp Ser Ile Pro His Ala Ala Cys His Lys Cys Ile Asp
530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
                565                 570                 575

Gln Asn Glu Ile Pro Val Asp Leu Leu Cys His Glu Gln Leu Ser Asp
            580                 585                 590

Ser Glu Glu Glu Asn Asp Glu Ile Asp Gly Val Asn His Gln His Leu
        595                 600                 605
```

```
Pro Ala Arg Arg Ala Glu Pro Gln Arg His Thr Met Leu Cys Met Cys
    610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
                645                 650                 655

Ile Arg Cys Leu Arg Cys Gln Lys Pro Leu Asn Pro Ala Glu Lys Leu
            660                 665                 670

Arg His Leu Asn Glu Lys Arg Phe His Lys Ile Ala Gly His Tyr
        675                 680                 685

Arg Gly Gln Cys His Ser Cys Cys Asn Arg Ala Arg Gln Glu Arg Leu
    690                 695                 700

Gln Arg Arg Arg Glu Thr Gln Val Ala Arg Arg Ala Glu Pro Gln Arg
705                 710                 715                 720

His Thr Met Leu Cys Met Cys Lys Cys Glu Ala Arg Ile Glu Leu
                725                 730                 735

Val Val Glu Ser Ser Ala Asp Asp Leu Arg Ala Phe Gln Gln Leu Phe
                740                 745                 750

Leu Ser Thr Leu Ser Phe Val Cys Pro Trp Cys Ala Ser Gln Gln
            755                 760                 765

<210> SEQ ID NO 107
<211> LENGTH: 6085
<212> TYPE: DNA
<213> ORGANISM: Artificial Sequence
<220> FEATURE:
<223> OTHER INFORMATION: C-2 mutant
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2186)
<223> OTHER INFORMATION: 16E6N
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2187)..(2381)
<223> OTHER INFORMATION: 16E7N (M12K, N29S)
<220> FEATURE:
<221> NAME/KEY: misc_feature
<222> LOCATION: (2382)..(2645)
<223> OTHER INFORMATION: 16E6C
<220> FEATURE:
<221> NAME/KEY: misc_feature
<222> LOCATION: (2646)..(2789)
<223> OTHER INFORMATION: 16E7C (R77S, G85S)
<220> FEATURE:
<221> NAME/KEY: misc_feature
<222> LOCATION: (2790)..(3671)
<223> OTHER INFORMATION: 18E6/E7

<400> SEQUENCE: 107
taccgatgta cgggccagat atacgcgttg acattgatta ttgactagtt attaatagta    60
atcaattacg gggtcattag ttcatagccc atatatggag ttccgcgtta cataacttac   120
ggtaaatggc ccgcctggct gaccgcccaa cgacccccgc ccattgacgt caataatgac   180
gtatgttccc atagtaacgc caataggga c tttccattga cgtcaatggg tggagtattt   240
```

```
acggtaaact gcccacttgg cagtacatca agtgtatcat atgccaagta cgccccctat    300
tgacgtcaat gacggtaaat ggcccgcctg gcattatgcc cagtacatga ccttatggga    360
ctttcctact tggcagtaca tctacgtatt agtcatcgct attaccatgg tgatgcggtt    420
ttggcagtac atcaatgggc gtggatagcg gtttgactca cggggatttc caagtctcca    480
ccccattgac gtcaatggga gtttgttttg gcaccaaaat caacgggact ttccaaaatg    540
tcgtaacaac tccgccccat tgacgcaaat gggcggtagg cgtgtacggt gggaggtcta    600
tataagcaga gctctctggc taactagaga acccactgct tactggctta tcgaaattaa    660
tacgactcac tatagggaga cccaagctgg ctagcgtgag tttggggacc cttgattgtt    720
ctttcttttt cgctattgta aaattcatgt tatatggagg gggcaaagtt ttcagggtgt    780
tgtttagaac gggaagatgt cccttgtatc accatggacc ctcatgataa ttttgtttct    840
ttcactttct actctgttga caaccattgt ctcctcttat tttcttttca ttttctgtaa    900 cttttttcgtt aaactttagc ttgcattgt aacgaatttt taaattcact tttgtttatt    960
tgtcagattg taagtacttt ctctaatcac ttttttttca aggcaatcag ggtatattat    1020
attgtacttc agcacagttt tagagaacaa ttgttataat taaatgataa ggtagaatat    1080
ttctgcatat aaattctggc tggcgtggaa atattcttat tggtagaaac aactacatcc    1140
tggtcatcat cctgcctttc tctttatggt tacaatgata tacactgttt gagatgagga    1200
taaaatactc tgagtccaaa ccgggcccct ctgctaacca tgttcatgcc ttcttctttt    1260
tcctacagct cctgggcaac gtgctggtta ttgtgctgtc tcatcatttt ggcaaagaat    1320
tgtaatacga ctcactatag ggcgaattga agcttggtac cgccaccatg gatgctatga    1380
aacggggcct gtgctgcgtg ctgctcctgt gcggcgctgt gtttgtgagc cctagcatca    1440
cccaggactg ctccttccaa cacagcccca tctcctccga cttcgctgtc aaaatccgtg    1500
agctgtctga ctacctgctt caagattacc cagtcaccgt ggcctccaac ctgcaggacg    1560
aggagctctg cggggggcctc tggcggctgg tcctggcaca gcgctggatg gagcggctca    1620
agactgtcgc tgggtccaag atgcaaggct tgctggagcg cgtgaacacg gagatacact    1680
ttgtcaccaa atgtgccttt cagcccccc ccagctgtct tcgcttcgtc cagaccaaca    1740
tctcccgcct cctgcaggag acctccgagc agctggtggc gctgaagccc tggatcactc    1800
gccagaactt ctcccggtgc ctggagctgc agtgtcagcc cgactcctca accctgccac    1860
ccccatggag tccccggccc ctggaggcca cagccccgac agcccccggc ggcggcagcg    1920
gcgatgctag catgcaccag aagagaaccg ccatgttcca ggaccctcag gagagaccta    1980
ggaagctgcc tcacctgtgt acagagctcc agacaaccat ccacgacatc atcctggagt    2040
gcgtgtactg taagcagcag ctgctgagaa gagaggtgta cgacttcgcc ttcagagacc    2100
tgtgcatcgt gtacagagac ggcaaccctt acgccgtgtg cgataagtgt ctgaagttct    2160
attccaaaat ctccgaatat aggtacatgc acggcgacac ccctacctg cacgagtaca    2220 agctggacct ccagcctgag accacagacc tgtactgcta cgagcagctg tctgacagct    2280
ctgaggaaga ggacgagatt gacggacctg ctggccaggc cgagcctgac agagccact    2340 acaatatcgt gacattctgt tgcaaatgcg actccacact ggacagtgc ctgaagttct    2400 acagcaagat ctctgagtac agatactact gctactctgt gtacggcacc acactggagc    2460
agcagtacaa caagcctctg tgcgacctcc tgatccgctg catcaactgc cagaagcctc    2520
tgtgccctga ggagaagcag agacacctgg acaagaagca gcggttccac aacatcagag    2580
```

-continued

| | |
|---|---|
| gcagatggac cggcaggtgc atgtcctgct gtagatcctc cagaaccaga cgggagaccc | 2640 |
| agctgcacta caacatcgtg accttctgct gcaagtgcga ctctaccctg agactgtgcg | 2700 |
| tgcagtctac ccacgtggac atcctcaccc tggaggacct gctgatgctc accctgggca | 2760 |
| tcgtgtgccc tatctgctct cagaagccta tggccaggtt cgaggaccct accagaagac | 2820 |
| cctacaagct gcctgacctg tgcaccgagc tgaacacctc tctgcaagac atcgagatca | 2880 |
| cctgcgtgta ctgcaagacc gtgctggagc tgaccgaggt gttcgagttc gccttcaagg | 2940 |
| acctgttcgt ggtgtacaga gacagcatcc ctcacgctgc ctgccacaag tgcatcgact | 3000 |
| tctattccag gatcagggag ctgcgctatt actccgactc tgtgatgtac gccccaagg | 3060 |
| ccaccctcca ggacatcgtg ctgcacctgg agcctcagaa cgagatcccc gtggacctgc | 3120 |
| tgtgccacga gcagctgtct gactctgaag aggagaacga cgagatcgac ggcgtgaacc | 3180 |
| accagcacct gcctgccagg agagctgaac cccagcggca taccatgctg tgtatgtgct | 3240 |
| tctactctag gatcagagag ctgaggtact actctgactc tgtgtacggc gacaccctgg | 3300 |
| agaagctgac caacaccggc ctgtacaacc tgctgatccg gtgcctgagg tgccagaagc | 3360 |
| ctctgaaccc tgccgagaag ctgagacacc tgaacgagaa gagaagattc cacaagatcg | 3420 |
| ctggccacta cagaggccag tgccactctt gctgcaacag agccagacag agagactcc | 3480 |
| agcggagaag ggagacccag gtggccagaa gagccgagcc tcagacacac accatgctgt | 3540 |
| gcatgtgctg caagtgcgag gccagaatcg agctggtggt ggagagctct gccgacgacc | 3600 |
| tgagagcctt ccagcagctg ttcctgtcta ccctgagctt cgtgtgccct tggtgcgcct | 3660 |
| ctcagcagta atctagagtc ggggcggccg gccgcttcga gcagacatga taagatacat | 3720 |
| tgatgagttt ggacaaacca caactagaat gcagtgaaaa aaatgcttta tttgtgaaat | 3780 |
| ttgtgatgct attgctttat ttgtaaccat tataagctgc aataaacaag ttaacaacaa | 3840 |
| caattgcatt cattttatgt ttcaggttca gggggaggtg tgggaggttt tttaaagcaa | 3900 |
| gtaaaacctc tacaaatgtg gtaaaatcga taaggatctg aacgatggag cggagaatgg | 3960 |
| gcggaactgg gcggagttag gggcgggatg ggcggagtta ggggcgggac tatggttgct | 4020 |
| gactaattga gatgcatgct ttgcatactt ctgcctgctg gggagcctgg ggactttcca | 4080 |
| cacctggttg ctgactaatt gagatgcatg cttttgcatac ttctgcctgc tggggagcct | 4140 |
| ggggactttc cacaccctaa ctgacacaca ttccacagcg gatccgtcga cttcagaaga | 4200 |
| actcgtcaag aaggcgatag aaggcgatgc gccgcgaatc gggagcggcg ataccgtaga | 4260 |
| gcacgaggaa gcggtcagcc cattcgccgc caagctcttc agcaatatca cgggtagcca | 4320 |
| acgctatgtc ctgatagcgg tccgccacac ccagccggcc acagtcgatg aatccagaaa | 4380 |
| agcggccatt ttccaccatg atattcggca agcaggcatc gccatgggtc acgacgagat | 4440 |
| cctcgccgtc gggcatgctc gccttgagcc tggcgaacag ttcggctggc gcgagcccct | 4500 |
| gatgctcttc gtccagatca tcctgatcga caagaccggc ttccatccga gtacgtgctc | 4560 |
| gctcgatgcg atgtttcgct tggtggtcga atgggcaggt agccggatca gcgtatgca | 4620 |
| gccgccgcat tgcatcagcc atgatggata ctttctcggc aggagcaagg tgagatgaca | 4680 |
| ggagatcctg ccccggcact tcgcccaata gcagccagtc cttcccgct tcagtgacaa | 4740 |
| cgtcgagcac agctgcgcaa ggaacgcccg tcgtggccag ccacgatagc cgcgctgcct | 4800 |
| cgtcttgcag ttcattcagg gcaccggaca ggtcggtctt gacaaaaaga accgggcgcc | 4860 |
| cctgcgctga cagccggaac acggcggcat cagagcagcc gattgtctgt tgtgcccagt | 4920 |
| catagccgaa tagcctctcc acccaagcgg ccggagaacc tgcgtgcaat ccatcttgtt | 4980 |

```
caatcatgcg aaacgatcct catcctgtct cttgatcaga tcttgatccc ctgcgccatc    5040
agatccttgg cggcaagaaa gccatccagt ttactttgca gggcttccca accttaccag    5100
agggcgcccc agctggcaat tccggttcgc ttgctgtcca taaaaccgcc cagtctagct    5160
atcgccatgt aagcccactg caagctacct gctttctctt tgcgcttgcg ttttcccttg    5220
tccagatagc ccagtagctg acattcatcc ggggtcagca ccgtttctgc ggactggctt    5280
tctacgtgaa aaggatctag gtgaagatcc tttttgataa tctcatgacc aaaatcccct    5340
aacgtgagtt ttcgttccac tgagcgtcag accccgtaga aaagatcaaa ggatcttctt    5400
gagatccttt tttctgcgc gtaatctgct gcttgcaaac aaaaaaacca ccgctaccag    5460
cggtggtttg tttgccggat caagagctac caactctttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagatacct a cagcgtgagc tatgagaaag cgccacgctt ccgaaggga    5820
gaaaggcgga caggtatccg gtaagcggca gggtcggaac aggagagcgc acgagggagc    5880
ttccaggggg aaacgcccgg tatctttata gtcctgtcgg gtttcgccac ctctgacttg    5940
agcgtcgatt tttgtgatgc tcgtcagggg ggcggagcct atggaaaaac gccagcaacg    6000
cggcctttt acggttcctg gccttttgct ggccttttgc tcacatgttc gggcccaatc    6060
gacccgggcg acggccagtg aattg                                         6085
```

<210> SEQ ID NO 108
<211> LENGTH: 767
<212> TYPE: PRT
<213> ORGANISM: Artificial Sequence
<220> FEATURE:
<223> OTHER INFORMATION: C-2

<400> SEQUENCE: 108

Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

```
Ser Thr Leu Pro Pro Pro Trp Ser Pro Arg Pro Leu Glu Ala Thr Ala
            165                 170                 175

Pro Thr Ala Pro Gly Gly Gly Ser Gly Asp Ala Ser Met His Gln Lys
        180                 185                 190

Arg Thr Ala Met Phe Gln Asp Pro Gln Glu Arg Pro Arg Lys Leu Pro
            195                 200                 205

His Leu Cys Thr Glu Leu Gln Thr Thr Ile His Asp Ile Ile Leu Glu
    210                 215                 220

Cys Val Tyr Cys Lys Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
            245                 250                 255

Val Cys Asp Lys Cys Leu Lys Phe Tyr Ser Lys Ile Ser Glu Tyr Arg
            260                 265                 270

Tyr Met His Gly Asp Thr Pro Thr Leu His Glu Tyr Lys Leu Asp Leu
        275                 280                 285

Gln Pro Glu Thr Thr Asp Leu Tyr Cys Tyr Glu Gln Leu Ser Asp Ser
    290                 295                 300

Ser Glu Glu Glu Asp Glu Ile Asp Gly Pro Ala Gly Gln Ala Glu Pro
305                 310                 315                 320

Asp Arg Ala His Tyr Asn Ile Val Thr Phe Cys Cys Lys Cys Asp Ser
            325                 330                 335

Thr Leu Asp Lys Cys Leu Lys Phe Tyr Ser Lys Ile Ser Glu Tyr Arg
            340                 345                 350

Tyr Tyr Cys Tyr Ser Val Tyr Gly Thr Thr Leu Glu Gln Gln Tyr Asn
        355                 360                 365

Lys Pro Leu Cys Asp Leu Leu Ile Arg Cys Ile Asn Cys Gln Lys Pro
    370                 375                 380

Leu Cys Pro Glu Glu Lys Gln Arg His Leu Asp Lys Lys Gln Arg Phe
385                 390                 395                 400

His Asn Ile Arg Gly Arg Trp Thr Gly Arg Cys Met Ser Cys Cys Arg
            405                 410                 415

Ser Ser Arg Thr Arg Arg Glu Thr Gln Leu His Tyr Asn Ile Val Thr
        420                 425                 430

Phe Cys Cys Lys Cys Asp Ser Thr Leu Arg Leu Cys Val Gln Ser Thr
    435                 440                 445

His Val Asp Ile Leu Thr Leu Glu Asp Leu Leu Met Leu Thr Leu Gly
    450                 455                 460

Ile Val Cys Pro Ile Cys Ser Gln Lys Pro Met Ala Arg Phe Glu Asp
465                 470                 475                 480

Pro Thr Arg Arg Pro Tyr Lys Leu Pro Asp Leu Cys Thr Glu Leu Asn
            485                 490                 495

Thr Ser Leu Gln Asp Ile Glu Ile Thr Cys Val Tyr Cys Lys Thr Val
        500                 505                 510

Leu Glu Leu Thr Glu Val Phe Glu Phe Ala Phe Lys Asp Leu Phe Val
    515                 520                 525

Val Tyr Arg Asp Ser Ile Pro His Ala Ala Cys His Lys Cys Ile Asp
    530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
            565                 570                 575

Gln Asn Glu Ile Pro Val Asp Leu Leu Cys His Glu Gln Leu Ser Asp
```

|     |     |     |     | 580 |     |     |     | 585 |     |     |     | 590 |     |     |
| --- | --- | --- | --- | --- | --- | --- | --- | --- | --- | --- | --- | --- | --- | --- |
| Ser | Glu | Glu | Glu | Asn | Asp | Glu | Ile | Asp | Gly | Val | Asn | His | Gln | His | Leu |
|     |     |     |     | 595 |     |     |     |     | 600 |     |     |     |     | 605 |     |

Pro Ala Arg Arg Ala Glu Pro Gln Arg His Thr Met Leu Cys Met Cys
    610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
                645                 650                 655

Ile Arg Cys Leu Arg Cys Gln Lys Pro Leu Asn Pro Ala Glu Lys Leu
            660                 665                 670

Arg His Leu Asn Glu Lys Arg Arg Phe His Lys Ile Ala Gly His Tyr
            675                 680                 685

Arg Gly Gln Cys His Ser Cys Cys Asn Arg Ala Arg Gln Glu Arg Leu
        690                 695                 700

Gln Arg Arg Arg Glu Thr Gln Val Ala Arg Arg Ala Glu Pro Gln Arg
705                 710                 715                 720

His Thr Met Leu Cys Met Cys Cys Lys Cys Glu Ala Arg Ile Glu Leu
                725                 730                 735

Val Val Glu Ser Ser Ala Asp Asp Leu Arg Ala Phe Gln Gln Leu Phe
                740                 745                 750

Leu Ser Thr Leu Ser Phe Val Cys Pro Trp Cys Ala Ser Gln Gln
            755                 760                 765

<210> SEQ ID NO 109
<211> LENGTH: 5995
<212> TYPE: DNA
<213> ORGANISM: Artificial Sequence
<220> FEATURE:
<223> OTHER INFORMATION: D-1 (overlapping-1)
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2165)
<223> OTHER INFORMATION: 16E6N (1-78aa)
<220> FEATURE:
<221> NAME/KEY: misc_feature
<222> LOCATION: (2166)..(2339)
<223> OTHER INFORMATION: 16E7N (1-58aa)
<220> FEATURE:
<221> NAME/KEY: misc_feature
<222> LOCATION: (2340)..(2579)
<223> OTHER INFORMATION: 16E6C (79-158aa)
<220> FEATURE:
<221> NAME/KEY: misc_feature
<222> LOCATION: (2580)..(2699)
<223> OTHER INFORMATION: 16E7C (59-98aa)
<220> FEATURE:
<221> NAME/KEY: misc_feature
<222> LOCATION: (2700)..(3581)
<223> OTHER INFORMATION: 18E6/E7

<400> SEQUENCE: 109
taccgatgta cgggccagat atacgcgttg acattgatta ttgactagtt attaatagta    60
atcaattacg gggtcattag ttcatagccc atatatggag ttccgcgtta cataacttac   120
ggtaaatggc ccgcctggct gaccgcccaa cgacccccgc ccattgacgt caataatgac   180

```
gtatgttccc ataqtaacgc caataqggac tttccattga cgtcaatggg tggagtattt      240
acggtaaact gcccacttgg cagtacatca agtgtatcat atgccaagta cgccccctat      300
tgacgtcaat gacggtaaat ggcccgcctg gcattatgcc cagtacatga ccttatggga      360
ctttcctact tggcagtaca tctacgtatt agtcatcgct attaccatgg tgatgcggtt      420
ttggcagtac atcaatgggc gtggatagcg gtttgactca cggggatttc caagtctcca      480
ccccattgac gtcaatggga gtttgttttg gcaccaaaat caacgggact ttccaaaatg      540
tcgtaacaac tccgccccat tgacgcaaat gggcggtagg cgtgtacggt gggaggtcta      600
tataagcaga gctctctggc taactagaga acccactgct tactggctta tcgaaattaa      660
tacgactcac tatagggaga cccaagctgg ctagcgtgag tttggggacc cttgattgtt      720
ctttcttttt cgctattgta aaattcatgt tatatggagg gggcaaagtt ttcagggtgt      780
tgtttagaac gggaagatgt cccttgtatc accatggacc ctcatgataa ttttgtttct      840
ttcactttct actctgttga caaccattgt ctcctcttat tttcttttca ttttctgtaa      900 cttttcgtt aaactttagc ttgcatttgt aacgaatttt taaattcact tttgtttatt      960
tgtcagattg taagtacttt ctctaatcac ttttttttca aggcaatcag ggtatattat     1020
attgtacttc agcacagttt tagagaacaa ttgttataat taaatgataa ggtagaatat     1080
ttctgcatat aaattctggc tggcgtggaa atattcttat tggtagaaac aactacatcc     1140
tggtcatcat cctgcctttc tctttatggt tacaatgata tacactgttt gagatgagga     1200
taaaatactc tgagtccaaa ccgggcccct ctgctaacca tgttcatgcc ttcttctttt     1260
tcctacagct cctgggcaac gtgctggtta ttgtgctgtc tcatcatttt ggcaaagaat     1320
tgtaatacga ctcactatag ggcgaattga agcttggtac cgccaccatg gatgctatga     1380 aacgggggcct gtgctgcgtg ctgctcctgt gcggcgctgt gtttgtgagc cctagcatca     1440
cccaggactg ctccttccaa cacagcccca tctcctccga cttcgctgtc aaaatccgtg     1500
agctgtctga ctacctgctt caagattacc cagtcaccgt ggcctccaac ctgcaggacg     1560
aggagctctg cggggggcctc tggcggctgg tcctggcaca gcgctggatg gagcggctca     1620
agactgtcgc tgggtccaag atgcaaggct tgctggagcg cgtgaacacg gagatacact     1680 tgtcaccaa atgtgccttt cagcccccccc ccagctgtct tcgcttcgtc cagaccaaca     1740
tctcccgcct cctgcaggag acctccgagc agctggtggc gctgaagccc tggatcactc     1800
gccagaactt ctcccggtgc ctggagctgc agtgtcagcc cgactcctca accctgccac     1860
ccccatggag tccccggccc ctggaggcca cagcccgac agccccgggc ggcggcagcg     1920
gcgatgctag catgcaccag aagagaaccg ccatgttcca ggaccctcag gagagaccta     1980
ggaagctgcc tcacctgtgt acagagctcc agacaaccat ccacgacatc atcctggagt     2040
gcgtgtactg taagcagcag ctgctgagaa gagaggtgta cgacttcgcc ttcagagacc     2100
tgtgcatcgt gtacagagac ggcaacccct acgccgtgtg cgataagtgt ctgaagttct     2160
attccatgca cggcgacacc cctacctgc acgagtacat gctggaccc cagcctgaga     2220 ccacagacct gtactgctac gagcagctga cgacagctc tgaggaagag acgagattg     2280 acggacctgc tggccaggcc gagcctgaca gagccactca aatatcgtg acattctgta     2340 agatctctga gtacagatac tactgctact ctgtgtacgg caccacactg gagcagcagt     2400
acaacaagcc tctgtgcgac ctcctgatcc gctgcatcaa ctgccagaag cctctgtgcc     2460
ctgaggagaa gcagagacac ctggacaaga gcagcggtt ccacaacatc agaggcagat     2520
ggaccggcag gtgcatgtcc tgctgtagat cctccagaac cagacgggag acccagctgt     2580
```

```
gcaagtgcga ctctaccctg agactgtgcg tgcagtctac ccacgtggac atcagaaccc    2640
tggaggacct gctgatgggc accctgggca tcgtgtgccc tatctgctct cagaagccta    2700
tggccaggtt cgaggaccct accagaagac cctacaagct gcctgacctg tgcaccgagc    2760
tgaacacctc tctgcaagac atcgagatca cctgcgtgta ctgcaagacc gtgctggagc    2820
tgaccgaggt gttcgagttc gccttcaagg acctgttcgt ggtgtacaga gacagcatcc    2880
ctcacgctgc ctgccacaag tgcatcgact tctattccag gatcagggag ctgcgctatt    2940
actccgactc tgtgatgtac ggccccaagg ccaccctcca ggacatcgtg ctgcacctgg    3000
agcctcagaa cgagatcccc gtggacctgc tgtgccacga gcagctgtct gactctgaag    3060
aggagaacga cgagatcgac ggcgtgaacc accagcacct gcctgccagg agagctgaac    3120
cccagcggca taccatgctg tgtatgtgct ctactctag gatcagagag ctgaggtact    3180
actctgactc tgtgtacggc gacaccctgg agaagctgac caacaccggc ctgtacaacc    3240
tgctgatccg gtgcctgagg tgccagaagc ctctgaaccc tgccgagaag ctgagacacc    3300
tgaacgagaa gagaagattc cacaagatcg ctggccacta cagaggccag tgccactctt    3360
gctgcaacag agccagacag gagagactcc agcggagaag ggagacccag gtggccagaa    3420
gagccgagcc tcagagacac accatgctgt gcatgtgctg caagtgcgag gccagaatcg    3480
agctggtggt ggagagctct gccgacgacc tgagagcctt ccagcagctg ttcctgtcta    3540
ccctgagctt cgtgtgccct tggtgcgcct ctcagcagta atctagagtc ggggcggccg    3600
gccgcttcga gcagacatga taagatacat tgatgagttt ggacaaacca caactagaat    3660
gcagtgaaaa aaatgcttta tttgtgaaat ttgtgatgct attgctttat ttgtaaccat    3720
tataagctgc aataaacaag ttaacaacaa caattgcatt catttatgt ttcaggttca    3780 gggggaggtg tgggaggttt tttaaagcaa gtaaaacctc tacaaatgtg gtaaaatcga    3840
taaggatctg aacgatggag cggagaatgg gcggaactgg gcggagttag gggcgggatg    3900
ggcggagtta ggggcgggac tatggttgct gactaattga gatgcatgct ttgcatactt    3960
ctgcctgctg gggagcctgg ggactttcca cacctggttg ctgactaatt gagatgcatg    4020 cttttgcatac ttctgcctgc tggggagcct ggggactttc cacaccctaa ctgacacaca    4080
ttccacagcg gatccgtcga cttcagaaga actcgtcaag aaggcgatag aaggcgatgc    4140
gccgcgaatc gggagcggcg ataccgtaga gcacgaggaa gcggtcagcc cattcgccgc    4200
caagctcttc agcaatatca cgggtagcca acgctatgtc ctgatagcgg tccgccacac    4260
ccagccggcc acagtcgatg aatccagaaa agcggccatt ttccaccatg atattcggca    4320
agcaggcatc gccatgggtc acgacgagat cctcgccgtc gggcatgctc gccttgagcc    4380
tggcgaacag ttcggctggc gcgagcccct gatgctcttc gtccagatca tcctgatcga    4440
caagaccggc ttccatccga gtacgtgctc gctcgatgcg atgtttcgct tggtggtcga    4500
atgggcaggt agccggatca gcgtatgca gccgccgcat tgcatcagcc atgatggata    4560
ctttctcggc aggagcaagg tgagatgaca ggagatcctg ccccggcact cgcccaata    4620 gcagccagtc ccttcccgct tcagtgacaa cgtcgagcac agctgcgcaa ggaacgcccg    4680
tcgtggccag ccacgatagc cgcgctgcct cgtcttgcag ttcattcagg gcaccggaca    4740
ggtcggtctt gacaaaaaga accgggcgcc cctgcgctga cagccggaac acggcggcat    4800
cagagcagcc gattgtctgt tgtgcccagt catagccgaa tagcctctcc acccaagcgg    4860
ccggagaacc tgcgtgcaat ccatcttgtt caatcatgcg aaacgatcct catcctgtct    4920
```

```
cttgatcaga tcttgatccc ctgcgccatc agatccttgg cggcaagaaa gccatccagt    4980
ttactttgca gggcttccca accttaccag agggcgcccc agctggcaat tccggttcgc    5040
ttgctgtcca taaaaccgcc cagtctagct atcgccatgt aagcccactg caagctacct    5100
gctttctctt tgcgcttgcg ttttcccttg tccagatagc ccagtagctg acattcatcc    5160
ggggtcagca ccgtttctgc ggactggctt tctacgtgaa aaggatctag gtgaagatcc    5220
tttttgataa tctcatgacc aaaatcccct taacgtgagt ttcgttccac tgagcgtcag    5280
accccgtaga aaagatcaaa ggatcttctt gagatccttt ttttctgcgc gtaatctgct    5340
gcttgcaaac aaaaaaacca ccgctaccag cggtggtttg tttgccggat caagagctac    5400
caactctttt tccgaaggta actggcttca gcagagcgca gataccaaat actgttcttc    5460
tagtgtagcc gtagttaggc caccacttca agaactctgt agcaccgcct acatacctcg    5520
ctctgctaat cctgttacca gtggctgctg ccagtggcga taagtcgtgt cttaccgggt    5580
tggactcaag acgatagtta ccggataagg cgcagcggtc gggctgaacg ggggggttcgt    5640
gcacacagcc cagcttggag cgaacgacct acaccgaact gagataccta cagcgtgagc    5700
tatgagaaag cgccacgctt cccgaaggga gaaaggcgga caggtatccg gtaagcggca    5760
gggtcggaac aggagagcgc acgagggagc ttccaggggg aaacgcccgg tatctttata    5820
gtcctgtcgg gtttcgccac ctctgacttg agcgtcgatt tttgtgatgc tcgtcagggg    5880
ggcggagcct atgaaaaac gccagcaacg cggccttttt acggttcctg gccttttgct    5940
ggccttttgc tcacatgttc gggcccaatc gacccgggcg acggccagtg aattg         5995
```

<210> SEQ ID NO 110
<211> LENGTH: 737
<212> TYPE: PRT
<213> ORGANISM: Artificial Sequence
<220> FEATURE:
<223> OTHER INFORMATION: D-1

<400> SEQUENCE: 110

Met Asp Ala Met Lys Arg Gly Leu Cys Cys Val Leu Leu Leu Cys Gly
1               5                   10                  15

Ala Val Phe Val Ser Pro Ser Ile Thr Gln Asp Cys Ser Phe Gln His
                20                  25                  30

Ser Pro Ile Ser Ser Asp Phe Ala Val Lys Ile Arg Glu Leu Ser Asp
            35                  40                  45

Tyr Leu Leu Gln Asp Tyr Pro Val Thr Val Ala Ser Asn Leu Gln Asp
        50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

```
Pro Thr Ala Pro Gly Gly Gly Ser Gly Asp Ala Ser Met His Gln Lys
            180                 185                 190

Arg Thr Ala Met Phe Gln Asp Pro Gln Glu Arg Pro Arg Lys Leu Pro
            195                 200                 205

His Leu Cys Thr Glu Leu Gln Thr Thr Ile His Asp Ile Ile Leu Glu
            210                 215                 220

Cys Val Tyr Cys Lys Gln Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
            245                 250                 255

Val Cys Asp Lys Cys Leu Lys Phe Tyr Ser Met His Gly Asp Thr Pro
            260                 265                 270

Thr Leu His Glu Tyr Met Leu Asp Leu Gln Pro Glu Thr Thr Asp Leu
            275                 280                 285

Tyr Cys Tyr Glu Gln Leu Asn Asp Ser Ser Glu Glu Glu Asp Glu Ile
            290                 295                 300

Asp Gly Pro Ala Gly Gln Ala Glu Pro Asp Arg Ala His Tyr Asn Ile
305                 310                 315                 320

Val Thr Phe Cys Lys Ile Ser Glu Tyr Arg Tyr Tyr Cys Tyr Ser Val
            325                 330                 335

Tyr Gly Thr Thr Leu Glu Gln Gln Tyr Asn Lys Pro Leu Cys Asp Leu
            340                 345                 350

Leu Ile Arg Cys Ile Asn Cys Gln Lys Pro Leu Cys Pro Glu Glu Lys
            355                 360                 365

Gln Arg His Leu Asp Lys Lys Gln Arg Phe His Asn Ile Arg Gly Arg
            370                 375                 380

Trp Thr Gly Arg Cys Met Ser Cys Cys Arg Ser Ser Arg Thr Arg Arg
385                 390                 395                 400

Glu Thr Gln Leu Cys Lys Cys Asp Ser Thr Leu Arg Leu Cys Val Gln
            405                 410                 415

Ser Thr His Val Asp Ile Arg Thr Leu Glu Asp Leu Leu Met Gly Thr
            420                 425                 430

Leu Gly Ile Val Cys Pro Ile Cys Ser Gln Lys Pro Met Ala Arg Phe
            435                 440                 445

Glu Asp Pro Thr Arg Arg Pro Tyr Lys Leu Pro Asp Leu Cys Thr Glu
            450                 455                 460

Leu Asn Thr Ser Leu Gln Asp Ile Glu Ile Thr Cys Val Tyr Cys Lys
465                 470                 475                 480

Thr Val Leu Glu Leu Thr Glu Val Phe Glu Phe Ala Phe Lys Asp Leu
            485                 490                 495

Phe Val Val Tyr Arg Asp Ser Ile Pro His Ala Ala Cys His Lys Cys
            500                 505                 510

Ile Asp Phe Tyr Ser Arg Ile Arg Glu Leu Arg Tyr Tyr Ser Asp Ser
            515                 520                 525

Val Met Tyr Gly Pro Lys Ala Thr Leu Gln Asp Ile Val Leu His Leu
            530                 535                 540

Glu Pro Gln Asn Glu Ile Pro Val Asp Leu Leu Cys His Glu Gln Leu
545                 550                 555                 560

Ser Asp Ser Glu Glu Asn Asp Glu Ile Asp Gly Val Asn His Gln
            565                 570                 575

His Leu Pro Ala Arg Arg Ala Glu Pro Gln Arg His Thr Met Leu Cys
            580                 585                 590

Met Cys Phe Tyr Ser Arg Ile Arg Glu Leu Arg Tyr Tyr Ser Asp Ser
```

```
                595                 600                 605
Val Tyr Gly Asp Thr Leu Glu Lys Leu Thr Asn Thr Gly Leu Tyr Asn
    610                 615                 620

Leu Leu Ile Arg Cys Leu Arg Cys Gln Lys Pro Leu Asn Pro Ala Glu
625                 630                 635                 640

Lys Leu Arg His Leu Asn Glu Lys Arg Arg Phe His Lys Ile Ala Gly
            645                 650                 655

His Tyr Arg Gly Gln Cys His Ser Cys Cys Asn Arg Ala Arg Gln Glu
            660                 665                 670

Arg Leu Gln Arg Arg Arg Glu Thr Gln Val Ala Arg Ala Glu Pro
675                 680                 685

Gln Arg His Thr Met Leu Cys Met Cys Cys Lys Cys Glu Ala Arg Ile
690                 695                 700

Glu Leu Val Val Glu Ser Ser Ala Asp Asp Leu Arg Ala Phe Gln Gln
705                 710                 715                 720

Leu Phe Leu Ser Thr Leu Ser Phe Val Cys Pro Trp Cys Ala Ser Gln
            725                 730                 735

Gln

<210> SEQ ID NO 111
<211> LENGTH: 6379
<212> TYPE: DNA
<213> ORGANISM: Artificial Sequence
<220> FEATURE:
<223> OTHER INFORMATION: D-2 (overlapping-2)
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2321)
<223> OTHER INFORMATION: 16E6N (1-130aa)
<220> FEATURE:
<221> NAME/KEY: misc_feature
<222> LOCATION: (1932)..(3083)
<223> OTHER INFORMATION: 16E6/E7
<220> FEATURE:
<221> NAME/KEY: misc_feature
<222> LOCATION: (2322)..(2576)
<223> OTHER INFORMATION: 16E7N (1-85aa)
<220> FEATURE:
<221> NAME/KEY: misc_feature
<222> LOCATION: (2577)..(2918)
<223> OTHER INFORMATION: 16E6C (45-158aa)
<220> FEATURE:
<221> NAME/KEY: misc_feature
<222> LOCATION: (2919)..(3083)
<223> OTHER INFORMATION: 16E7C (44-98aa)
<220> FEATURE:
<221> NAME/KEY: misc_feature
<222> LOCATION: (3084)..(3965)
<223> OTHER INFORMATION: 18E6/E7

<400> SEQUENCE: 111
taccgatgta cgggccagat atacgcgttg acattgatta ttgactagtt attaatagta      60
atcaattacg gggtcattag ttcatagccc atatatggag ttccgcgtta cataacttac     120
ggtaaatggc ccgcctggct gaccgcccaa cgacccccgc ccattgacgt caataatgac     180
gtatgttccc atagtaacgc caatagggac tttccattga cgtcaatggg tggagtattt     240
acggtaaact gcccacttgg cagtacatca agtgtatcat atgccaagta cgccccctat     300
```

```
tgacgtcaat gacggtaaat ggcccgcctg gcattatgcc cagtacatga ccttatggga    360
ctttcctact tggcagtaca tctacgtatt agtcatcgct attaccatgg tgatgcggtt    420
ttggcagtac atcaatgggc gtggatagcg gtttgactca cggggatttc caagtctcca    480
ccccattgac gtcaatggga gtttgttttg gcaccaaaat caacgggact ttccaaaatg    540
tcgtaacaac tccgcccat tgacgcaaat gggcggtagg cgtgtacggt gggaggtcta    600
tataagcaga gctctctggc taactagaga acccactgct tactggctta tcgaaattaa    660
tacgactcac tatagggaga cccaagctgg ctagcgtgag tttggggacc cttgattgtt    720 cttcttttt cgctattgta aaattcatgt tatatggagg gggcaaagtt ttcagggtgt    780
tgtttagaac gggaagatgt cccttgtatc accatggacc ctcatgataa ttttgtttct    840
ttcactttct actctgttga caaccattgt ctcctcttat tttcttttca ttttctgtaa    900 cttttcgtt aaactttagc ttgcatttgt aacgaatttt taaattcact tttgtttatt    960
tgtcagattg taagtacttt ctctaatcac ttttttttca aggcaatcag ggtatattat   1020
attgtacttc agcacagttt tagagaacaa ttgttataat taaatgataa ggtagaatat   1080
ttctgcatat aaattctggc tggcgtggaa atattcttat tggtagaaac aactacatcc   1140
tggtcatcat cctgcctttc tctttatggt tacaatgata tacactgttt gagatgagga   1200
taaaatactc tgagtccaaa ccgggcccct ctgctaacca tgttcatgcc ttcttctttt   1260
tcctacagct cctgggcaac gtgctggtta ttgtgctgtc tcatcatttt ggcaaagaat   1320
tgtaatacga ctcactatag ggcgaattga agcttggtac cgccaccatg gatgctatga   1380
aacggggcct gtgctgcgtg ctgctcctgt gcggcgctgt gtttgtgagc cctagcatca   1440
cccaggactg ctccttccaa cacagcccca tctcctccga cttcgctgtc aaaatccgtg   1500
agctgtctga ctacctgctt caagattacc cagtcaccgt ggcctccaac ctgcaggacg   1560
aggagctctg cggggcctc tggcggctgg tcctggcaca cgctggatg gagcggctca   1620 agactgtcgc tgggtccaag atgcaaggct tgctggagcg cgtgaacacg agatacact   1680 ttgtcaccaa atgtgccttt cagccccccc ccagctgtct tcgcttcgtc cagaccaaca   1740
tctcccgcct cctgcaggag acctccgagc agctggtggc gctgaagccc tggatcactc   1800
gccagaactt ctcccggtgc ctggagctgc agtgtcagcc cgactcctca accctgccac   1860
ccccatggag tccccggccc ctggaggcca cagccccgac agccccgggc ggcggcagcg   1920
gcgatgctag catgcaccag aagagaaccg ccatgttcca ggaccctcag gagagaccta   1980
ggaagctgcc tcacctgtgt acagagctcc agacaaccat ccacgacatc atcctggagt   2040
gcgtgtactg taagcagcag ctgctgagaa gagaggtgta cgacttcgcc ttcagagacc   2100
tgtgcatcgt gtacagagac ggcaaccctt acgccgtgtg cgataagtgt ctgaagttct   2160
attccaagat ctctgagtac agatactact gctactctgt gtacggcacc acactggagc   2220
agcagtacaa caagcctctg tgcgacctcc tgatccgctg catcaactgc cagaagcctc   2280
tgtgccctga ggagaagcag agacacctgg acaagaagca gatgcacggc gacacccta   2340 ccctgcacga gtacatgctg gacctccagc ctgagaccac agacctgtac tgctacgagc   2400
agctgaacga cagctctgag gaagaggacg agattgacgg acctgctggc caggccgagc   2460
ctgacagagc ccactacaat atcgtgacat tctgttgcaa gtgcgactct accctgagac   2520
tgtgcgtgca gtctacccac gtggacatca gaaccctgga ggacctgctg atgggcctga   2580
gaagagaggt gtacgacttc gccttcagag acctgtgcat cgtgtacaga gacggcaacc   2640
```

```
cttacgccgt gtgcgataag tgtctgaagt tctattccaa gatctctgag tacagatact    2700
actgctactc tgtgtacggc accacactgg agcagcagta caacaagcct ctgtgcgacc    2760
tcctgatccg ctgcatcaac tgccagaagc ctctgtgccc tgaggagaag cagagacacc    2820
tggacaagaa gcagcggttc cacaaacatca gaggcagatg gaccggcagg tgcatgtcct   2880
gctgtagatc ctccagaacc agacgggaga cccagctgca ggccgagcct gacagagccc    2940
actacaatat cgtgacattc tgttgcaagt gcgactctac cctgagactg tgcgtgcagt    3000
ctacccacgt ggacatcaga accctggagg acctgctgat gggcaccctg gcatcgtgt    3060
gccctatctg ctctcagaag cctatggcca ggttcgagga ccctaccaga agaccctaca    3120
agctgcctga cctgtgcacc gagctgaaca cctctctgca agacatcgag atcacctgcg    3180
tgtactgcaa gaccgtgctg gagctgaccg aggtgttcga gttcgccttc aaggacctgt    3240
tcgtggtgta cagagacagc atccctcacg ctgcctgcca caagtgcatc gacttctatt    3300
ccaggatcag ggagctgcgc tattactccg actctgtgat gtacggcccc aaggccaccc    3360
tccaggacat cgtgctgcac ctggagcctc agaacgagat ccccgtggac ctgctgtgcc    3420
acgagcagct gtctgactct gaagaggaga cgacgagat cgacggcgtg aaccaccagc     3480
acctgcctgc caggagagct gaaccccagc ggcataccat gctgtgtatg tgcttctact    3540
ctaggatcag agagctgagg tactactctg actctgtgta cggcgacacc ctggagaagc    3600
tgaccaacac cggcctgtac aacctgctga tccggtgcct gaggtgccag aagcctctga    3660
accctgccga gaagctgaga cacctgaacg agaagagaag attccacaag atcgctggcc    3720
actacagagg ccagtgccac tcttgctgca acagagccag acaggagaga ctccagcgga    3780
gaagggagac ccaggtggcc agaagagccg agcctcagag acacaccatg ctgtgcatgt    3840
gctgcaagtg cgaggccaga atcgagctgg tggtggagag ctctgccgac gacctgagag    3900
ccttccagca gctgttcctg tctaccctga gcttcgtgtg cccttggtgc gcctctcagc    3960
agtaatctag agtcggggcg gccggccgct tcgagcagac atgataagat acattgatga    4020
gtttggacaa accacaacta gaatgcagtg aaaaaaatgc tttatttgtg aaatttgtga    4080
tgctattgct ttatttgtaa ccattataag ctgcaataaa caagttaaca acaacaattg    4140
cattcatttt atgtttcagg ttcaggggga ggtgtgggag gttttttaaa gcaagtaaaa    4200
cctctacaaa tgtggtaaaa tcgataagga tctgaacgat ggagcggaga atgggcggaa    4260
ctgggcggag ttaggggcgg gatgggcgga gttaggggcg ggactatggt tgctgactaa    4320
ttgagatgca tgctttgcat acttctgcct gctggggagc tggggacttt ccacacctg    4380
gttgctgact aattgagatg catgctttgc atacttctgc ctgctgggga gcctggggac    4440
tttccacacc ctaactgaca cacattccac agcggatccg tcgacttcag aagaactcgt    4500
caagaaggcg atagaaggcg atgcgccgcg aatcgggagc ggcgataccg tagagcacga    4560
ggaagcggtc agcccattcg ccgccaagct cttcagcaat atcacgggta gccaacgcta    4620
tgtcctgata gcggtccgcc acacccagcc ggccacagtc gatgaatcca gaaaagcggc    4680
cattttccac catgatattc ggcaagcagg catcgccatg ggtcacgacg agatcctcgc    4740
cgtcgggcat gctcgccttg agcctggcga acagttcggc tggcgcgagc cctgatgct   4800
cttcgtccag atcatcctga tcgacaagac cggcttccat ccgagtacgt gctcgctcga    4860
tgcgatgttt cgcttggtgg tcgaatgggc aggtagccgg atcaagcgta tgcagccgcc    4920
gcattgcatc agccatgatg gatactttct cggcaggagc aaggtgagat gacaggagat    4980
cctgccccgg cacttcgccc aatagcagcc agtcccttcc cgcttcagtg acaacgtcga    5040
```

-continued

```
gcacagctgc gcaaggaacg cccgtcgtgg ccagccacga tagccgcgct gcctcgtctt    5100
gcagttcatt cagggcaccg gacaggtcgg tcttgacaaa agaaccggg cgccctgcg     5160 ctgacagccg gaacacggcg gcatcagagc agccgattgt ctgttgtgcc cagtcatagc    5220
cgaatagcct ctccacccaa gcggccgag aacctgcgtg caatccatct tgttcaatca    5280
tgcgaaacga tcctcatcct gtctcttgat cagatcttga tccctgcgc catcagatcc    5340 ttggcggcaa gaaagccatc cagtttactt tgcagggctt cccaaccta ccagagggcg    5400 ccccagctgg caattccggt tcgcttgctg tccataaaac cgcccagtct agctatcgcc    5460
atgtaagccc actgcaagct acctgctttc tctttgcgct tgcgttttcc cttgtccaga    5520
tagcccagta gctgacattc atccggggtc agcaccgttt ctgcggactg gctttctacg    5580
tgaaaaggat ctaggtgaag atccttttg ataatctcat gaccaaaatc ccttaacgtg     5640
agttttcgtt ccactgagcg tcagaccccg tagaaagat caaggatct tcttgagatc      5700 cttttttct gcgcgtaatc tgctgcttgc aaacaaaaaa accaccgcta ccagcggtgg    5760
tttgtttgcc ggatcaagag ctaccaactc ttttccgaa ggtaactggc ttcagcagag    5820
cgcagatacc aaatactgtt cttctagtgt agccgtagtt aggccaccac ttcaagaact    5880
ctgtagcacc gcctacatac ctcgctctgc taatcctgtt accagtggct gctgccagtg    5940
gcgataagtc gtgtcttacc gggttggact caagacgata gttaccggat aaggcgcagc    6000
ggtcgggctg aacggggggt tcgtgcacac agcccagctt ggagcgaacg acctacaccg    6060
aactgagata cctacagcgt gagctatgag aaagcgccac gcttcccgaa gggagaaagg    6120
cggacaggta tccggtaagc ggcagggtcg gaacaggaga gcgcacgagg gagcttccag    6180
ggggaaacgc ccggtatctt tatagtcctg tcgggtttcg ccacctctga cttgagcgtc    6240
gatttttgtg atgctcgtca ggggggcgga gcctatggaa aaacgccagc aacgcggcct    6300
ttttacggtt cctggccttt tgctggcctt ttgctcacat gttcgggccc aatcgacccg    6360
ggcgacggcc agtgaattg                                                  6379
```

<210> SEQ ID NO 112
<211> LENGTH: 865
<212> TYPE: PRT
<213> ORGANISM: Artificial Sequence
<220> FEATURE:
<223> OTHER INFORMATION: D-2

<400> SEQUENCE: 112

Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu

-continued

```
            115                 120                 125
Leu Gln Glu Thr Ser Glu Gln Leu Val Ala Leu Lys Pro Trp Ile Thr
130                 135                 140
Arg Gln Asn Phe Ser Arg Cys Leu Glu Leu Gln Cys Gln Pro Asp Ser
145                 150                 155                 160
Ser Thr Leu Pro Pro Pro Trp Ser Pro Arg Pro Leu Glu Ala Thr Ala
                165                 170                 175
Pro Thr Ala Pro Gly Gly Ser Gly Asp Ala Ser Met His Gln Lys
            180                 185                 190
Arg Thr Ala Met Phe Gln Asp Pro Gln Glu Arg Pro Arg Lys Leu Pro
            195                 200                 205
His Leu Cys Thr Glu Leu Gln Thr Thr Ile His Asp Ile Ile Leu Glu
            210                 215                 220
Cys Val Tyr Cys Lys Gln Gln Leu Leu Arg Arg Glu Val Tyr Asp Phe
225                 230                 235                 240
Ala Phe Arg Asp Leu Cys Ile Val Tyr Arg Asp Gly Asn Pro Tyr Ala
                245                 250                 255
Val Cys Asp Lys Cys Leu Lys Phe Tyr Ser Lys Ile Ser Glu Tyr Arg
                260                 265                 270
Tyr Tyr Cys Tyr Ser Val Tyr Gly Thr Thr Leu Glu Gln Gln Tyr Asn
            275                 280                 285
Lys Pro Leu Cys Asp Leu Leu Ile Arg Cys Ile Asn Cys Gln Lys Pro
290                 295                 300
Leu Cys Pro Glu Glu Lys Gln Arg His Leu Asp Lys Lys Gln Met His
305                 310                 315                 320
Gly Asp Thr Pro Thr Leu His Glu Tyr Met Leu Asp Leu Gln Pro Glu
                325                 330                 335
Thr Thr Asp Leu Tyr Cys Tyr Glu Gln Leu Asn Asp Ser Ser Glu Glu
            340                 345                 350
Glu Asp Glu Ile Asp Gly Pro Ala Gly Gln Ala Glu Pro Asp Arg Ala
            355                 360                 365
His Tyr Asn Ile Val Thr Phe Cys Cys Lys Cys Asp Ser Thr Leu Arg
            370                 375                 380
Leu Cys Val Gln Ser Thr His Val Asp Ile Arg Thr Leu Glu Asp Leu
385                 390                 395                 400
Leu Met Gly Leu Arg Arg Glu Val Tyr Asp Phe Ala Phe Arg Asp Leu
                405                 410                 415
Cys Ile Val Tyr Arg Asp Gly Asn Pro Tyr Ala Val Cys Asp Lys Cys
                420                 425                 430
Leu Lys Phe Tyr Ser Lys Ile Ser Glu Tyr Arg Tyr Tyr Cys Tyr Ser
            435                 440                 445
Val Tyr Gly Thr Thr Leu Glu Gln Gln Tyr Asn Lys Pro Leu Cys Asp
            450                 455                 460
Leu Leu Ile Arg Cys Ile Asn Cys Gln Lys Pro Leu Cys Pro Glu Glu
465                 470                 475                 480
Lys Gln Arg His Leu Asp Lys Lys Gln Arg Phe His Asn Ile Arg Gly
                485                 490                 495
Arg Trp Thr Gly Arg Cys Met Ser Cys Cys Arg Ser Ser Arg Thr Arg
                500                 505                 510
Arg Glu Thr Gln Leu Gln Ala Glu Pro Asp Arg Ala His Tyr Asn Ile
            515                 520                 525
Val Thr Phe Cys Cys Lys Cys Asp Ser Thr Leu Arg Leu Cys Val Gln
            530                 535                 540
```

```
Ser Thr His Val Asp Ile Arg Thr Leu Glu Asp Leu Leu Met Gly Thr
545                 550                 555                 560

Leu Gly Ile Val Cys Pro Ile Cys Ser Gln Lys Pro Met Ala Arg Phe
            565                 570                 575

Glu Asp Pro Thr Arg Arg Pro Tyr Lys Leu Pro Asp Leu Cys Thr Glu
        580                 585                 590

Leu Asn Thr Ser Leu Gln Asp Ile Glu Ile Thr Cys Val Tyr Cys Lys
    595                 600                 605

Thr Val Leu Glu Leu Thr Glu Val Phe Glu Phe Ala Phe Lys Asp Leu
610                 615                 620

Phe Val Val Tyr Arg Asp Ser Ile Pro His Ala Ala Cys His Lys Cys
625                 630                 635                 640

Ile Asp Phe Tyr Ser Arg Ile Arg Glu Leu Arg Tyr Tyr Ser Asp Ser
            645                 650                 655

Val Met Tyr Gly Pro Lys Ala Thr Leu Gln Asp Ile Val Leu His Leu
        660                 665                 670

Glu Pro Gln Asn Glu Ile Pro Val Asp Leu Leu Cys His Glu Gln Leu
    675                 680                 685

Ser Asp Ser Glu Glu Asn Asp Glu Ile Asp Gly Val Asn His Gln
690                 695                 700

His Leu Pro Ala Arg Arg Ala Glu Pro Gln Arg His Thr Met Leu Cys
705                 710                 715                 720

Met Cys Phe Tyr Ser Arg Ile Arg Glu Leu Arg Tyr Tyr Ser Asp Ser
            725                 730                 735

Val Tyr Gly Asp Thr Leu Glu Lys Leu Thr Asn Thr Gly Leu Tyr Asn
        740                 745                 750

Leu Leu Ile Arg Cys Leu Arg Cys Gln Lys Pro Leu Asn Pro Ala Glu
    755                 760                 765

Lys Leu Arg His Leu Asn Glu Lys Arg Arg Phe His Lys Ile Ala Gly
770                 775                 780

His Tyr Arg Gly Gln Cys His Ser Cys Cys Asn Arg Ala Arg Gln Glu
785                 790                 795                 800

Arg Leu Gln Arg Arg Glu Thr Gln Val Ala Arg Ala Glu Pro
            805                 810                 815

Gln Arg His Thr Met Leu Cys Met Cys Cys Lys Cys Glu Ala Arg Ile
        820                 825                 830

Glu Leu Val Val Glu Ser Ser Ala Asp Asp Leu Arg Ala Phe Gln Gln
    835                 840                 845

Leu Phe Leu Ser Thr Leu Ser Phe Val Cys Pro Trp Cys Ala Ser Gln
850                 855                 860

Gln
865
```

<210> SEQ ID NO 113
<211> LENGTH: 6085
<212> TYPE: DNA
<213> ORGANISM: Artificial Sequence
<220> FEATURE:
<223> OTHER INFORMATION: E-1 (Order-1)
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L

```
<220> FEATURE:
<221> NAME/KEY: misc_feature
<222> LOCATION: (1932)..(2186)
<223> OTHER INFORMATION: 16E6N
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2187)..(2330)
<223> OTHER INFORMATION: 16E7C
<220> FEATURE:
<221> NAME/KEY: misc_feature
<222> LOCATION: (2331)..(2525)
<223> OTHER INFORMATION: 16E7N
<220> FEATURE:
<221> NAME/KEY: misc_feature
<222> LOCATION: (2526)..(2789)
<223> OTHER INFORMATION: 16E6C
<220> FEATURE:
<221> NAME/KEY: misc_feature
<222> LOCATION: (2790)..(3671)
<223> OTHER INFORMATION: 18E6/E7

<400> SEQUENCE: 113
taccgatgta cgggccagat atacgcgttg acattgatta ttgactagtt attaatagta      60
atcaattacg gggtcattag ttcatagccc atatatggag ttccgcgtta cataacttac     120
ggtaaatggc ccgcctggct gaccgcccaa cgacccccgc ccattgacgt caataatgac     180
gtatgttccc atagtaacgc caatagggac tttccattga cgtcaatggg tggagtattt     240
acggtaaact gcccacttgg cagtacatca agtgtatcat atgccaagta cgccccctat     300
tgacgtcaat gacggtaaat ggcccgcctg gcattatgcc cagtacatga ccttatggga     360
ctttcctact tggcagtaca tctacgtatt agtcatcgct attaccatgg tgatgcggtt     420
ttggcagtac atcaatgggc gtggatagcg gtttgactca cggggatttc caagtctcca     480
ccccattgac gtcaatggga gtttgttttg gcaccaaaat caacgggact ttccaaaatg     540
tcgtaacaac tccgccccat tgacgcaaat gggcggtagg cgtgtacggt gggaggtcta     600
tataagcaga gctctctggc taactagaga acccactgct tactggctta tcgaaattaa     660
tacgactcac tatagggaga cccaagctgg ctagcgtgag tttggggacc cttgattgtt     720
ctttcttttt cgctattgta aaattcatgt tatatggagg ggcaaagtt ttcagggtgt     780 tgtttagaac gggaagatgt cccttgtatc accatgacc tcatgataa ttttgtttct     840 ttcactttct actctgttga caaccattgt ctcctcttat tttcttttca ttttctgtaa     900
ctttttcgtt aaactttagc ttgcatttgt aacgaatttt taaattcact tttgtttatt     960
tgtcagattg taagtacttt ctctaatcac tttttttca aggcaatcag ggtatattat    1020
attgtacttc agcacagttt tagagaacaa ttgttataat taaatgataa ggtagaatat    1080
ttctgcatat aaattctggc tggcgtggaa atattcttat tggtagaaac aactacatcc    1140
tggtcatcat cctgcctttc tctttatggt tacaatgata tacactgttt gagatgagga    1200
taaaatactc tgagtccaaa ccgggcccct ctgctaacca tgttcatgcc ttcttctttt    1260
tcctacagct cctgggcaac gtgctggtta ttgtgctgtc tcatcatttt ggcaaagaat    1320
tgtaatacga ctcactatag ggcgaattga agcttggtac cgccaccatg gatgctatga    1380
aacggggcct gtgctgcgtg ctgctcctgt gcggcgctgt gtttgtgagc cctagcatca    1440
cccaggactg ctccttccaa cacagcccca tctcctccga cttcgctgtc aaaatccgtg    1500
agctgtctga ctacctgctt caagattacc cagtcaccgt ggcctccaac ctgcaggacg    1560
```

| | |
|---|---|
| aggagctctg cgggggcctc tgcggctgg tcctggcaca gcgctggatg gagcggctca | 1620 |
| agactgtcgc tgggtccaag atgcaaggct tgctggagcg cgtgaacacg agatacact | 1680 |
| ttgtcaccaa atgtgccttt cagcccccc ccagctgtct tcgcttcgtc cagaccaaca | 1740 |
| tctcccgcct cctgcaggag acctccgagc agctggtggc gctgaagccc tggatcactc | 1800 |
| gccagaactt ctcccggtgc ctggagctgc agtgtcagcc cgactcctca accctgccac | 1860 |
| ccccatggag tccccggccc ctggaggcca cagccccgac agccccgggc ggcggcagcg | 1920 |
| gcgatgctag catgcaccag aagagaaccg ccatgttcca ggaccctcag gagagaccta | 1980 |
| ggaagctgcc tcacctgtgt acagagctcc agacaaccat ccacgacatc atcctggagt | 2040 |
| gcgtgtactg taagcagcag ctgctgagaa gagaggtgta cgacttcgcc ttcagagacc | 2100 |
| tgtgcatcgt gtacagagac ggcaacccct acgccgtgtg cgataagtgt ctgaagttct | 2160 |
| attccaaaat ctccgaatat aggtaccact acaacatcgt gaccttctgc tgcaagtgcg | 2220 |
| actctaccct gagactgtgc gtgcagtcta cccacgtgga catcagaacc ctggaggacc | 2280 |
| tgctgatggg caccctgggc atcgtgtgcc ctatctgctc tcagaagcct atgcacggcg | 2340 |
| acaccctac cctgcacgag tacatgctgg acctccagcc tgagaccaca gacctgtact | 2400 |
| gctacgagca gctgaacgac agctctgagg aagaggacga gattgacgga cctgctggcc | 2460 |
| aggccgagcc tgacagagcc cactacaata tcgtgacatt ctgttgcaaa tgcgactcca | 2520 |
| cactggacaa gtgcctgaag ttctacagca agatctctga gtacagatac tactgctact | 2580 |
| ctgtgtacgg caccacactg gagcagcagt acaacaagcc tctgtgcgac ctcctgatcc | 2640 |
| gctgcatcaa ctgccagaag cctctgtgcc tgaggagaa gcagagacac ctggacaaga | 2700 |
| agcagcggtt ccacaacatc agaggcagat ggaccggcag gtgcatgtcc tgctgtagat | 2760 |
| cctccagaac cagacgggag acccagctga tggccaggtt cgaggaccct accagaagac | 2820 |
| cctacaagct gcctgacctg tgcaccgagc tgaacacctc tctgcaagac atcgagatca | 2880 |
| cctgcgtgta ctgcaagacc gtgctggagc tgaccgaggt gttcgagttc gccttcaagg | 2940 |
| acctgttcgt ggtgtacaga gacagcatcc tcacgctgc ctgccacaag tgcatcgact | 3000 |
| tctattccag gatcagggag ctgcgctatt actccgactc tgtgatgtac ggccccaagg | 3060 |
| ccacccctcca ggacatcgtg ctgcacctgg agcctcagaa cgagatcccc gtggacctgc | 3120 |
| tgtgccacga gcagctgtct gactctgaag aggagaacga cgagatcgac ggcgtgaacc | 3180 |
| accagcacct gcctgccagg agagctgaac cccagcggca taccatgctg tgtatgtgct | 3240 |
| tctactctag gatcagagag ctgaggtact actctgactc tgtgtacggc gacacccctgg | 3300 |
| agaagctgac caacaccggc ctgtacaacc tgctgatccg gtgcctgagg tgccagaagc | 3360 |
| ctctgaaccc tgccgagaag ctgagacacc tgaacgagaa gaagattc cacaagatcg | 3420 |
| ctggccacta cagaggccag tgccactctt gctgcaacag agccagacag agagactcc | 3480 |
| agcggagaag ggagacccag gtggccagaa gagccgagcc tcagagacac accatgctgt | 3540 |
| gcatgtgctg caagtgcgag gccagaatcg agctggtggt ggagagctct gccgacgacc | 3600 |
| tgagagcctt ccagcagctg ttcctgtcta ccctgagctt cgtgtgccct tggtgcgcct | 3660 |
| ctcagcagta atctagagtc ggggcggccg gccgcttcga gcagacatga taagatacat | 3720 |
| tgatgagttt ggacaaacca aactagaat gcagtgaaaa aaatgcttta tttgtgaaat | 3780 |
| ttgtgatgct attgctttat ttgtaaccat tataagctgc aataaacaag ttaacaacaa | 3840 |
| caattgcatt catttatgt ttcaggttca ggggaggtg tgggaggttt tttaaagcaa | 3900 |
| gtaaaaacctc tacaaatgtg gtaaaatcga taaggatctg aacgatggag cggagaatgg | 3960 |

```
gcggaactgg gcggagttag gggcgggatg ggcggagtta ggggcgggac tatggttgct    4020
gactaattga gatgcatgct ttgcatactt ctgcctgctg gggagcctgg ggactttcca    4080
cacctggttg ctgactaatt gagatgcatg ctttgcatac ttctgcctgc tggggagcct    4140
ggggactttc cacaccctaa ctgacacaca ttccacagcg gatccgtcga cttcagaaga    4200
actcgtcaag aaggcgatag aaggcgatgc ccgcgaatc gggagcggcg ataccgtaga     4260
gcacgaggaa gcggtcagcc cattcgccgc caagctcttc agcaatatca cgggtagcca    4320
acgctatgtc ctgatagcgg tccgccacac ccagccggcc acagtcgatg aatccagaaa    4380
agcggccatt ttccaccatg atattcggca agcaggcatc gccatgggtc acgacgagat    4440
cctcgccgtc gggcatgctc gccttgagcc tggcgaacag ttcggctggc gcgagcccct    4500
gatgctcttc gtccagatca tcctgatcga caagaccggc ttccatccga gtacgtgctc    4560
gctcgatgcg atgtttcgct tggtggtcga atgggcaggt agccggatca agcgtatgca    4620
gccgccgcat tgcatcagcc atgatggata ctttctcggc aggagcaagg tgagatgaca    4680
ggagatcctg ccccggcact cgcccaata gcagccagtc ccttcccgct tcagtgacaa    4740
cgtcgagcac agctgcgcaa ggaacgcccg tcgtggccag ccacgatagc cgcgctgcct    4800
cgtcttgcag ttcattcagg gcaccggaca ggtcggtctt gacaaaaaga accgggcgcc    4860
cctgcgctga cagccggaac acggcggcat cagagcagcc gattgtctgt tgtgcccagt    4920
catagccgaa tagcctctcc acccaagcgg ccggagaacc tgcgtgcaat ccatcttgtt    4980
caatcatgcg aaacgatcct catcctgtct cttgatcaga tcttgatccc ctgcgccatc    5040
agatccttgg cggcaagaaa gccatccagt ttactttgca gggcttccca accttaccag    5100
agggcgcccc agctggcaat tccggttcgc ttgctgtcca taaaaccgcc cagtctagct    5160
atcgccatgt aagcccactg caagctacct gctttctctt tgcgcttgcg ttttcccttg    5220
tccagatagc ccagtagctg acattcatcc ggggtcagca ccgtttctgc ggactggctt    5280
tctacgtgaa aaggatctag gtgaagatcc ttttttgataa tctcatgacc aaaatccctt    5340
aacgtgagtt ttcgttccac tgagcgtcag accccgtaga aaagatcaaa ggatcttctt    5400
gagatccttt ttttctgcgc gtaatctgct gcttgcaaac aaaaaaacca ccgctaccag    5460
cggtggtttg tttgccggat caagagctac caactctttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagataccta cagcgtgagc tatgagaaag cgccacgctt cccgaaggga    5820
gaaaggcgga caggtatccg gtaagcggca gggtcggaac aggagagcgc acgagggagc    5880
ttccaggggg aaacgcccgg tatctttata gtcctgtcgg gtttcgccac ctctgacttg    5940
agcgtcgatt tttgtgatgc tcgtcagggg ggcggagcct atggaaaaac gccagcaacg    6000
cggccttttt acggttcctg gccttttgct ggccttttgc tcacatgttc gggcccaatc    6060
gacccgggcg acggccagtg aattg                                          6085
```

<210> SEQ ID NO 114
<211> LENGTH: 767
<212> TYPE: PRT
<213> ORGANISM: Artificial Sequence
<220> FEATURE:

<223> OTHER INFORMATION: E-1

<400> SEQUENCE: 114

```
Met Asp Ala Met Lys Arg Gly Leu Cys Cys Val Leu Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Gly Ser Gly Asp Ala Ser Met His Gln Lys
            180                 185                 190

Arg Thr Ala Met Phe Gln Asp Pro Gln Glu Arg Pro Arg Lys Leu Pro
        195                 200                 205

His Leu Cys Thr Glu Leu Gln Thr Thr Ile His Asp Ile Ile Leu Glu
    210                 215                 220

Cys Val Tyr Cys Lys Gln Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
                245                 250                 255

Val Cys Asp Lys Cys Leu Lys Phe Tyr Ser Lys Ile Ser Glu Tyr Arg
            260                 265                 270

Tyr His Tyr Asn Ile Val Thr Phe Cys Cys Lys Cys Asp Ser Thr Leu
        275                 280                 285

Arg Leu Cys Val Gln Ser Thr His Val Asp Ile Arg Thr Leu Glu Asp
    290                 295                 300

Leu Leu Met Gly Thr Leu Gly Ile Val Cys Pro Ile Cys Ser Gln Lys
305                 310                 315                 320

Pro Met His Gly Asp Thr Pro Thr Leu His Glu Tyr Met Leu Asp Leu
                325                 330                 335

Gln Pro Glu Thr Thr Asp Leu Tyr Cys Tyr Glu Gln Leu Asn Asp Ser
            340                 345                 350

Ser Glu Glu Glu Asp Glu Ile Asp Gly Pro Ala Gly Gln Ala Glu Pro
        355                 360                 365

Asp Arg Ala His Tyr Asn Ile Val Thr Phe Cys Cys Lys Cys Asp Ser
    370                 375                 380

Thr Leu Asp Lys Cys Leu Lys Phe Tyr Ser Lys Ile Ser Glu Tyr Arg
385                 390                 395                 400
```

```
Tyr Tyr Cys Tyr Ser Val Gly Thr Thr Leu Glu Gln Gln Tyr Asn
            405                 410                 415

Lys Pro Leu Cys Asp Leu Leu Ile Arg Cys Ile Asn Cys Gln Lys Pro
        420                 425                 430

Leu Cys Pro Glu Glu Lys Gln Arg His Leu Asp Lys Lys Gln Arg Phe
            435                 440                 445

His Asn Ile Arg Gly Arg Trp Thr Gly Arg Cys Met Ser Cys Cys Arg
    450                 455                 460

Ser Ser Arg Thr Arg Arg Glu Thr Gln Leu Met Ala Arg Phe Glu Asp
465                 470                 475                 480

Pro Thr Arg Arg Pro Tyr Lys Leu Pro Asp Leu Cys Thr Glu Leu Asn
                485                 490                 495

Thr Ser Leu Gln Asp Ile Glu Ile Thr Cys Val Tyr Cys Lys Thr Val
            500                 505                 510

Leu Glu Leu Thr Glu Val Phe Glu Phe Ala Phe Lys Asp Leu Phe Val
        515                 520                 525

Val Tyr Arg Asp Ser Ile Pro His Ala Ala Cys His Lys Cys Ile Asp
    530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
                565                 570                 575

Gln Asn Glu Ile Pro Val Asp Leu Leu Cys His Glu Gln Leu Ser Asp
            580                 585                 590

Ser Glu Glu Glu Asn Asp Glu Ile Asp Gly Val Asn His Gln His Leu
        595                 600                 605

Pro Ala Arg Arg Ala Glu Pro Gln Arg His Thr Met Leu Cys Met Cys
    610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
                645                 650                 655

Ile Arg Cys Leu Arg Cys Gln Lys Pro Leu Asn Pro Ala Glu Lys Leu
            660                 665                 670

Arg His Leu Asn Glu Lys Arg Phe His Lys Ile Ala Gly His Tyr
        675                 680                 685

Arg Gly Gln Cys His Ser Cys Cys Asn Arg Ala Arg Gln Glu Arg Leu
    690                 695                 700

Gln Arg Arg Arg Glu Thr Gln Val Ala Arg Ala Glu Pro Gln Arg
705                 710                 715                 720

His Thr Met Leu Cys Met Cys Cys Lys Cys Glu Ala Arg Ile Glu Leu
                725                 730                 735

Val Val Glu Ser Ser Ala Asp Asp Leu Arg Ala Phe Gln Gln Leu Phe
            740                 745                 750

Leu Ser Thr Leu Ser Phe Val Cys Pro Trp Cys Ala Ser Gln Gln
        755                 760                 765

<210> SEQ ID NO 115
<211> LENGTH: 6085
<212> TYPE: DNA
<213> ORGANISM: Artificial Sequence
<220> FEATURE:
<223> OTHER INFORMATION: E-2 (Order-2)
<220> FEATURE:
<221> NAME/KEY: misc_feature
<222> LOCATION: (1368)..(1433)
```

```
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2195)
<223> OTHER INFORMATION: 16E6C
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2196)..(2339)
<223> OTHER INFORMATION: 16E7C
<220> FEATURE:
<221> NAME/KEY: misc_feature
<222> LOCATION: (2340)..(2594)
<223> OTHER INFORMATION: 16E6N
<220> FEATURE:
<221> NAME/KEY: misc_feature
<222> LOCATION: (2595)..(2789)
<223> OTHER INFORMATION: 16E7N
<220> FEATURE:
<221> NAME/KEY: misc_feature
<222> LOCATION: (2790)..(3671)
<223> OTHER INFORMATION: 18E6/E7

<400> SEQUENCE: 115
taccgatgta cgggccagat atacgcgttg acattgatta ttgactagtt attaatagta      60
atcaattacg gggtcattag ttcatagccc atatatggag ttccgcgtta cataacttac     120
ggtaaatggc ccgcctggct gaccgcccaa cgacccccgc ccattgacgt caataatgac     180
gtatgttccc atagtaacgc caatagggac tttccattga cgtcaatggg tggagtattt     240
acggtaaact gcccacttgg cagtacatca agtgtatcat atgccaagta cgccccctat     300
tgacgtcaat gacggtaaat ggcccgcctg gcattatgcc cagtacatga ccttatggga     360
ctttcctact tggcagtaca tctacgtatt agtcatcgct attaccatgg tgatgcggtt     420
ttggcagtac atcaatgggc gtggatagcg gtttgactca cggggatttc caagtctcca     480
ccccattgac gtcaatggga gtttgttttg gcaccaaaat caacgggact ttccaaaatg     540
tcgtaacaac tccgccccat tgacgcaaat gggcggtagg cgtgtacggt gggaggtcta     600
tataagcaga gctctctggc taactagaga acccactgct tactggctta tcgaaattaa     660
tacgactcac tatagggaga cccaagctgg ctagcgtgag tttggggacc cttgattgtt     720
ctttcttttt cgctattgta aaattcatgt tatatggagg gggcaaagtt ttcagggtgt     780
tgtttagaac gggaagatgt cccttgtatc accatggacc ctcatgataa ttttgttttct    840
ttcactttct actctgttga caaccattgt ctcctcttat tttcttttca ttttctgtaa     900
cttttcgtt aaactttagc ttgcatttgt aacgaatttt taaattcact tttgtttatt      960
tgtcagattg taagtacttt ctctaatcac ttttttttca aggcaatcag ggtatattat    1020
attgtacttc agcacagttt tagagaacaa ttgttataat taaatgataa ggtagaatat    1080
ttctgcatat aaattctggc tggcgtggaa atattcttat tggtagaaac aactacatcc    1140
tggtcatcat cctgcctttc tctttatggt tacaatgata tacactgttt gagatgagga    1200
taaaatactc tgagtccaaa ccgggcccct gctaacca tgttcatgcc ttcttctttt       1260
tcctacagct cctgggcaac gtgctggtta ttgtgctgtc tcatcatttt ggcaaagaat    1320
tgtaatacga ctcactatag gcgaattga agcttggtac cgccaccatg gatgctatga    1380
aacggggcct gtgctgcgtg ctgctcctgt gcggcgctgt gtttgtgagc cctagcatca    1440
```

```
cccaggactg ctccttccaa cacagcccca tctcctccga cttcgctgtc aaaatccgtg   1500
agctgtctga ctacctgctt caagattacc cagtcaccgt ggcctccaac ctgcaggacg   1560
aggagctctg cggggcctc tggcggctgg tcctggcaca gcgctggatg gagcggctca   1620
agactgtcgc tgggtccaag atgcaaggct gctggagcg cgtgaacacg gagatacact   1680
ttgtcaccaa atgtgccttt cagcccccc ccagctgtct tcgcttcgtc cagaccaaca   1740
tctcccgcct cctgcaggag acctccgagc agctggtggc gctgaagccc tggatcactc   1800
gccagaactt ctcccggtgc ctggagctgc agtgtcagcc cgactcctca ccctgccac   1860 ccccatggag tccccggccc ctggaggcca cagccccgac agccccgggc ggcggcagcg   1920
gcgatgctag cgacaagtgc ctgaagttct acagcaagat ctctgagtac agatactact   1980
gctactctgt gtacggcacc acactggagc agcagtacaa caagcctctg tgcgacctcc   2040
tgatccgctg catcaactgc cagaagcctc tgtgccctga ggagaagcag agacacctgg   2100
acaagaagca gcggttccac aacatcagag gcagatggac cggcaggtgc atgtcctgct   2160
gtagatcctc cagaaccaga cgggagaccc agctgcacta acatcgtg accttctgct   2220 gcaagtgcga ctctaccctg agactgtgcg tgcagtctac ccacgtggac atcagaaccc   2280
tggaggacct gctgatgggc accctgggca tcgtgtgccc tatctgctct cagaagccta   2340
tgcaccagaa gagaaccgcc atgttccagg accctcagga gagacctagg aagctgcctc   2400
acctgtgtac agagctccag acaaccatcc acgacatcat cctggagtgc gtgtactgta   2460
agcagcagct gctgagaaga gaggtgtacg acttcgcctt cagagacctg tgcatcgtgt   2520
acagagacgg caaccccttac gccgtgtgcg ataagtgtct gaagttctat ccaaaatct   2580 ccgaatatag gtacatgcac ggcgacaccc ctaccctgca cgagtacatg ctggacctcc   2640
agcctgagac cacagacctg tactgctacg agcagctgaa cgacagctct gaggaagagg   2700
acgagattga cggacctgct ggccaggccg agcctgacag agcccactac aatatcgtga   2760
cattctgttg caaatgcgac tccacactga tggccaggtt cgaggaccct accagaagac   2820
cctacaagct gcctgacctg tgcaccgagc tgaacacctc tctgcaagac atcgagatca   2880
cctgcgtgta ctgcaagacc gtgctggagc tgaccgaggt gttcgagttc gccttcaagg   2940
acctgttcgt ggtgtacaga gacagcatcc tcacgctgc ctgccacaag tgcatcgact   3000
tctattccag gatcagggag ctgcgctatt actccgactc tgtgatgtac ggccccaagg   3060
ccaccctcca ggacatcgtg ctgcacctgg agcctcagaa cgagatcccc gtggacctgc   3120
tgtgccacga gcagctgtct gactctgaag aggagaacga cgagatcgac ggcgtgaacc   3180
accagcacct gcctgccagg agagctgaac cccagcggca taccatgctg tgtatgtgct   3240
tctactctag gatcagagag ctgaggtact actctgactc tgtgtacggc gacaccctgg   3300
agaagctgac caacaccggc ctgtacaacc tgctgatccg gtgcctgagg tgccagaagc   3360
ctctgaaccc tgccgagaag ctgagacacc tgaacgagaa gaagattc acaagatcg   3420 ctggccacta cagaggccag tgccactctt gctgcaacag agccagacag agagactcc   3480 agcggagaag ggagacccag gtggccagaa gagccgagcc tcagagacac accatgctgt   3540
gcatgtgctg caagtgcgag gccagaatcg agctggtggt ggagagctct gccgacgacc   3600
tgagagcctt ccagcagctg ttcctgtctta ccctgagctt cgtgtgccct tggtgcgcct   3660
ctcagcagta atctagagtc ggggcggccg gccgcttcga gcagacatga taagatacat   3720
tgatgagttt ggacaaacca caactagaat gcagtgaaaa aaatgcttta tttgtgaaat   3780
```

```
ttgtgatgct attgctttat ttgtaaccat tataagctgc aataaacaag ttaacaacaa    3840
caattgcatt cattttatgt ttcaggttca gggggaggtg tgggaggttt tttaaagcaa    3900
gtaaaacctc tacaaatgtg gtaaaatcga taaggatctg aacgatggag cggagaatgg    3960
gcggaactgg gcggagttag gggcgggatg ggcggagtta ggggcgggac tatggttgct    4020
gactaattga gatgcatgct ttgcatactt ctgcctgctg gggagcctgg ggactttcca    4080
cacctggttg ctgactaatt gagatgcatg ctttgcatac ttctgcctgc tggggagcct    4140
ggggactttc cacaccctaa ctgacacaca ttccacagcg gatccgtcga cttcagaaga    4200
actcgtcaag aaggcgatag aaggcgatgc gccgcgaatc gggagcggcg ataccgtaga    4260
gcacgaggaa gcggtcagcc cattcgccgc caagctcttc agcaatatca cgggtagcca    4320
acgctatgtc ctgatagcgg tccgccacac ccagccggcc acagtcgatg aatccagaaa    4380
agcggccatt ttccaccatg atattcggca agcaggcatc gccatgggtc acgacgagat    4440
cctcgccgtc gggcatgctc gccttgagcc tggcgaacag ttcggctggc gcgagcccct    4500
gatgctcttc gtccagatca tcctgatcga caagaccggc ttccatccga gtacgtgctc    4560
gctcgatgcg atgtttcgct tggtggtcga atgggcaggt agccggatca agcgtatgca    4620
gccgccgcat tgcatcagcc atgatggata ctttctcggc aggagcaagg tgagatgaca    4680
ggagatcctg ccccggcact cgcccaata gcagccagtc ccttcccgct tcagtgacaa    4740
cgtcgagcac agctgcgcaa ggaacgcccg tcgtggccag ccacgatagc cgcgctgcct    4800
cgtcttgcag ttcattcagg gcaccggaca ggtcggtctt gacaaaaaga accgggcgcc    4860
cctgcgctga cagccggaac acggcggcat cagagcagcc gattgtctgt tgtgcccagt    4920
catagccgaa tagcctctcc acccaagcgg ccggagaacc tgcgtgcaat ccatcttgtt    4980
caatcatgcg aaacgatcct catcctgtct cttgatcaga tcttgatccc ctgcgccatc    5040
agatccttgg cggcaagaaa gccatccagt ttactttgca gggcttccca accttaccag    5100
agggcgcccc agctggcaat tccggttcgc ttgctgtcca taaaaccgcc cagtctagct    5160
atcgccatgt aagcccactg caagctacct gctttctctt tgcgcttgcg ttttcccttg    5220
tccagatagc ccagtagctg acattcatcc ggggtcagca ccgtttctgc ggactggctt    5280
tctacgtgaa aaggatctag gtgaagatcc ttttgataa tctcatgacc aaaatccctt    5340
aacgtgagtt ttcgttccac tgagcgtcag accccgtaga aaagatcaaa ggatcttctt    5400
gagatccttt ttttctgcgc gtaatctgct gcttgcaaac aaaaaaacca ccgctaccag    5460
cggtggtttg tttgccggat caagagctac caactctttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagatacctg cagcgtgagc tatgagaaag cgccacgctt cccgaaggga    5820
gaaaggcgga caggtatccg gtaagcggca gggtcggaac aggagagcgc acgagggagc    5880
ttccagggga aaacgcccgg tatctttata gtcctgtcgg gtttcgccac ctctgacttg    5940
agcgtcgatt tttgtgatgc tcgtcagggg ggcggagcct atggaaaaac gccagcaacg    6000
cggccttttt acggttcctg gccttttgct ggccttttgc tcacatgttc gggcccaatc    6060
gacccgggcg acggccagtg aattg                                         6085
```

<210> SEQ ID NO 116
<211> LENGTH: 767
<212> TYPE: PRT
<213> ORGANISM: Artificial Sequence
<220> FEATURE:
<223> OTHER INFORMATION: E-2

<400> SEQUENCE: 116

```
Met Asp Ala Met Lys Arg Gly Leu Cys Cys Val Leu Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Gly Ser Gly Asp Ala Ser Asp Lys Cys Leu
            180                 185                 190

Lys Phe Tyr Ser Lys Ile Ser Glu Tyr Arg Tyr Cys Tyr Ser Val
        195                 200                 205

Tyr Gly Thr Thr Leu Glu Gln Gln Tyr Asn Lys Pro Leu Cys Asp Leu
    210                 215                 220

Leu Ile Arg Cys Ile Asn Cys Gln Lys Pro Leu Cys Pro Glu Glu Lys
225                 230                 235                 240

Gln Arg His Leu Asp Lys Lys Gln Arg Phe His Asn Ile Arg Gly Arg
                245                 250                 255

Trp Thr Gly Arg Cys Met Ser Cys Cys Arg Ser Ser Thr Arg Arg
            260                 265                 270

Glu Thr Gln Leu His Tyr Asn Ile Val Thr Phe Cys Cys Lys Cys Asp
        275                 280                 285

Ser Thr Leu Arg Leu Cys Val Gln Ser Thr His Val Asp Ile Arg Thr
    290                 295                 300

Leu Glu Asp Leu Leu Met Gly Thr Leu Gly Ile Val Cys Pro Ile Cys
305                 310                 315                 320

Ser Gln Lys Pro Met His Gln Lys Arg Thr Ala Met Phe Gln Asp Pro
                325                 330                 335

Gln Glu Arg Pro Arg Lys Leu Pro His Leu Cys Thr Glu Leu Gln Thr
            340                 345                 350

Thr Ile His Asp Ile Ile Leu Glu Cys Val Tyr Cys Lys Gln Gln Leu
        355                 360                 365

Leu Arg Arg Glu Val Tyr Asp Phe Ala Phe Arg Asp Leu Cys Ile Val
```

```
                    370                 375                 380
Tyr Arg Asp Gly Asn Pro Tyr Ala Val Cys Asp Lys Cys Leu Lys Phe
385                 390                 395                 400

Tyr Ser Lys Ile Ser Glu Tyr Arg Tyr Met His Gly Asp Thr Pro Thr
                405                 410                 415

Leu His Glu Tyr Met Leu Asp Leu Gln Pro Glu Thr Thr Asp Leu Tyr
                420                 425                 430

Cys Tyr Glu Gln Leu Asn Asp Ser Ser Glu Glu Glu Asp Glu Ile Asp
                435                 440                 445

Gly Pro Ala Gly Gln Ala Glu Pro Asp Arg Ala His Tyr Asn Ile Val
                450                 455                 460

Thr Phe Cys Cys Lys Cys Asp Ser Thr Leu Met Ala Arg Phe Glu Asp
465                 470                 475                 480

Pro Thr Arg Arg Pro Tyr Lys Leu Pro Asp Leu Cys Thr Glu Leu Asn
                485                 490                 495

Thr Ser Leu Gln Asp Ile Glu Ile Thr Cys Val Tyr Cys Lys Thr Val
                500                 505                 510

Leu Glu Leu Thr Glu Val Phe Glu Phe Ala Phe Lys Asp Leu Phe Val
                515                 520                 525

Val Tyr Arg Asp Ser Ile Pro His Ala Ala Cys His Lys Cys Ile Asp
                530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
                565                 570                 575

Gln Asn Glu Ile Pro Val Asp Leu Leu Cys His Glu Gln Leu Ser Asp
                580                 585                 590

Ser Glu Glu Glu Asn Asp Glu Ile Asp Gly Val Asn His Gln His Leu
                595                 600                 605

Pro Ala Arg Arg Ala Glu Pro Gln Arg His Thr Met Leu Cys Met Cys
610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
                645                 650                 655

Ile Arg Cys Leu Arg Cys Gln Lys Pro Leu Asn Pro Ala Glu Lys Leu
                660                 665                 670

Arg His Leu Asn Glu Lys Arg Arg Phe His Lys Ile Ala Gly His Tyr
                675                 680                 685

Arg Gly Gln Cys His Ser Cys Cys Asn Arg Ala Arg Gln Glu Arg Leu
                690                 695                 700

Gln Arg Arg Arg Glu Thr Gln Val Ala Arg Arg Ala Glu Pro Gln Arg
705                 710                 715                 720

His Thr Met Leu Cys Met Cys Cys Lys Cys Glu Ala Arg Ile Glu Leu
                725                 730                 735

Val Val Glu Ser Ser Ala Asp Asp Leu Arg Ala Phe Gln Gln Leu Phe
                740                 745                 750

Leu Ser Thr Leu Ser Phe Val Cys Pro Trp Cys Ala Ser Gln Gln
                755                 760                 765
```